(12) United States Patent
Rigas

(10) Patent No.: US 11,752,146 B2
(45) Date of Patent: Sep. 12, 2023

(54) ANTI-INFLAMMATORY, ANTI-CANCER, AND ANTI-ANGIOGENIC COMPOUNDS, PHARMACEUTICAL COMPOSITIONS, AND METHODS OF MAKING AND USING THEREOF

(71) Applicant: MEDICON PHARMACEUTICALS, INC., Setauket, NY (US)

(72) Inventor: Basil Rigas, Setauket, NY (US)

(73) Assignee: MEDICON PHARMACEUTICALS, INC., Setauket, NY (US)

( * ) Notice: Subject to any disclaimer, the term of this patent is extended or adjusted under 35 U.S.C. 154(b) by 339 days.

(21) Appl. No.: 16/651,826

(22) PCT Filed: Sep. 28, 2018

(86) PCT No.: PCT/US2018/053537
§ 371 (c)(1),
(2) Date: Mar. 27, 2020

(87) PCT Pub. No.: WO2019/067974
PCT Pub. Date: Apr. 4, 2019

(65) Prior Publication Data
US 2020/0246330 A1    Aug. 6, 2020

Related U.S. Application Data

(60) Provisional application No. 62/564,610, filed on Sep. 28, 2017.

(51) Int. Cl.
*A61K 31/495* (2006.01)
*A61P 27/02* (2006.01)
(Continued)

(52) U.S. Cl.
CPC .......... *A61K 31/495* (2013.01); *A61K 9/0019* (2013.01); *A61K 9/0048* (2013.01);
(Continued)

(58) Field of Classification Search
CPC .. A61K 31/495; A61K 9/0019; A61K 9/0048; A61K 31/166; A61K 31/664;
(Continued)

(56) References Cited

U.S. PATENT DOCUMENTS 4,992,445 A    2/1991  Lawter et al.
5,001,139 A    3/1991  Lawter et al.
(Continued)

FOREIGN PATENT DOCUMENTS

EP        2711006 A1      3/2014
WO    2007081694 A2      7/2007
(Continued)

OTHER PUBLICATIONS

Danziger, Automated site-directed drug design: a general algorithm for knowledge acquisition about hydrogen-bonding regions at protein surfaces, Proc. R. Soc. Lond., 1989, 236, pp. 101-113 (Year: 1989).*

(Continued)

*Primary Examiner* — Savitha M Rao
*Assistant Examiner* — Andrew P Lee
(74) *Attorney, Agent, or Firm* — Cynthia Hathaway; Lauren L. Stevens; Erik M. Larsen

(57) ABSTRACT

Compounds of the general Formula A-D-Y are disclosed with activity towards treating diseases related to inflammation, cancer, neurodegenerative diseases, and cardiovascular diseases. Pharmaceutical compositions, methods of making, and methods of use thereof are also described.

8 Claims, 21 Drawing Sheets

(51) Int. Cl.
  *A61P 35/00*    (2006.01)
  *A61K 9/00*     (2006.01)
  *A61K 31/166*    (2006.01)
  *A61K 31/664*    (2006.01)
  *A61K 45/06*    (2006.01)
  *C07C 233/78*    (2006.01)
  *C07D 241/04*    (2006.01)
  *C07F 9/22*     (2006.01)
(52) U.S. Cl.
  CPC .......... *A61K 31/166* (2013.01); *A61K 31/664* (2013.01); *A61K 45/06* (2013.01); *A61P 27/02* (2018.01); *A61P 35/00* (2018.01); *C07C 233/78* (2013.01); *C07D 241/04* (2013.01); *C07F 9/222* (2013.01)
(58) Field of Classification Search
  CPC .......... A61K 45/06; A61P 27/02; A61P 35/00; C07C 233/78; C07C 241/04; C07C 317/44; C07C 317/32362; C07F 9/222; C07F 9/2458; C07F 9/650952
  See application file for complete search history.

(56) References Cited

U.S. PATENT DOCUMENTS

| | | | |
|---|---|---|---|
| 5,023,252 | A | 6/1991 | Hseih |
| 8,236,820 | B2 | 8/2012 | Rigas |
| 2014/0121185 | A1 | 5/2014 | Rigas |
| 2014/0315834 | A1 | 10/2014 | Rigas |
| 2018/0121618 | A1 | 5/2018 | Smith et al. |

FOREIGN PATENT DOCUMENTS

| | | |
|---|---|---|
| WO | 2008017903 A1 | 2/2008 |
| WO | 2009023631 A1 | 2/2009 |
| WO | 2014047592 A2 | 3/2014 |

OTHER PUBLICATIONS

Simone, Oncology: Introduction, Textbook of Medicine, 1997, 14, pp. 1004-1010 (Year: 1997).*
International Search Report dated Nov. 19, 2018 in connection with International Patent Application No. PCT/US2018/053537.
Written Opinion dated Nov. 19, 2018 in connection with International Patent Application No. PCT/US2018/053537.
PubChem CID 89771416, pp. 1-12, Create Date: Feb. 13, 2015; p. 4.
Pubchem CID 71696699, pp. 1-13, Create Date: Sep. 16, 2013; p. 4.
Bini M. et al., "Diverse amide analogs of sulindac for cancer treatment and prevention", Biorganic & Medicinal Chemistry Letters, vol. 27, No. 20, Sep. 13, 2017 (Sep. 13, 2017), pp. 4614-4621.
Yu C. et al., XP055804536 (Techfields Biochem Co Ltd, Positively charged water-soluble prodrugs of aryl- and heteroarylacetic acids with very fast skin penetration rate, Feb. 14, 2008 (Feb. 14, 2008).
European Partial Supplementary Search Report for European Application No. 18860072.0, dated Jun. 1, 2021, issued by the European Searching Authority dated May 18, 2021.
Boland, CR et al., Microsatellite Instability in Colorectal Cancer, Gastroenterology (2010) 138(6): 2073-87; doi 10.1053/j.gastro.2009. 12.064)).
Bowtell DD et al., Rethinking ovarian cancer II: reducing mortality from high-grade serous ovarian cancer. Nat Rev Cancer 2015;15(11):668-79.
Cheng KW et al., Aerosol administration of phospho-sulindac inhibits lung tumorigenesis Mol Cancer Tuer 2013;12(8): 1417-28.
Coleman RL et al., Latest research and treatment of advanced-stage epithelial ovarian cancer. Nat Rev Clin Oncol 2013;10(4):211-24.
Cortez AJ et al., Advances in ovarian cancer therapy. Cancer Chemother Pharmacol 2018;81(1):17-38.
Coward JI et al., New perspectives on targeted therapy in ovarian cancer. Int J Womens Health 2015;7:189-203.
Doubeni CA et al., Diagnosis and Management of Ovarian Cancer. Am Fam Physician 2016;93(11):937-44.
Duh EJ et al., Diabetic retinopathy: current understanding, mechanisms, and treatment strategies. JCI Insight 2017;2(14).
Fidler MM, et al., The global cancer burden and human development: A review. Scand J Public Health 2018;46(1):27-36.
Fitzmaurice C, et al., Global Burden of Disease Cancer C, Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study. JAMA Oncol 2018.
Geraci, JM et al., Comorbid Disease and Cancer: The Need for More Relevant Conceptual Models in Health Services Research, J Clin. Oncol (2005) 23(30): 7399-7404.
Giomelli GH, Management of relapsed ovarian cancer: a review. Springerplus 2016,5(1): 1197.
Julianne C. et al., Corneal Melting Associated with Use of Topical Nonsteroidal Anti-Inflammatory Drugs after Ocular Surgery, (2000) 118:1129-1132.
Kim CB et al., Revisiting the mouse model of oxygen-induced retinopathy. Eye Brain 2016;8:67-79.
Lin DTS et al., Targeting the Ras palmitoylation/depalmitoylation cycle in cancer. Biochem Soc Trans 2017;45(4):913-21.
Tamochi H., Targeted therapies in epithelial ovarian cancer: Molecular mechanisms of action. World J Biol Chem 2010;1(7):209-20.
Mackenzie GG et al., PhosphoÂ-sulindac (OXT-328), a novel sulindac derivative, is safe and effective in colon cancer prevention in mice. Gastroenterology 2010; 139( 4): 1320-32.
Markam M et al., Intraperitoneal chemotherapy of ovarian cancer: a review, with a focus on practical aspects of treatment. J Clin Oncol 2006;24(6):988-94.
Matulonis UA et al., Ovarian cancer. Nat Rev Dis Primers 2016;2:16061.
Narod S et al., Can advanced-stage ovarian cancer be cured? Nat Rev Clin Oncol 2016; 13(4):255-61.
National Institutes of Health. National Cancer Institute. Surveillance, Epidemiology, and End Results Program. Statistical summaries: cancer stat fact sheets (ovary) and cancer statistics review (CSR), 1975-2013, http:! /seer.cancer.gov/statistics/summaries. html, 2016.
Nikolaou M et al., The challenge of drug resistance in cancer treatment: a current overview. Clin Exp Metastasis 2018;35(4):309-18.
Oakes SA et al., Papa FR The role of endoplasmic reticulum stress in human pathology. AnnuRev Pathol 2015;10:173-94.
Oken, MM, et al, "Toxicity and response criteria of the Eastern Cooperative Oncology Group," Am. J. Clin. Oncol. (1982) 5: 649-655.
Olivares AM et al., Animal Models of Diabetic Retinopathy. Curr Diab Rep 2017; 17(10):93.
Pakos-Zebrucka et al., The integrated stress response. EMBO Rep 2016; 17(10): 1374-95.
Patel et al., Ocular drug delivery stystems: An overview, World J Pharmacol, 2013; 2(2): 47-64.
Prager GW et al., Global cancer control: responding to the growing burden, rising costs and inequalities in access. ESMO Open 2018;3(2):e000285.
Reid BM et al., Epidemiology of ovarian cancer: a review. Cancer Biol Med 2017;14(1):9-32.
RilGAS B et al., Induction of oxidative stress as a mechanism of action of chemopreventive agents against cancer. Br J Cancer 2008;98(7): 1157-60.
ROMERO I et al., Minireview: human ovarian cancer: biology, current management, and paths to personalizing therapy. Endocrinology 2012;153(4): 1593-602.
Rosen DG et al., Ovarian cancer: pathology, biology, and disease models. Front Biosci (Landmark Ed) 2009; 14: 2089-102.
Sun Y et al., Oxidative stress mediates through apoptosis the anticancer effect of phospho-nonsteroidal anti-inflammatory drugs:

(56) References Cited

OTHER PUBLICATIONS implications for the role of oxidative stress in the action of anticancer agents. J Pharmacol Exp Tuer 2011;338(3):775-83.
Vaughan S et al., Rethinking ovarian cancer: recommendations for improving outcomes. Nat Rev Cancer 2011; 11(10):719-25.
Westin SN et al., Investigational agents in development for the treatment of ovarian cancer. Invest New Drugs 2013;31(1):213-29.
Yokoyama C et al., Induction of oxidative stress by anticancer drugs in the presence and absence of cells. Oncol Lett 2017;14(5):6066-70.

\* cited by examiner

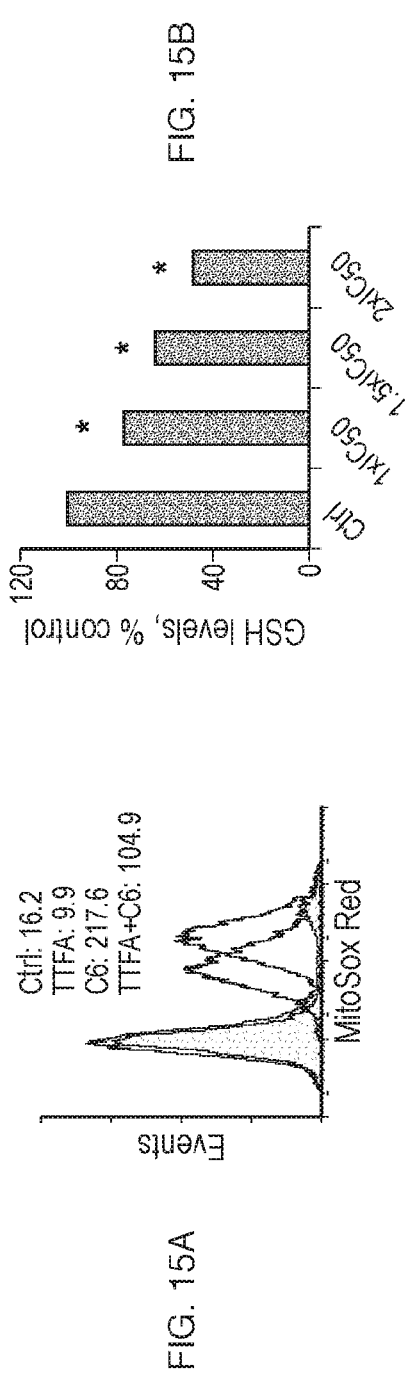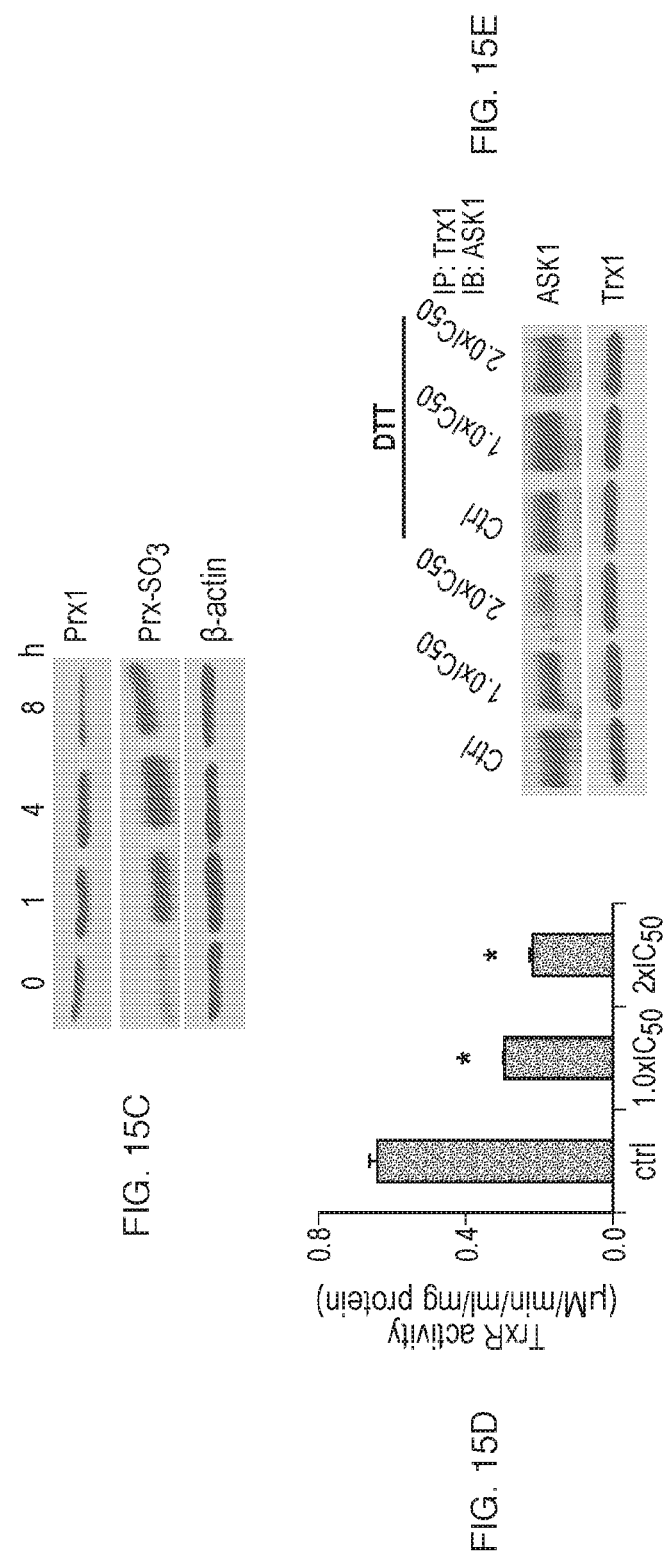
FIG. 15A  FIG. 15B  FIG. 15C  FIG. 15D  FIG. 15E

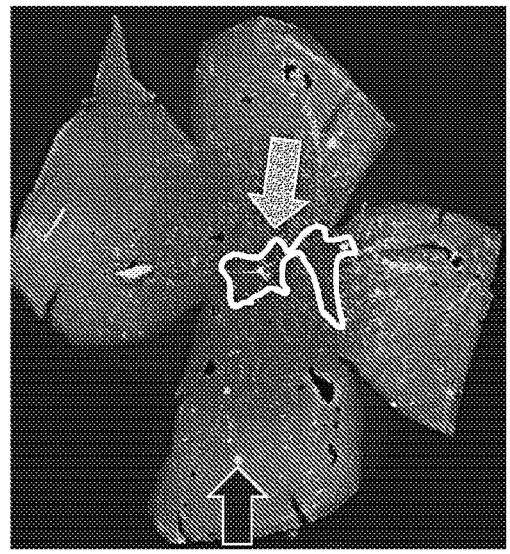
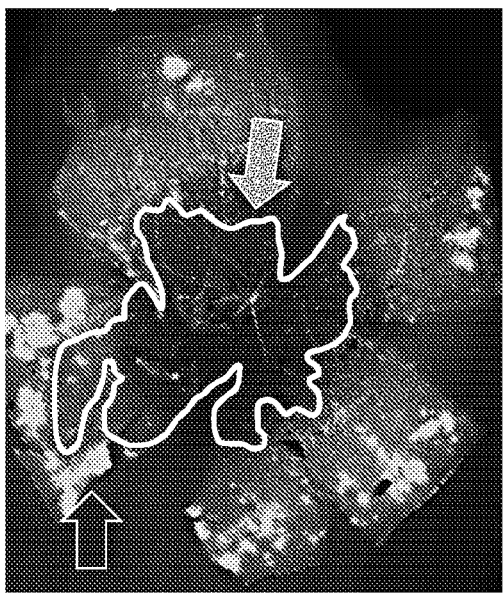
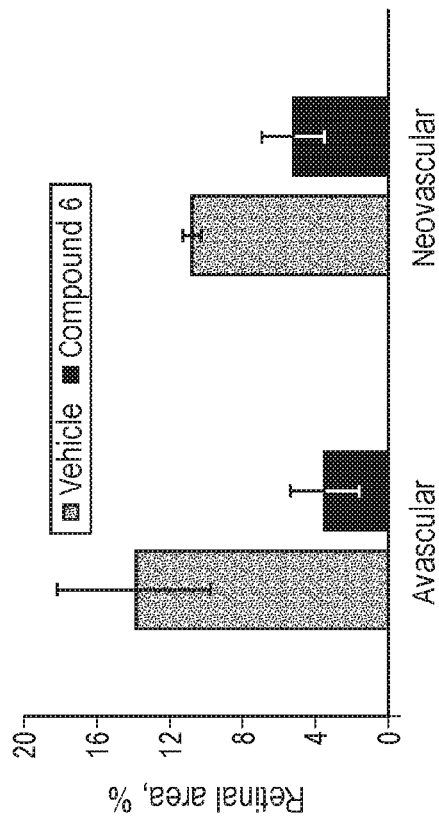
FIG. 19A
FIG. 19B

ANTI-INFLAMMATORY, ANTI-CANCER, AND ANTI-ANGIOGENIC COMPOUNDS, PHARMACEUTICAL COMPOSITIONS, AND METHODS OF MAKING AND USING THEREOF

CROSS-REFERENCE TO RELATED APPLICATIONS

This application is a U.S. National Stage application of International Patent Application No. PCT/US2018/053537 filed Sep. 28, 2018, which claims the benefit of U.S. Provisional Patent Application No. 62/564,610 filed Sep. 28, 2017, which are hereby incorporated by reference in their entireties.

FIELD OF THE INVENTION

The invention relates generally to compounds of Formula A-D-Y, and methods of making and using such compounds as treatments for diseases or disorders.

BACKGROUND OF THE INVENTION

The cancer burden is rising globally, exerting significant strain on populations and health systems at all income levels. In May 2017, world governments made a commitment to further invest in cancer control as a public health priority. Each year, tens of millions of people are diagnosed with cancer around the world, and more than half of the patients eventually die from it. A major reason for the increasing burden of cancer is the lack of efficacious and safe drugs that address this pressing medical need.

A remarkable property of the cancer cells is to respond to chemotherapy by becoming resistant to it, often rapidly. Ovarian cancer is a case in point. Ovarian cancer is the leading cause of death in women with gynecological cancer, with over 125,000 deaths annually worldwide. Ovarian cancer often spreads within the peritoneum; its stage dictates its treatment. Indeed, in 75% of patients the cancer is spread into the peritoneal cavity (stage III) or more distantly (stage IV) and is treated with surgery plus chemotherapy with platinum and a taxane. The response rate is 80% but most of those who respond develop drug resistance (often within 6 months), and subsequent treatment with other agents is rarely successful. The 5-year survival of ovarian cancer patients stage III disease is 40% and with stage IV 20%. Rates of survival have not changed in the last 20 years.

Diabetic retinopathy (DR) causes significant visual loss on a global scale. The global prevalence of diabetes mellitus is predicted to increase dramatically in the coming decades, from an estimated 382 million in 2013 to 592 million by 2035. Patients with diabetes suffer many life-limiting and life-threatening complications, including macrovascular-related stroke, ischemic heart disease, and peripheral artery disease and/or microvascular-related retinopathy, neuropathy, and nephropathy. Diabetic retinopathy (DR) is the most common microvascular complication of diabetes. The control of DR is still suboptimal and treatments injectable into the eye, as currently available, are expensive, associated with complication and not optimally efficacious. DR represents another pressing medical need of global importance.

Inflammation, a key component of the immune system, functions in both defense and pathophysiological events to maintain the homeostasis of tissues, organs and individual cells. Inflammation can be classified as either acute or chronic. Acute inflammation is a short-term process characterized by the classic signs of inflammation, i.e., swelling, redness, pain, heat, and loss of function, due to infiltration of tissues by plasma and leukocytes. It occurs as long as the injurious stimulus is present and ceases once the stimulus has been removed. Chronic inflammation is a pathological condition characterized by concurrent active inflammation, tissue destruction, and attempts at repair. Chronically inflamed tissue is characterized by the infiltration of mononuclear immune cells (monocytes, macrophages, lymphocytes, and plasma cells), tissue destruction, and attempts at healing, which include angiogenesis and fibrosis. Without inflammation, wounds and infections would not be able to heal and progressive destruction of the tissue would threaten the survival of the organism. Unchecked inflammation, on the other hand, can lead to a host of diseases, such as hay fever, atherosclerosis and other cardiovascular diseases, neurodegenerative diseases such as Alzheimer's, cancer and rheumatoid arthritis. For these reasons, inflammation is tightly regulated by the body. Nonsteroidal anti-inflammatory drugs (NSAIDS) are the most widely used anti-inflammatory compounds, with aspirin, the prototypical NSAID, still being one of the oldest and most extensively used medication in the world. NSAIDs can also prevent cancer, likely through pleiotropic effects.

SUMMARY OF THE INVENTION

In one embodiment, the invention relates to a compound of Formula A-D-Y, or a pharmaceutically acceptable salt, solvate, hydrate, cocrystal, or prodrug thereof. In some embodiments, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1.

TABLE 1

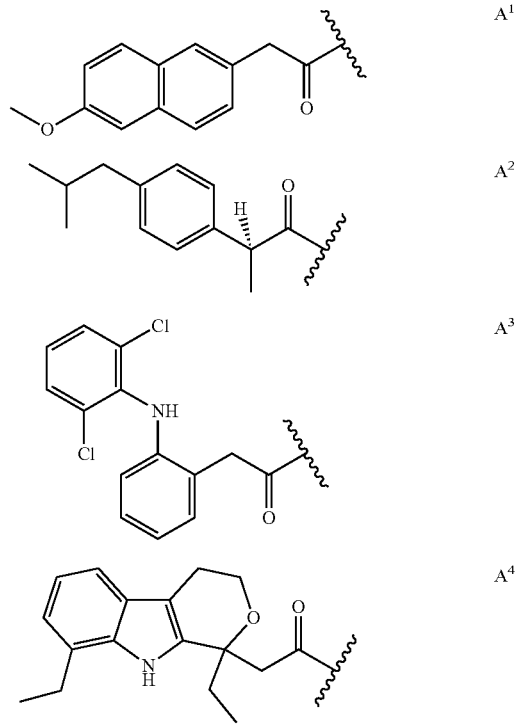

TABLE 1-continued
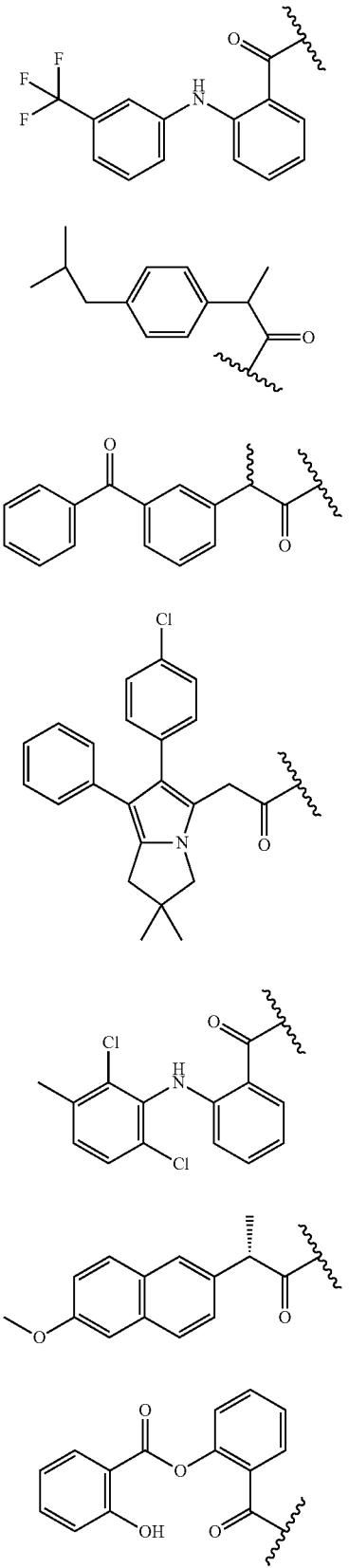
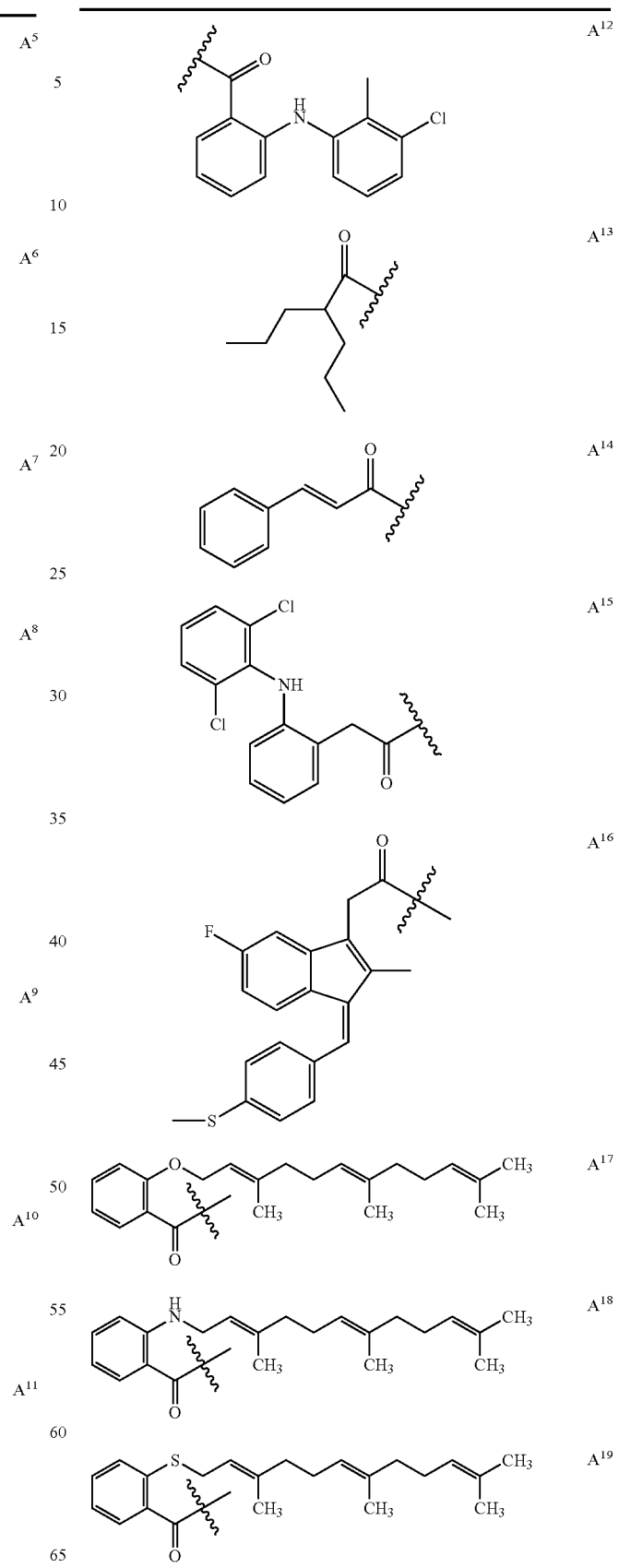

TABLE 1-continued
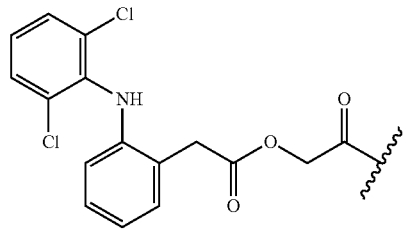 [SMILES: *C(=O)COC(=O)Cc1ccccc1Nc1c(Cl)cccc1Cl] A20
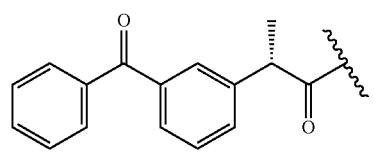 [SMILES: *C(=O)[C@@H](C)c1cccc(C(=O)c2ccccc2)c1] A21
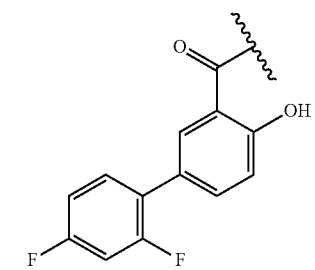 [SMILES: *C(=O)c1cc(-c2ccc(F)cc2F)ccc1O] A22
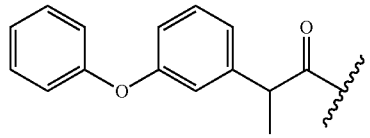 [SMILES: *C(=O)C(C)c1cccc(Oc2ccccc2)c1] A23
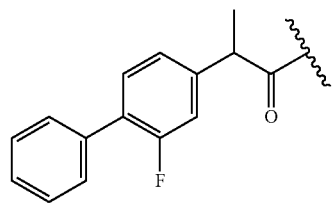 [SMILES: *C(=O)C(C)c1ccc(-c2ccccc2)c(F)c1] A24
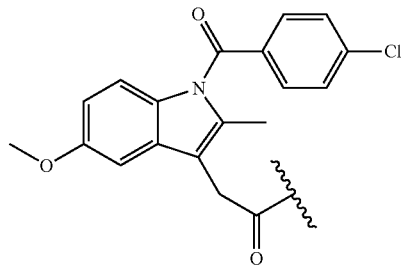 [SMILES: *C(=O)Cc1c(C)n(C(=O)c2ccc(Cl)cc2)c2ccc(OC)cc12] A25
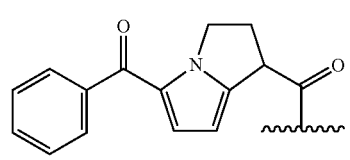 [SMILES: *C(=O)C1CCn2c(C(=O)c3ccccc3)ccc21] A26
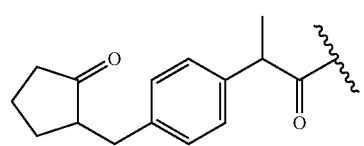 [SMILES: *C(=O)C(C)c1ccc(CC2CCCC2=O)cc1] A27
TABLE 1-continued
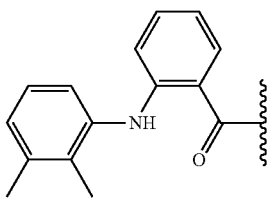 [SMILES: *C(=O)c1ccccc1Nc1cccc(C)c1C] A28
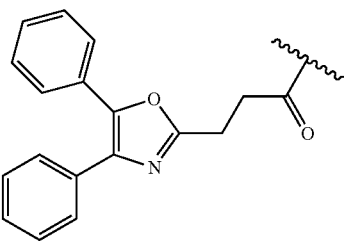 [SMILES: *C(=O)CCc1nc(-c2ccccc2)c(-c2ccccc2)o1] A29
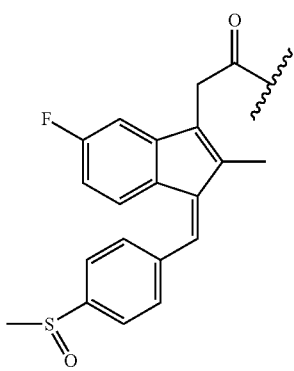 [SMILES: *C(=O)CC1=C(C)/C(=C/c2ccc(S(C)=O)cc2)c2ccc(F)cc21] A30
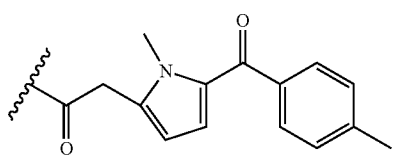 [SMILES: *C(=O)Cc1ccc(C(=O)c2ccc(C)cc2)n1C] A31
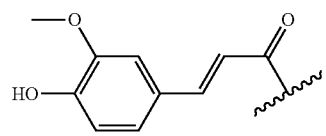 A32
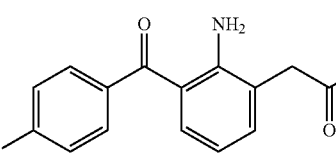 A33
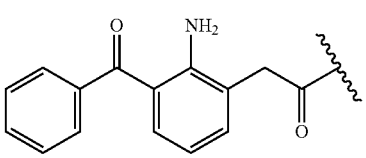 [SMILES: *C(=O)Cc1cccc(C(=O)c2ccccc2)c1N] A34

TABLE 1-continued

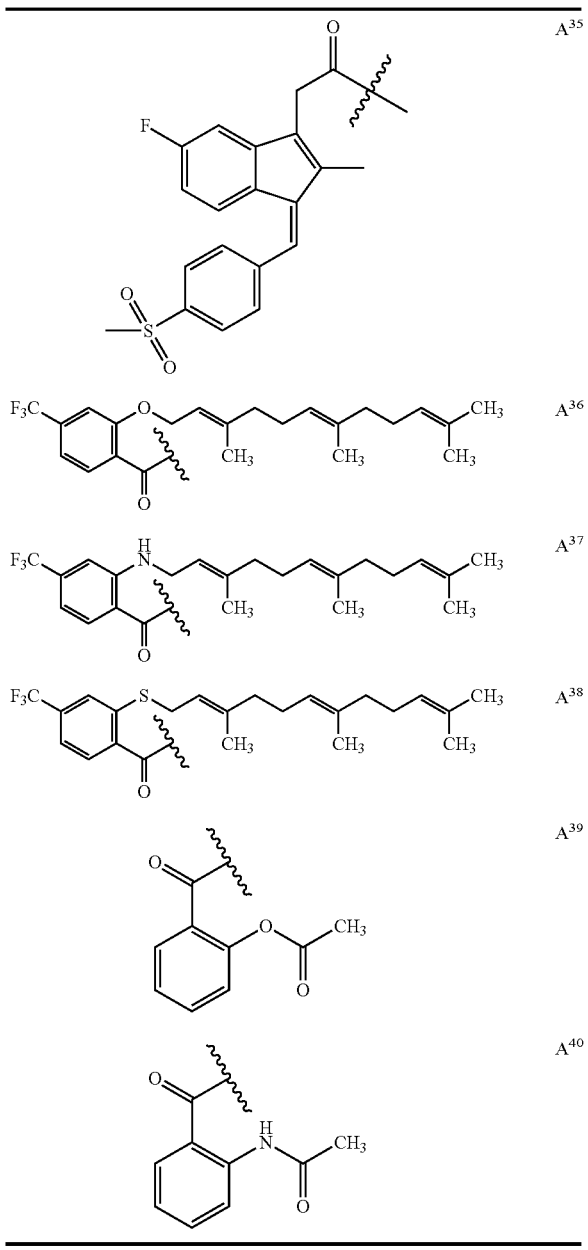

TABLE 2

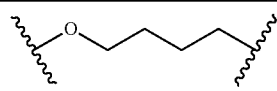

TABLE 2-continued

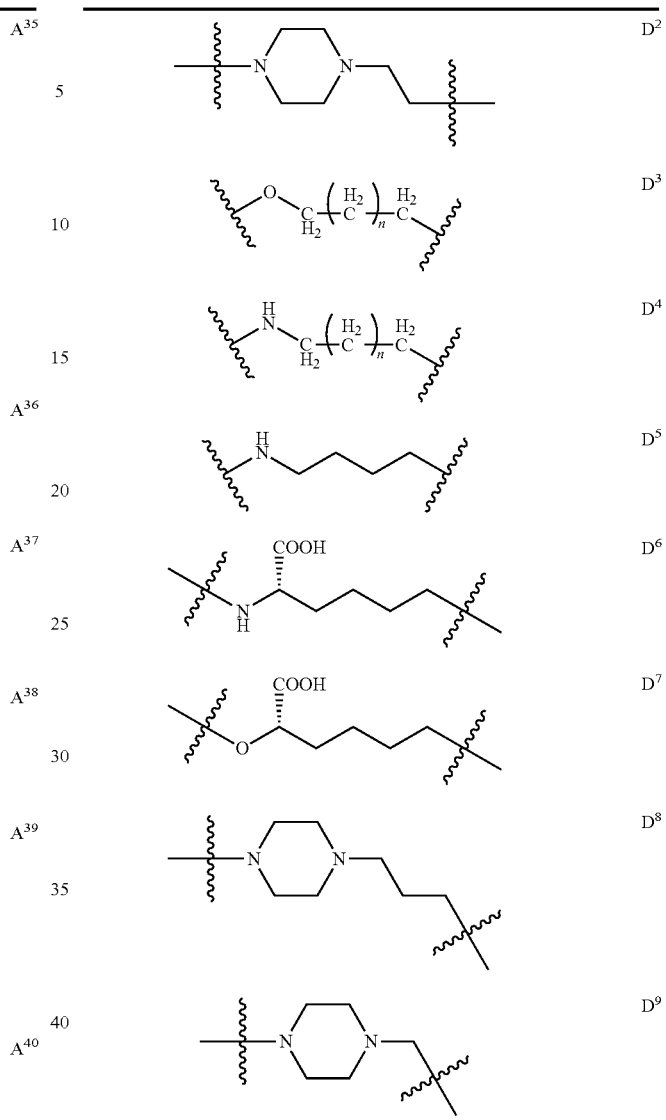

n is an integer between 0 and 12

In one embodiment, the invention relates to a compound of Formula A-D-Y, or a pharmaceutically acceptable salt, solvate, hydrate, cocrystal, or prodrug thereof, wherein D is selected from the group consisting of $D^1$ to $D^9$ as defined in Table 2. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, and D is selected from the group consisting of $D^1$ to $D^9$ as defined in Table 2. In one embodiment, the invention relates to a compound of Formula A-D-Y, or a pharmaceutically acceptable salt, solvate, hydrate, cocrystal, or prodrug thereof, wherein Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, and Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein D is selected from the group consisting of $D^1$ to $D^9$ as defined in Table 2, and Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, D is selected from the group consisting of $D^1$ to $D^9$ as defined in Table 2, and Y is selected from the group consisting of $Y^1$ to $Y^7$ as defined in Table 3.

TABLE 3

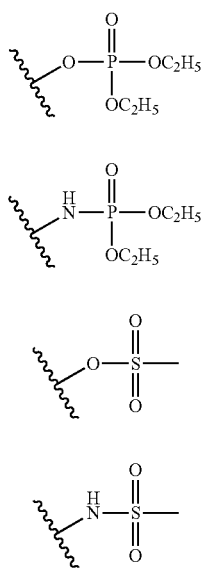

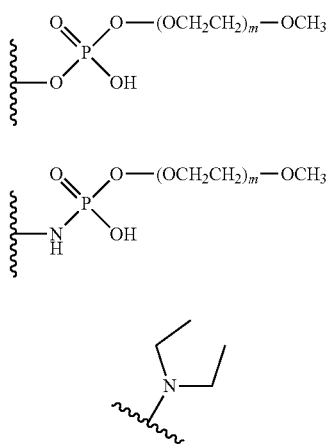

m is an integer between 1 and 12

In some embodiments, the invention relates to a compound of Formula A-D-Y, or a pharmaceutically acceptable salt, solvate, hydrate, cocrystal, or prodrug thereof, wherein the compound has anti-inflammatory, anticancer, or antiangiogenic effects.

In some embodiments, the invention relates to a pharmaceutical composition including a compound of Formula A-D-Y, or a pharmaceutically acceptable salt, solvate, hydrate, cocrystal, or prodrug thereof. In some embodiments, A is selected from the group consisting of $A^1$ to $A^{40}$ as defined in Table 1. In some embodiments, D is selected from the group consisting of $D^1$ to $D^9$ as defined in Table 2. In some embodiments, Y is selected from the group consisting of $Y^1$ to $Y^7$ as defined in Table 3.

In one embodiment, the invention relates to compound 1, or a pharmaceutically acceptable salt, solvate, hydrate, cocrystal, or prodrug thereof. In one embodiment, the invention relates to a pharmaceutical composition including compound 1, or a pharmaceutically acceptable salt, solvate, hydrate, cocrystal, or prodrug thereof, and a pharmaceutically acceptable excipient.

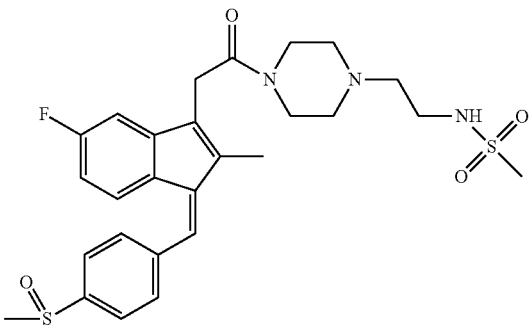

Compound 1

In one embodiment, the invention relates to compound 2, or a pharmaceutically acceptable salt, solvate, hydrate, cocrystal, or prodrug thereof. In one embodiment, the invention relates to a pharmaceutical composition including compound 2, or a pharmaceutically acceptable salt, solvate, hydrate, cocrystal, or prodrug thereof, and a pharmaceutically acceptable excipient.

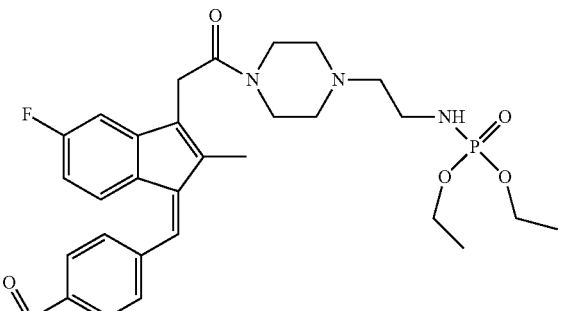

Compound 2

In one embodiment, the invention relates to compound 3, or a pharmaceutically acceptable salt, solvate, hydrate, cocrystal, or prodrug thereof. In one embodiment, the invention relates to a pharmaceutical composition including compound 3, or a pharmaceutically acceptable salt, solvate, hydrate, cocrystal, or prodrug thereof, and a pharmaceutically acceptable excipient.

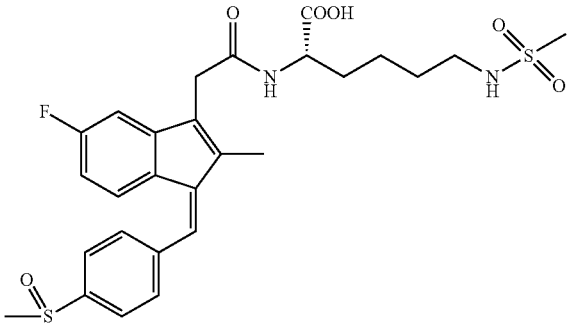

Compound 3

In one embodiment, the invention relates to compound 4, or a pharmaceutically acceptable salt, solvate, hydrate, cocrystal, or prodrug thereof. In one embodiment, the invention relates to a pharmaceutical composition including compound 4, or a pharmaceutically acceptable salt, solvate, hydrate, cocrystal, or prodrug thereof, and a pharmaceutically acceptable excipient.

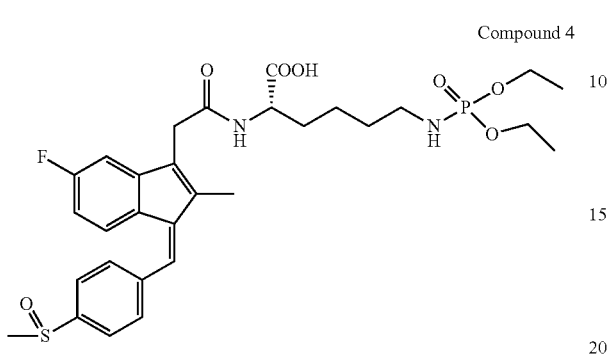

Compound 4

In one embodiment, the invention relates to compound 5, or a pharmaceutically acceptable salt, solvate, hydrate, cocrystal, or prodrug thereof. In one embodiment, the invention relates to a pharmaceutical composition including compound 5, or a pharmaceutically acceptable salt, solvate, hydrate, cocrystal, or prodrug thereof, and a pharmaceutically acceptable excipient.

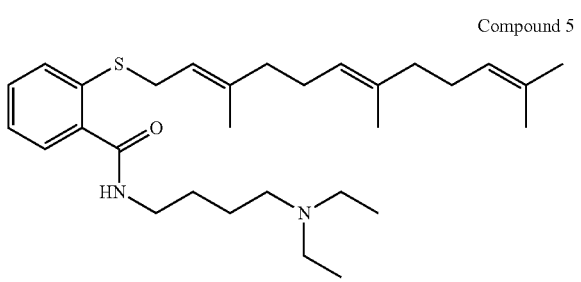 [SMILES: CCN(CC)CCCCNC(=O)c1ccccc1SC/C=C(\C)CC/C=C(\C)CCC=C(C)C]

Compound 5

In one embodiment, the invention relates to compound 6, or a pharmaceutically acceptable salt, solvate, hydrate, cocrystal, or prodrug thereof. In one embodiment, the invention relates to a pharmaceutical composition including compound 6, or a pharmaceutically acceptable salt, solvate, hydrate, cocrystal, or prodrug thereof, and a pharmaceutically acceptable excipient.

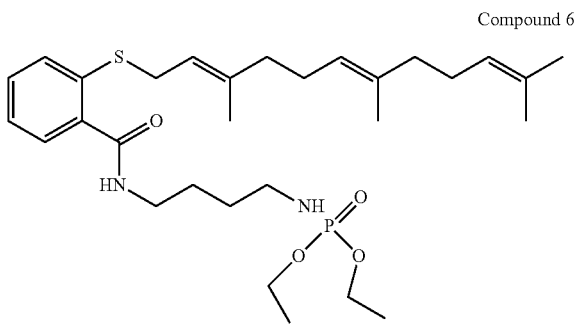

Compound 6

In one embodiment, the invention relates to compound 7, or a pharmaceutically acceptable salt, solvate, hydrate, cocrystal, or prodrug thereof. In one embodiment, the invention relates to a pharmaceutical composition including compound 7, or a pharmaceutically acceptable salt, solvate, hydrate, cocrystal, or prodrug thereof, and a pharmaceutically acceptable excipient.

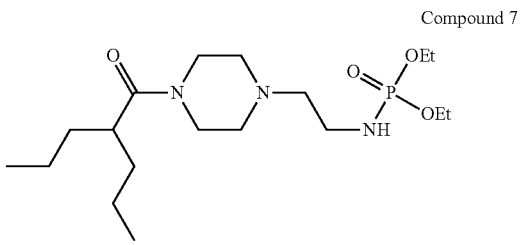 [SMILES: CCCC(CCC)C(=O)N1CCN(CCNP(=O)(OCC)OCC)CC1]

Compound 7

In one embodiment, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof. In some embodiments, A is selected from the group consisting of $A^1$ to $A^{40}$ as defined in Table 1. In some embodiments, D is selected from the group consisting of $D^1$ to $D^9$ as defined in Table 2. In some embodiments, Y is selected from the group consisting of $Y^1$ to $Y^7$ as defined in Table 3. In some embodiments, the compound, or a pharmaceutically acceptable salt, solvate, hydrate, cocrystal, or prodrug thereof, is included in a pharmaceutical composition further including a pharmaceutically acceptable excipient. In some embodiments, the disease or disorder is an inflammation disease or disorder, a cancer, a neurodegenerative diseases or disorder, a cardiovascular disease or disorder, an ocular disease or disorder, or an angiogenic disease or disorder. In some embodiments, the cancer is ovarian cancer, colon cancer, leukemia, gastric cancer, lung cancer, pancreatic cancer, or a cancer characterized by a K-Ras mutation. In some embodiments, the cancer is chemoresistant to other therapeutic agents. In some embodiments, treatment includes inhibiting VEGF expression.

In some embodiments, the disease or disorder is an eye related disease or disorder. The eye consists of the eyeball and its adnexa, which includes the structures outside of the eyeball, such as the orbit, eye muscles, eyelids, eyelashes, conjunctiva, and lacrimal apparatus. The eye and its various structures may be affected by a number of pathological conditions including various inflammatory, autoimmune, and metabolic conditions. In some embodiments, the invention relates to a method for treating various diseases, disorders, and/or conditions of the eye and its associated structures, i.e., ophthalmic diseases, disorders, or conditions. In some embodiments, the ophthalmic diseases, disorders, or conditions treated by the compounds, compositions, and/or kits of the invention may include dry eye disease and retinopathy. In some embodiments, retinopathy may include the diseases of diabetic retinopathy, retinopathy of prematurity, and/or hypertensive retinopathy. In certain embodiments, retinopathy may be diabetic retinopathy.

In a further aspect, the invention is directed to compounds of Formula A-D-Y, and pharmaceutical compositions thereof, as described generally herein, useful in the treatment of human and animal inflammation related diseases including but not limited to neoplasms and cancer, rheumatologic diseases such as rheumatoid arthritis and Sjögren's syndrome, cardiovascular diseases, such as coronary artery disease, peripheral vascular disease and hypertension, neurodegenerative diseases such as Alzheimer's disease and its variants or cerebrovascular diseases, autoimmune diseases such as lupus erythematosus, and other conditions characterized by chronic inflammation of organs such as the lung, chronic bronchitis or the sinuses, such as chronic sinusitis, cardiovascular diseases, for example, coronary artery disease, peripheral vascular disease and hypertension, various neoplastic and pre-neoplastic diseases, for example, benign prostatic hypertrophy, prostate cancer, colon adenomas and colon cancer, cancer of the lung, lymphomas and leukemias. Similarly useful compounds have been described in U.S. Pat. No. 8,236,820, the contents of which are incorporated in their entirety herein.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of Formula A-D-Y, or a pharmaceutically acceptable salt, solvate, hydrate, cocrystal, or prodrug thereof, a pharmaceutically acceptable carrier, and one or more of a solubilizing agent, e.g., vitamin E TPGS (d-α-tocopheryl polyethylene glycol 1000 succinate), a sugar alcohol, e.g., mannitol, an acid, e.g., boric acid, and a preservative, e.g., polyquaternium-1 (polyquad). In some embodiments, such formulations may be used to deliver a compound of Formula A-D-Y, or a pharmaceutically acceptable salt, solvate, hydrate, cocrystal, or prodrug thereof, to the retina following topical administration to the eye. In some embodiments, such formulations may be used to deliver a compound of Formula A-D-Y, or a pharmaceutically acceptable salt, solvate, hydrate, cocrystal, or prodrug thereof, to the retina in an amount sufficient to treat a retinopathy (i.e., a therapeutically effective amount).

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of Formula A-D-Y, or a pharmaceutically acceptable salt, solvate, hydrate, cocrystal, or prodrug thereof, a pharmaceutically acceptable carrier, and one or more of about 0% to about 25% vitamin E TPGS (d-α-tocopheryl polyethylene glycol 1000 succinate), about 0% to about 10% mannitol, about 0% to about 10% boric acid, and about 0% to about 1% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of Formula A-D-Y, or a pharmaceutically acceptable salt, solvate, hydrate, cocrystal, or prodrug thereof, a pharmaceutically acceptable carrier, and one or more of greater than 5% vitamin E TPGS (d-α-tocopheryl polyethylene glycol 1000 succinate), greater than 0.5% mannitol, greater than 0.5% boric acid, and greater than 0.001% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of Formula A-D-Y, or a pharmaceutically acceptable salt, solvate, hydrate, cocrystal, or prodrug thereof, a pharmaceutically acceptable carrier, and one or more of less than 25% vitamin E TPGS (d-α-tocopheryl polyethylene glycol 1000 succinate), less than 10% mannitol, less than 10% boric acid, and less than 1% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising, by weight, about 3.5% of a compound of Formula A-D-Y, or a pharmaceutically acceptable salt, solvate, hydrate, cocrystal, or prodrug thereof, a pharmaceutically acceptable carrier, and one or more of about 16% vitamin E TPGS (d-α-tocopheryl polyethylene glycol 1000 succinate), about 3.18% mannitol, about 1.2% boric acid, and about 0.005% polyquaternium-1 (polyquad).

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of Formula A-D-Y, or a pharmaceutically acceptable salt, solvate, hydrate, cocrystal, or prodrug thereof, a pharmaceutically acceptable carrier, and one or more of a gelling excipient, e.g., gellan gum or sodium alginate, a poloxamer, a solubilizing agent, e.g., vitamin E TPGS, and a cyclodextrin (e.g., (2-hydroxypropyl)-β-cyclodextrin). In some embodiments, such formulations may allow for delivery of a compound of Formula A-D-Y, or a pharmaceutically acceptable salt, solvate, hydrate, cocrystal, or prodrug thereof, to anterior segments of the eye following topical administration.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of Formula A-D-Y, or a pharmaceutically acceptable salt, solvate, hydrate, cocrystal, or prodrug thereof, a pharmaceutically acceptable carrier, and one or more of gellan gum, vitamin E TPGS, and a (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of Formula A-D-Y, or a pharmaceutically acceptable salt, solvate, hydrate, cocrystal, or prodrug thereof, a pharmaceutically acceptable carrier, and one or more of about 0% to about 5% gellan gum, about 0% to about 20% vitamin E TPGS, and about 0% to about 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of Formula A-D-Y, or a pharmaceutically acceptable salt, solvate, hydrate, cocrystal, or prodrug thereof, a pharmaceutically acceptable carrier, and one or more of greater than 0.1% gellan gum, greater than 1% vitamin E TPGS, and greater than 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, less than 20% of a compound of Formula A-D-Y, or a pharmaceutically acceptable salt, solvate, hydrate, cocrystal, or prodrug thereof, a pharmaceutically acceptable carrier, and one or more of less than 5% gellan gum, less than 20% vitamin E TPGS, less than 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 2.4% to about 3% of a compound of Formula A-D-Y, or a pharmaceutically acceptable salt, solvate, hydrate, cocrystal, or prodrug thereof, a pharmaceutically acceptable carrier, and one or more of about 0.5% gellan gum, about 5% vitamin E TPGS, about 10% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 2.4% to about 3% of a compound of Formula A-D-Y, or a pharmaceutically acceptable salt, solvate, hydrate, cocrystal, or prodrug thereof, a pharmaceutically acceptable carrier, and one or more of about 0.4% gellan gum, about 10% vitamin E TPGS, about 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of Formula A-D-Y, or a pharmaceutically acceptable salt, solvate, hydrate, cocrystal, or prodrug thereof, a pharmaceutically acceptable carrier, and one or more of sodium alginate, vitamin E TPGS, a (2-hydroxypropyl)-β-cyclodextrin, Tween, e.g., Tween 80, poly(ethylene glycol) (PEG), e.g., PEG 400, and polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of Formula A-D-Y, or a pharmaceutically acceptable salt, solvate, hydrate, cocrystal, or prodrug thereof, a pharmaceutically acceptable carrier, and one or more of about 0% to about 5% sodium alginate, about 0% to about 20% vitamin E TPGS, and about 0% to about 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of Formula A-D-Y, or a pharmaceutically acceptable salt, solvate, hydrate, cocrystal, or prodrug thereof, a pharmaceutically acceptable carrier, and one or more of greater than 0.1% sodium alginate, greater than 1% vitamin E TPGS, and greater than 5% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of Formula A-D-Y, or a pharmaceutically acceptable salt, solvate, hydrate, cocrystal, or prodrug thereof, a pharmaceutically acceptable carrier, and one or more of less than 5% sodium alginate, less than 20% vitamin E TPGS, less than 20% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 3% of a compound of Formula A-D-Y, or a pharmaceutically acceptable salt, solvate, hydrate, cocrystal, or prodrug thereof, a pharmaceutically acceptable carrier, and one or more of about 1.5% sodium alginate, about 5% vitamin E TPGS, about 10% (2-hydroxypropyl)-β-cyclodextrin.

In an embodiment, the invention includes a composition for treating an ophthalmic condition in a patient in need thereof, wherein the ophthalmic condition is selected from the group consisting of dry eye disease and retinopathy, the composition comprising, by weight, about 0.5% to about 10% of a compound of Formula A-D-Y, or a pharmaceutically acceptable salt, solvate, hydrate, cocrystal, or prodrug thereof, a pharmaceutically acceptable carrier, and one or more of about 0% to about 5% sodium alginate, about 0% to about 25% Tween 80, about 0% to about 20% (2-hydroxypropyl)-β-cyclodextrin, about 0% to about 20% PEG 400, and about 0% to about 10% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, greater than 0.5% of a compound of Formula A-D-Y, or a pharmaceutically acceptable salt, solvate, hydrate, cocrystal, or prodrug thereof, a pharmaceutically acceptable carrier, and one or more of greater than 1% sodium alginate, greater than 1% Tween 80, greater than 1% (2-hydroxypropyl)-β-cyclodextrin, greater than 1% PEG 400, and greater than 1% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of Formula A-D-Y, or a pharmaceutically acceptable salt, solvate, hydrate, cocrystal, or prodrug thereof, a pharmaceutically acceptable carrier, and one or more of less than 5% sodium alginate, less than 25% Tween 80, less than 20% (2-hydroxypropyl)-β-cyclodextrin, less than 20% PEG 400, and less than 10% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, about 3% of a compound of Formula A-D-Y, or a pharmaceutically acceptable salt, solvate, hydrate, cocrystal, or prodrug thereof, a pharmaceutically acceptable carrier, and one or more of about 1.5% sodium alginate, about 15% Tween 80, about 10% (2-hydroxypropyl)-β-cyclodextrin, about 10% PEG 400, and about 5% polyoxyl stearate.

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of Formula A-D-Y, or a pharmaceutically acceptable salt, solvate, hydrate, cocrystal, or prodrug thereof, a pharmaceutically acceptable carrier, and one or more of about 50% to about 90% (2-hydroxypropyl)-β- cyclodextrin (HP-β-CD), about 0.05% to about 1% cremophor EL (F1), and about 0.5% to about 5% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of Formula A-D-Y, or a pharmaceutically acceptable salt, solvate, hydrate, cocrystal, or prodrug thereof, a pharmaceutically acceptable carrier, and one or more of about 50% to about 90% (2-hydroxypropyl)-β-cyclodextrin (HP-β-CD), and about 0.05% to about 1% cremophor EL (F1).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 5% of a compound of Formula A-D-Y, or a pharmaceutically acceptable salt, solvate, hydrate, cocrystal, or prodrug thereof, a pharmaceutically acceptable carrier, and one or more of about 50% to about 90% (2-hydroxypropyl)-β-cyclodextrin (HP-β-CD), and about 0.5% to about 5% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 3% to about 4% of a compound of Formula A-D-Y, or a pharmaceutically acceptable salt, solvate, hydrate, cocrystal, or prodrug thereof, a pharmaceutically acceptable carrier, and one or more of about 80% (2-hydroxypropyl)-β-cyclodextrin (HP-β-CD), and about 0.1% cremophor EL (F1).

In an embodiment, the invention includes a composition for treating an ophthalmic condition in a patient in need thereof, wherein the ophthalmic condition is selected from the group consisting of dry eye disease and retinopathy, the composition comprising, by weight, about 3% to about 4% of a compound of Formula A-D-Y, or a pharmaceutically acceptable salt, solvate, hydrate, cocrystal, or prodrug thereof, a pharmaceutically acceptable carrier, and one or more of about 80% (2-hydroxypropyl)-β-cyclodextrin (HP-β-CD), and about 1% Tween 80 (F2).

In an embodiment, the invention includes a composition for treating an ophthalmic condition in a patient in need thereof, wherein the ophthalmic condition is selected from the group consisting of dry eye disease and retinopathy, the composition comprising, by weight, about 1% to about 10% of a compound of Formula A-D-Y, or a pharmaceutically acceptable salt, solvate, hydrate, cocrystal, or prodrug thereof, a pharmaceutically acceptable carrier, and one or more of about 1% to about 40% Poloxamer 407 and about 1% to about 20% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, greater than 1% of a compound of Formula A-D-Y, or a pharmaceutically acceptable salt, solvate, hydrate, cocrystal, or prodrug thereof, a pharmaceutically acceptable carrier, and one or more of greater than 1% Poloxamer 407 and greater than 1% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, less than 10% of a compound of Formula A-D-Y, or a pharmaceutically acceptable salt, solvate, hydrate, cocrystal, or prodrug thereof, a pharmaceutically acceptable carrier, and one or more of less than 40% Poloxamer 407 and less than 20% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising, by weight, about 5.4% of a compound of Formula A-D-Y, or a pharmaceutically acceptable salt, solvate, hydrate, cocrystal, or prodrug thereof, a pharmaceutically acceptable carrier, and one or more of about 20% Poloxamer 407, and about 12% vitamin E TPGS.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising a compound of Formula A-D-Y, or a pharmaceutically acceptable salt, solvate, hydrate, cocrystal, or prodrug thereof, and a pharmaceutically acceptable carrier. In some embodiments, the nanoparticle formulation may include poly(ethylene glycol) (PEG) nanoparticles. In some embodiments, the nanoparticle formulation may include methoxy poly(ethylene glycol)-poly(lactide) (mPEG-PLA) nanoparticles. In some embodiments, such formulations may allow for delivery of a compound of Formula A-D-Y, or a pharmaceutically acceptable salt, solvate, hydrate, cocrystal, or prodrug thereof, to anterior segments of the eye following topical administration.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising, by weight, about 1% to about 5% of a compound of Formula A-D-Y, or a pharmaceutically acceptable salt, solvate, hydrate, cocrystal, or prodrug thereof, a pharmaceutically acceptable carrier, and about 90% to about 98% mPEG-PLA.

In an embodiment, the invention includes a composition for treating an ophthalmic condition in a patient in need thereof, wherein the ophthalmic condition is selected from the group consisting of dry eye disease and retinopathy, the composition comprising a nanoparticle formulation comprising, by weight, about 3% to about 3.5% of a compound of Formula A-D-Y, or a pharmaceutically acceptable salt, solvate, hydrate, cocrystal, or prodrug thereof, a pharmaceutically acceptable carrier, and about 96.5% to about 97% mPEG-PLA.

In some embodiments, the compounds of Formula A-D-Y, or pharmaceutically acceptable salts, solvates, hydrates, cocrystals, or prodrugs thereof, are analgesic agents.

In some embodiments, the compounds of Formula A-D-Y, or pharmaceutically acceptable salts, solvates, hydrates, cocrystals, or prodrugs thereof, are anti-inflammatory agents.

In some embodiments, the compounds of Formula A-D-Y, or pharmaceutically acceptable salts, solvates, hydrates, cocrystals, or prodrugs thereof, have a reduced risk of corneal melt or do not result in corneal melt upon administration to the eye.

BRIEF DESCRIPTION OF THE DRAWINGS

The foregoing summary, as well as the following detailed description of embodiments of the invention, will be better understood when read in conjunction with the appended drawings and figures.

FIG. 12A: Left: Compound 5 increases the percentage of cells with acridine orange staining determined by flow cytometry (4%-38% after treatment with compound 5) and indicating the induction of autophagy. Right: Electron micrographs show morphological features of cells undergoing autophagy. Yellow arrowheads: vacuoles; white arrowheads: autophagosomes. FIG. 12B: Transmission electron microscopy establishes the induction of endoplasmic reticulum (ER) stress by compound 5. N: nucleus; ER: endoplasmic reticulum with visible ribosomes. The left micrograph shown normal ER (circled) in a vehicle-treated cell. The right one shows greatly dilated ER lumen (arrows) in a cell treated with compound 5 1.5×IC$_{50}$. The latter finding is diagnostic of ER stress. Magnification: 6,800×. FIG. 12C: Compound 5 suppresses STAT3, mTOR and JNK activation by phosphorylation, as well as the levels of COT.

FIG. 13A: Compound 5 induces the phosphorylation of eIF2α, confirming integrated stress response. p-eIF2α induces ATF4 that suppresses 5'-cap dependent translation initiation, shown below. FIG. 13B: Compound 5 suppresses predominantly 5'-cap dependent translation initiation. The levels of reporter proteins used in the translation assay (Pierce™ Renilla-Firefly Luciferase Dual Assay Kit; Thermo Scientific, Grand Island, N.Y.) were normalized to the levels of intracellular FLUC-RLUC transcripts and are shown as percent of untreated control cells. RLU=Relative light units. 5'-cap dependent translation initiation was much less and occurred later. Values: Mean±SEM; *, $p<0.05$ and , $p<0.01$ vs. control. FIG. 13C**: Compound 5 1.5×IC$_{50}$ activated by phosphorylation PERK and GCN2. Loading controls: β-actin and GADPH.

FIGS. 15A-15E illustrate key findings related to the mechanism of action of compound 6 against ovarian cancer. The studies shown here were performed in SKOV-3 human ovarian cancer cells. FIG. 15A: Strong induction of mitochondrial superoxide anion detected with the MitoSox Red molecular probe, using flow cytometry. TTFA, a mitochondrial ROS blocker, reversed the effect of compound 6 (C6). FIG. 15B. Compound 6 suppressed the levels of GSH, the main cytosolic chemical antioxidant, in cells treated for 3 hours (*$p<0.01$). FIG. 15C. The levels of Prx-1 and Prx-SO$_3$ in cells treated with compound 6 for 24 hours (immunoblotting). FIG. 15D. Compound 6 concentration-dependently suppressed the enzymatic activity of TrxR after 1 hour of treatment (*$p<0.01$). FIG. 15E. Protein lysates of cells treated with compound 6 for 1 h with or without DTT 1 mM for 30 min and to immunoprecipitation (IP) immunoblotting (IB) as shown. Loading control: Trx-1.

FIG. 18 illustrates the effect of compounds 5 and 6 on K-Ras.

FIG. 19 illustrates the normalization of retinal vasculature by compound 6 in a model of oxygen-induced retinopathy in mice. FIG. 19A: Retinal flat mounts from C57Bl/6 mice at postnatal day 17 (P17) under oxygen-induced retinopathy conditions stained with isolectin B4 to label the vasculature. Vehicle treated mice (left) show the central avascular area (blue arrow) and the peripheral neovascularization (red arrow). Compound 6 (right) normalized both. FIG. 19B: Quantification of the avascular and neovascular areas of the retina, expressed as percentage of the entire retina surface area.

FIG. 21 illustrates the normalization of retinal vasculature by compound 2 in a mouse model of oxygen-induced retinopathy.

DETAILED DESCRIPTION OF THE INVENTION

Figure 1:
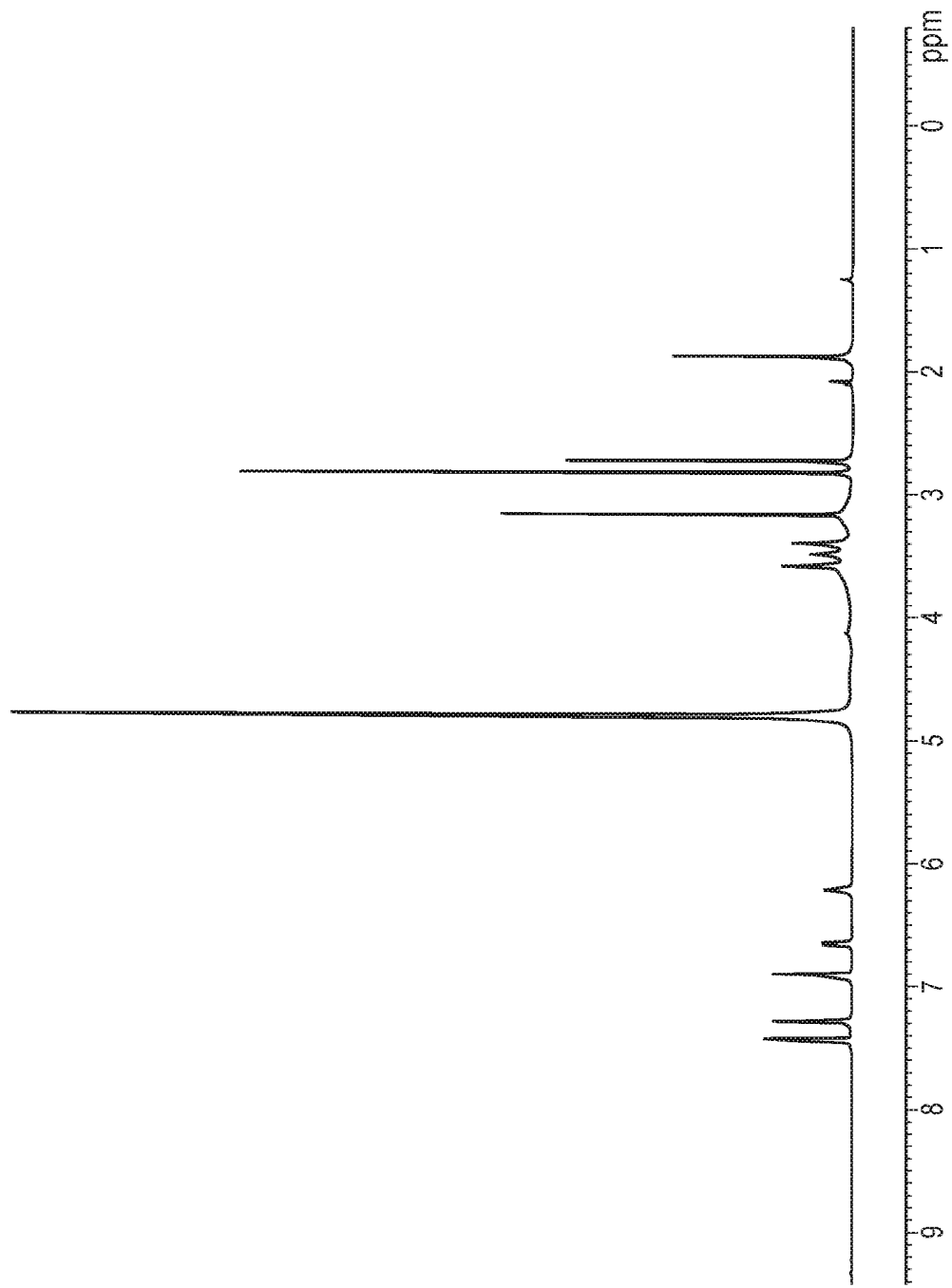
FIG. 1 illustrates the $^1$HNMR spectra of compound 1 salt.

Unless defined otherwise, all technical and scientific terms used herein have the same meaning as is commonly understood by one of skill in the art to which this invention belongs. All patents and publications referred to herein are incorporated by reference in their entireties.

Definitions

As used herein, the terms "administer," "administration," or "administering" refer to (1) providing, giving, dosing, and/or prescribing by either a health practitioner or his authorized agent or under his or her direction according to the disclosure, and/or (2) putting into, taking, or consuming by a subject, for example a mammal, including a human, according to the disclosure.

The terms "co-administration," "co-administering," "administered in combination with," "administering in combination with," "simultaneous," and "concurrent," as used herein, encompass administration of two or more active pharmaceutical ingredients to a subject so that both active pharmaceutical ingredients and/or their metabolites are present in the subject at the same time. Co-administration includes simultaneous administration in separate compositions, administration at different times in separate compositions, or administration in a composition in which two or more active pharmaceutical ingredients are present. In some embodiments, simultaneous administration in separate compositions and administration in a composition in which both agents are present are preferred.

The terms "active pharmaceutical ingredient" and "drug" include the compound of Formula A-D-Y, including, but not limited to, all examples described herein.

The term "isostere" refers to a group or molecule whose chemical and/or physical properties are similar to those of another group or molecule. A "bioisostere" is a type of isostere and refers to a group or molecule whose biological properties are similar to those of another group or molecule. For example, for the compound of Formula A-D-Y described herein, a carboxylic acid may be replaced by one of the following bioisosteres for carboxylic acids, including, without limitation, alkyl esters (COOR), acylsulfonamides (CONR—SO$_2$R), hydroxamic acids (CONR—OH), hydroxamates (CONR—OR), tetrazoles, hydroxyisoxazoles, isoxazol-3-ones, and sulfonamides (SO$_2$NR), where each R may independently represent hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, etc., which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit. A prophylactic effect includes delaying or eliminating the appearance of a disease or condition, delaying or eliminating the onset of symptoms of a disease or condition, slowing, halting, or reversing the progression of a disease or condition, preventing its recurrence, or any combination thereof.

As used herein, the terms "treat," "treatment," and/or "treating" may refer to the management of a disease, disorder, or pathological condition, or symptom thereof with the intent to cure, ameliorate, stabilize, and/or control the disease, disorder, pathological condition or symptom thereof. Regarding control of the disease, disorder, or pathological condition more specifically, "control" may include the absence of condition progression, as assessed by the response to the methods recited herein, where such response may be complete (e.g., placing the disease in remission) or partial (e.g., lessening or ameliorating any symptoms associated with the condition). As used herein, the terms "prevent," "preventing," and/or "prevention" may refer to reducing the risk of developing a disease, disorder, or pathological condition.

As used herein, the terms "modulate" and "modulation" refer to a change in biological activity for a biological molecule (e.g., a protein, gene, peptide, antibody, and the like), where such change may relate to an increase in biological activity (e.g., increased activity, agonism, activation, expression, upregulation, and/or increased expression) or decrease in biological activity (e.g., decreased activity, antagonism, suppression, deactivation, downregulation, and/or decreased expression) for the biological molecule. Without being limited by any particular theory, the compounds described herein may, for example, modulate (i.e., inhibit) VEGF expression, and/or K-Ras expression.

The terms "QD," "qd," or "q.d." mean quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "pharmaceutically acceptable salt" refers to salts derived from a variety of organic and inorganic counter ions known in the art. Pharmaceutically acceptable acid addition salts can be formed with inorganic acids and organic acids. Preferred inorganic acids from which salts can be derived include, for example, hydrochloric acid, hydrobromic acid, sulfuric acid, nitric acid and phosphoric acid. Preferred organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic, phosphoric acid, acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve hydrogen transfer between the cocrystal and the drug, and instead involves intermolecular interactions, such as hydrogen bonding, aromatic ring stacking, or dispersive forces, between the cocrystal former and the drug in the crystal structure.

"Pharmaceutically acceptable carrier" or "pharmaceutically acceptable excipient" or "physiologically compatible" carrier or carrier medium is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically acceptable carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

A "prodrug" refers to a derivative of a compound described herein, the pharmacologic action of which results from the conversion by chemical or metabolic processes in vivo to the active compound. Prodrugs include compounds wherein an amino acid residue, or a polypeptide chain of two or more (e.g., two, three or four) amino acid residues is covalently joined through an amide or ester bond to a free amino, hydroxyl or carboxylic acid group of Formula A-D-Y. The amino acid residues include but are not limited to the 20 naturally occurring amino acids commonly designated by one or three letter symbols but also include, for example, 4-hydroxyproline, hydroxylysine, desmosine, isodesmosine, 3-methylhistidine, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters (e.g., methyl esters and acetoxy methyl esters). Prodrug esters as employed herein includes esters and carbonates formed by reacting one or more hydroxyls of compounds of the method of the invention with alkyl, alkoxy, or aryl substituted acylating agents employing procedures known to those skilled in the art to generate acetates, pivalates, methylcarbonates, benzoates and the like. As further examples, free hydroxyl groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxyl and amino groups are also included, as are carbonate prodrugs, sulfonate prodrugs, sulfonate esters and sulfate esters of hydroxyl groups. Free amines can also be derivatized to amides, sulfonamides or phosphonamides. All of the stated prodrug moieties may incorporate groups including but not limited to ether, amine and carboxylic acid functionalities. Moreover, any compound that can be converted in vivo to provide the bioactive agent, e.g., a compound of Formula A-D-Y, is a prodrug within the scope of the invention. Various forms of prodrugs are well known in the art. A comprehensive description of pro drugs and prodrug derivatives are described in: (a) The Practice of Medicinal Chemistry, Camille G. Wermuth et al., (Academic Press, 1996); (b) Design of Prodrugs, edited by H. Bundgaard, (Elsevier, 1985); (c) A Textbook of Drug Design and Development, P. Krogsgaard-Larson and H. Bundgaard, eds., (Harwood Academic Publishers, 1991). In general, prodrugs may be designed to improve the penetration of a drug across biological membranes in order to obtain improved drug absorption, to prolong duration of action of a drug (slow release of the parent drug from a prodrug, decreased first-pass metabolism of the drug), to target the drug action (e.g., organ or tumor-targeting, lymphocyte targeting), to modify or improve aqueous solubility of a drug (e.g., i.v. preparations and eyedrops), to improve topical drug delivery (e.g., dermal and ocular drug delivery), to improve the chemical/enzymatic stability of a drug, or to decrease off-target drug effects, and more generally in order to improve the therapeutic efficacy of the compounds utilized in the invention.

Unless otherwise stated, the chemical structures depicted herein are intended to include compounds which differ only in the presence of one or more isotopically enriched atoms. For example, compounds where one or more hydrogen atoms is replaced by deuterium or tritium, or wherein one or more carbon atoms is replaced by $^{13}$C-enriched or $^{14}$C-enriched carbons, are within the scope of this invention.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5%, or the like, of the stated number or numerical range.

As used herein, the term "about" means that amounts, sizes, formulations, parameters, shapes and other quantities and characteristics are not, and need not be exact, but may be approximate and/or larger or smaller, as desired, reflecting tolerances, conversion factors, rounding off, measurement error and the like, and other factors known to those of skill in the art. In general, an amount, size, formulation, parameter, shape or other quantity or characteristic is "about" or "approximate" whether or not expressly stated to be such.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All compounds, compositions, formulations, and methods described herein that embody the present invention can, in alternate embodiments, be more specifically defined by any of the transitional terms "comprising," "consisting essentially of," and "consisting of." The term "comprising" (and related terms such as "comprise" or "comprises" or "having" or "including") includes those embodiments such as, for example, an embodiment of any composition of matter, method, or process that "consist of" or "consist essentially of" the described features.

"Alkyl" refers to a straight or branched hydrocarbon chain radical consisting solely of carbon and hydrogen atoms, containing no unsaturation, having from one to ten carbon atoms (e.g., $(C_{1-10})$alkyl or $C_{1-10}$ alkyl). Whenever it appears herein, a numerical range such as "1 to 10" refers to each integer in the given range, e.g., "1 to 10 carbon atoms" means that the alkyl group may consist of 1 carbon atom, 2 carbon atoms, 3 carbon atoms, etc., up to and including 10 carbon atoms, although the definition is also intended to cover the occurrence of the term "alkyl" where no numerical range is specifically designated. Typical alkyl groups include, but are in no way limited to, methyl, ethyl, propyl, isopropyl, n-butyl, isobutyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of substituents which are independently heteroalkyl, acylsulfonamido, alkenyl, alkynyl, cycloalkyl, heterocloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl) heterocyclic radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond, and an "alkyne" moiety refers to a group consisting of at least two carbon atoms and at least one carbon-carbon triple bond. The alkyl moiety, whether saturated or unsaturated, may be branched, straight chain, or cyclic.

"Alkenyl" refers to a straight or branched hydrocarbon chain radical group consisting solely of carbon and hydrogen atoms, containing at least one double bond, and having from two to ten carbon atoms (i.e., $(C_{2-10}$alkenyl or $C_{2-10}$ alkenyl). Whenever it appears herein, a numerical range such as "2 to 10" refers to each integer in the given range—e.g., "2 to 10 carbon atoms" means that the alkenyl group may consist of 2 carbon atoms, 3 carbon atoms, etc., up to and including 10 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl. Unless stated otherwise specifically in the specification, an alkenyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cycloalkyl are as disclosed herein and which are optionally substituted by one or more of the substituents described as suitable substituents for alkenyl and cycloalkyl respectively.

"Alkynyl" refers to a straight or branched hydrocarbon chain radical group consisting solely of carbon and hydrogen atoms, containing at least one triple bond, having from two to ten carbon atoms (i.e., $C_{2-10}$ alkynyl or $C_{2-10}$ alkynyl). Whenever it appears herein, a numerical range such as "2 to 10" refers to each integer in the given range—e.g., "2 to 10 carbon atoms" means that the alkynyl group may consist of 2 carbon atoms, 3 carbon atoms, etc., up to and including 10 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents which independently are: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Acylsulfonamide" refers to the group —C(=O)NR$^a$—S(=O)R$^a$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl, or heteroarylalkyl.

"Carboxaldehyde" refers to a —(C=O)H radical.

"Carbonyl" refers to the group —C(=O)—. Carbonyl groups may be substituted with the following exemplary substituents: alkyl, heteroalkyl, alkenyl, alkynyl, cycloalkyl, heterocycloalkyl, hydroxamate, acylsulfonamido, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —NR$^a$—OR$^a$—, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Carboxyl" refers to a —(C=O)OH radical.

"Cyano" refers to a —CN radical.

"Cycloalkyl" refers to a monocyclic or polycyclic radical that contains only carbon and hydrogen, and may be saturated, or partially unsaturated. Cycloalkyl groups include groups having from 3 to 10 ring atoms (i.e., $C_{3-10}$ cycloalkyl or $C_{3-10}$ cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like. Unless stated otherwise specifically in the specification, a cycloalkyl group is optionally substituted by one or more substituents which independently are: alkyl, heteroalkyl, alkenyl, alkynyl, cycloalkyl, acylsulfonamido, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl, including from 1 to 8 carbon atoms of a straight, branched, cyclic configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently are: alkyl, heteroalkyl, alkenyl, acylsulfonamido, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "alkoxycarbonyl" refers to a group of the formula (alkoxy)(C═O)— attached through the carbonyl carbon wherein the alkoxy group has the indicated number of carbon atoms. Thus a (C$_{1-6}$)alkoxycarbonyl group is an alkoxy group having from 1 to 6 carbon atoms attached through its oxygen to a carbonyl linker. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which independently are: alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyl" refers to the groups (alkyl)-C(O)—, (aryl)-C(O)—, (heteroaryl)-C(O)—, (heteroalkyl)-C(O)— and (heterocycloalkyl)-C(O)—, wherein the group is attached to the parent structure through the carbonyl functionality. If the R radical is heteroaryl or heterocycloalkyl, the hetero ring or chain atoms contribute to the total number of chain or ring atoms. Unless stated otherwise specifically in the specification, the alkyl, aryl or heteroaryl moiety of the acyl group is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Acyloxy" refers to a R(C═O)O— radical wherein R is alkyl, aryl, heteroaryl, heteroalkyl or heterocycloalkyl, which are as described herein. If the R radical is heteroaryl or heterocycloalkyl, the hetero ring or chain atoms contribute to the total number of chain or ring atoms. Unless stated otherwise specifically in the specification, the R of an acyloxy group is optionally substituted by one or more substituents which independently are: alkyl, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ substituents other than hydrogen, they can be combined with the nitrogen atom to form a 4-, 5-, 6- or 7-membered ring. For example, —N(R$^a$)$_2$ is intended to include, but is not limited to, 1-pyrrolidinyl and 4-morpholinyl. Unless stated otherwise specifically in the specification, an amino group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)NR$^a$R$^b$ or —NR$^a$C(O)R$^b$, where R$^a$ and R$^b$ are selected from the group consisting of hydrogen, alkyl, cycloalkyl, aryl, heteroaryl (bonded through a ring carbon) and heteroalicyclic (bonded through a ring carbon), each of which moiety may itself be optionally substituted. The R$^a$ and R$^b$ of —C(O)NR$^a$R$^b$ amide may optionally be taken together with the nitrogen to which they are attached to form a 4-, 5-, 6- or 7-membered ring. Unless stated otherwise specifically in the specification, an amido group is optionally substituted independently by one or more of the substituents as described herein for alkyl, amino, cycloalkyl, aryl, heteroaryl, or heterocycloalkyl. An amide may be an amino acid or a peptide molecule attached to a compound disclosed herein, thereby forming a prodrug. The procedures and specific groups to make such amides are known to those of skill in the art and can readily be found in seminal sources such as Greene and Wuts, *Protective Groups in Organic Synthesis*, 3$^{rd}$ Ed., John Wiley & Sons, New York, N.Y., 1999, which is incorporated herein by reference in its entirety.

"Aromatic" or "aryl" or "Ar" refers to an aromatic radical with six to ten ring atoms (e.g., C$_6$-C$_{10}$ aromatic or C$_6$-C$_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range, e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are independently alkyl, heteroalkyl, acylsulfonamido, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COOR, where R is selected from the group consisting of alkyl, cycloalkyl, aryl, heteroaryl (bonded through a ring carbon) and heteroalicyclic (bonded through a ring carbon). The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

"Halo," "halide," or, alternatively, "halogen" is intended to mean fluoro, chloro, bromo or iodo. The terms "haloalkyl," "haloalkenyl," "haloalkynyl," and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl," "heteroalkenyl," and "heteroalkynyl" refer to optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., C$_1$-C$_4$ heteroalkyl which refers to the chain length in total, which in this example is 4 atoms long. A heteroalkyl group may be substituted with one or more substituents which independently are: alkyl, heteroalkyl, alkenyl, alkynyl, acylsulfonamido, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic" or "HetAr" refers to a 5- to 18-membered aromatic radical (e.g., C$_5$-C$_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. A N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, isoxazol-3-one, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Substituted heteroaryl also includes ring systems substituted with one or more oxide (—O—) substituents, such as, for example, pyridinyl N-oxides.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, a heterocycloalkyl moiety is optionally substituted by one or more substituents which independently are: alkyl, acylsulfonamido, heteroalkyl, alkenyl, alkynyl, cycloalkyl, heterocycloalkyl, hydroxamate, aryl, arylalkyl, heteroaryl, heteroarylalkyl, hydroxy, halo, cyano, nitro, oxo, thioxo, trimethylsilanyl, —OR$^a$, —SR$^a$, —S(O)$_t$R$^a$— (where t is 1 or 2), —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms, and the other ring, usually with 3 to 7 ring atoms, optionally contains 1-3 heteroatoms independently selected from oxygen, sulfur, and nitrogen and is not aromatic.

"Hydroxamate" refers to the —C(O)NR$^a$OR$^a$ moiety, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Nitro" refers to the —NO$_2$ radical.

"Oxa" refers to the —O— radical.

"Oxo" refers to the =O radical.

"Isomers" are different compounds that have the same molecular formula.

"Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In some embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts, or preferred enantiomers can be prepared by asymmetric syntheses. See, for example, Jacques, et al., *Enantiomers, Racemates and Resolutions*, Wiley Interscience, New York (1981); E. L. Eliel, *Stereochemistry of Carbon Compounds*, McGraw-Hill, New York (1962); and E. L. Eliel and S. H. Wilen, *Stereochemistry of Organic Compounds*, Wiley-Interscience, New York (1994).

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g., in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in T. H. Greene and P. G. M. Wuts, *Protective Groups in Organic Synthesis*, 3rd Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxamate, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O₂)—H, —S(O₂)-(optionally substituted alkyl), —S(O₂)-(optionally substituted amino), —S(O₂)-(optionally substituted aryl), —S(O₂)-(optionally substituted heteroaryl), and —S(O₂)-(optionally substituted heterocycloalkyl).

"Sulfonamidyl" or "sulfonamido" refers to a —S(=O)₂—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —S(=O)₂—NRR radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)₂OH radical.

"Sulfonate" refers to a —S(=O)₂—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

Compounds of the invention also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Compounds of Formula A-D-Y

This invention provides novel compounds that have biological properties useful for the treatment of any of a number of conditions or diseases generally characterized by abnormal inflammation, or prophylaxis in instances wherein a risk of appearance of such conditions or diseases is present.

In one embodiment, the invention relates to a compound of Formula A-D-Y, or a pharmaceutically acceptable salt, solvate, hydrate, cocrystal, or prodrug thereof. In some embodiments, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1.

TABLE 1

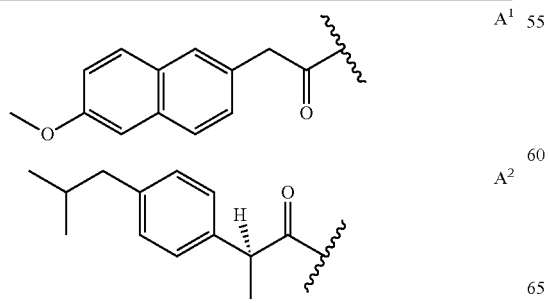

TABLE 1-continued

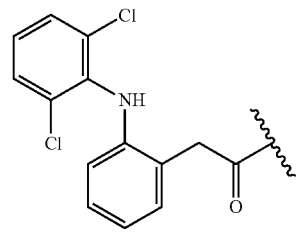 [SMILES: *C(=O)Cc1ccccc1Nc1c(Cl)cccc1Cl]

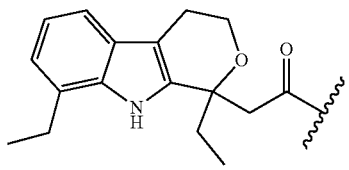 [SMILES: *C(=O)CC1(CC)OCCc2c1[nH]c1c(CC)cccc21]

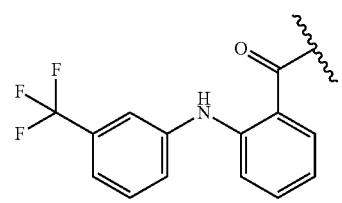 [SMILES: *C(=O)c1ccccc1Nc1cccc(C(F)(F)F)c1]

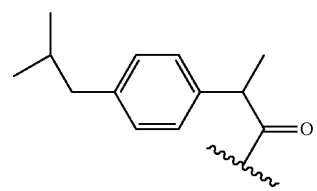 [SMILES: *C(=O)C(C)c1ccc(CC(C)C)cc1]

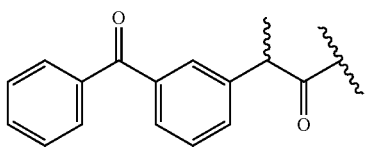 [SMILES: *C(=O)C(C)c1cccc(C(=O)c2ccccc2)c1]

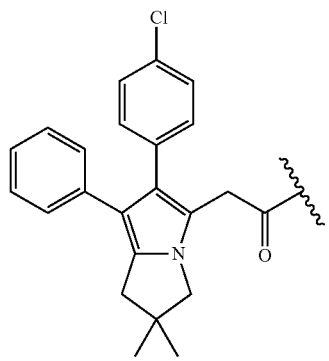 [SMILES: *C(=O)Cc1c(-c2ccc(Cl)cc2)c(-c2ccccc2)c2n1CC(C)(C)C2]

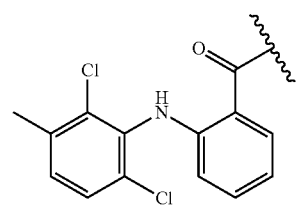 [SMILES: *C(=O)c1ccccc1Nc1c(Cl)ccc(C)c1Cl]

TABLE 1-continued
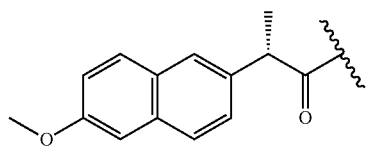 [SMILES: *C(=O)[C@@H](C)c1ccc2cc(OC)ccc2c1] A10
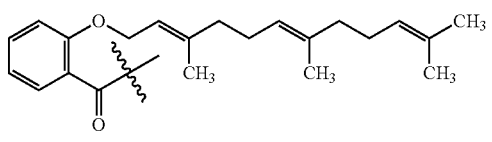 A17
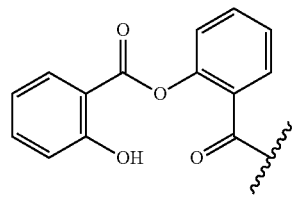 [SMILES: *C(=O)c1ccccc1OC(=O)c1ccccc1O] A11
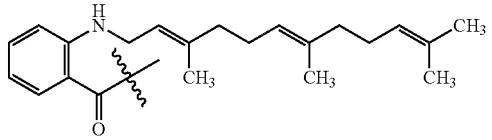 A18
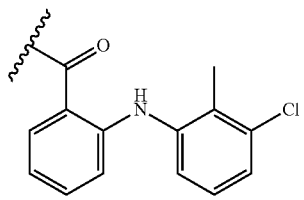 [SMILES: *C(=O)c1ccccc1Nc1cccc(Cl)c1C] A12
 A19
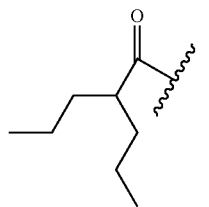 [SMILES: *C(=O)C(CCC)CCC] A13
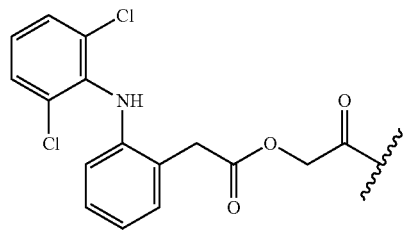 A20
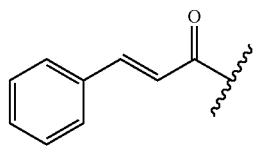 [SMILES: *C(=O)/C=C/c1ccccc1] A14
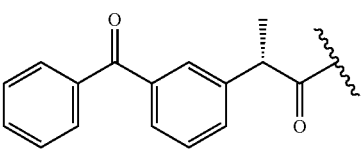 A21
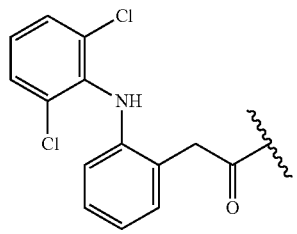 [SMILES: *C(=O)Cc1ccccc1Nc1c(Cl)cccc1Cl] A15
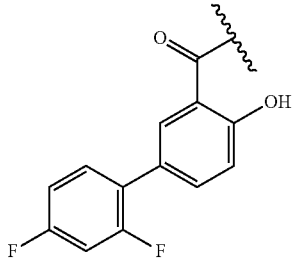 A22
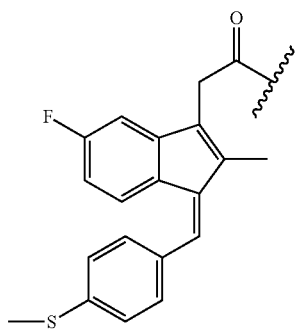 [SMILES: *C(=O)CC1=C(C)/C(=C/c2ccc(SC)cc2)c2ccc(F)cc21] A16
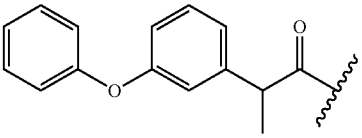 [SMILES: *C(=O)C(C)c1cccc(Oc2ccccc2)c1] A23
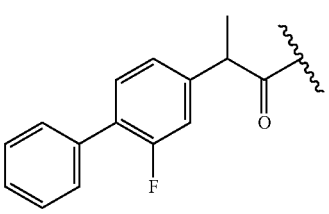 [SMILES: *C(=O)C(C)c1ccc(-c2ccccc2)c(F)c1] A24

TABLE 1-continued
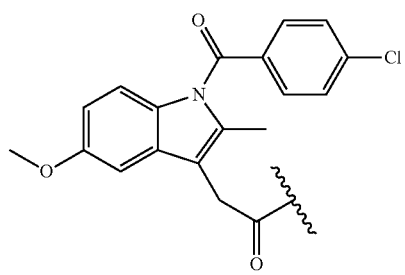 [SMILES: *C(=O)Cc1c(C)n(C(=O)c2ccc(Cl)cc2)c2ccc(OC)cc12] A25
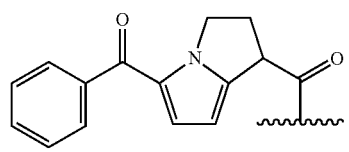 [SMILES: *C(=O)C1CCn2c(C(=O)c3ccccc3)ccc21] A26
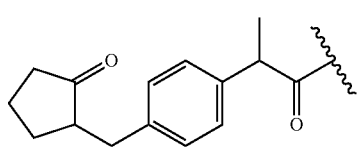 [SMILES: *C(=O)C(C)c1ccc(CC2CCCC2=O)cc1] A27
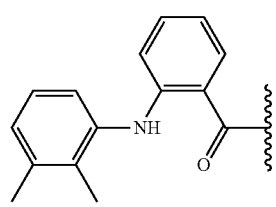 [SMILES: *C(=O)c1ccccc1Nc1cccc(C)c1C] A28
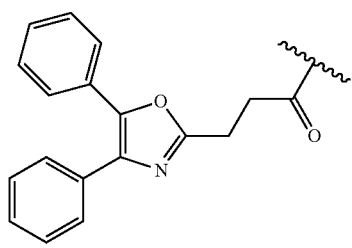 [SMILES: *C(=O)CCc1nc(-c2ccccc2)c(-c2ccccc2)o1] A29
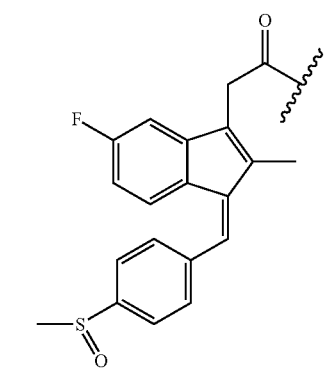 [SMILES: *C(=O)CC1=C(C)/C(=C/c2ccc(S(C)=O)cc2)c2ccc(F)cc21] A30
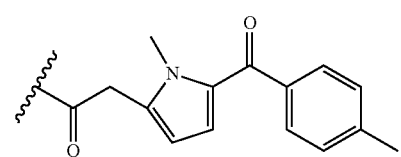 [SMILES: *C(=O)Cc1ccc(C(=O)c2ccc(C)cc2)n1C] A31
TABLE 1-continued
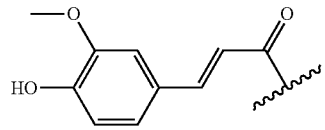 [SMILES: *C(=O)/C=C/c1ccc(O)c(OC)c1] A32
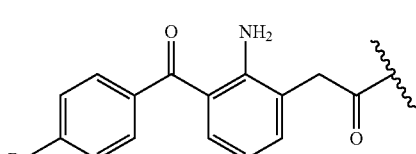 A33
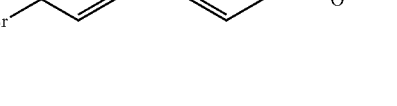 A34
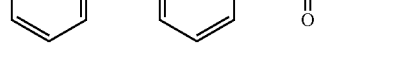 A35
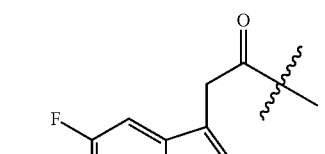 A35
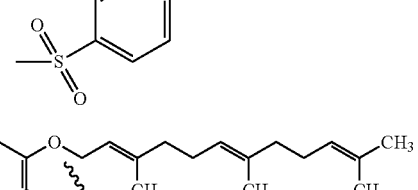 A36
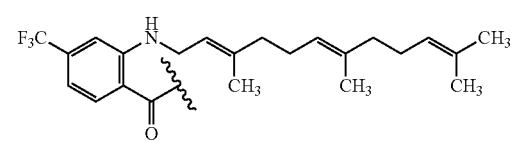 [SMILES: *C(=O)c1ccc(C(F)(F)F)cc1NC/C=C(\C)CC/C=C(\C)CCC=C(C)C] A37
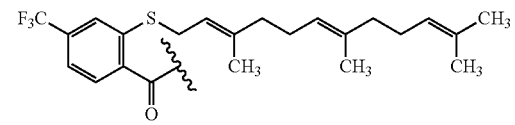 A38
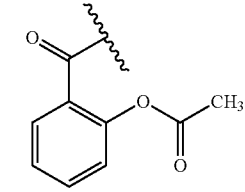 [SMILES: *C(=O)c1ccccc1OC(C)=O] A39

TABLE 1-continued

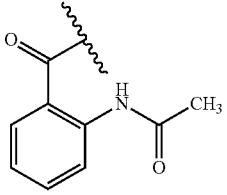 [SMILES: *C(=O)c1ccccc1NC(C)=O]
A⁴⁰

In one embodiment, the invention relates to a compound of Formula A-D-Y, or a pharmaceutically acceptable salt, solvate, hydrate, cocrystal, or prodrug thereof, wherein D is selected from the group consisting of $D^1$ to $D^9$ as defined in Table 2. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, and D is selected from the group consisting of $D^1$ to $D^9$ as defined in Table 2.

TABLE 2

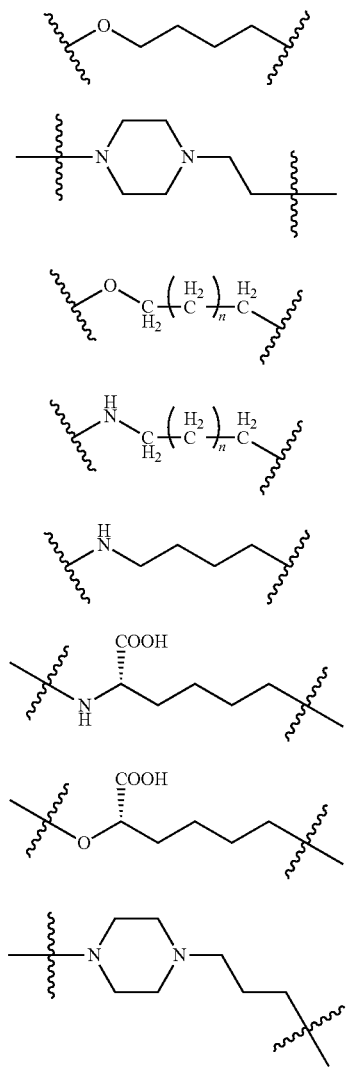

TABLE 2-continued

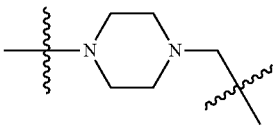 [SMILES: *CN1CCN(*)CC1]
D⁹ n is an integer between 0 and 12

In one embodiment, the invention relates to a compound of Formula A-D-Y, or a pharmaceutically acceptable salt, solvate, hydrate, cocrystal, or prodrug thereof, wherein Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, and Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein D is selected from the group consisting of $D^1$ to $D^9$ as defined in Table 2, and Y is selected from the group consisting of $Y^1$ to $Y^7$ as defined in Table 3. In one embodiment, the invention relates to a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1, D is selected from the group consisting of $D^1$ to $D^9$ as defined in Table 2, and Y is selected from the group consisting of $Y^1$ to $Y^7$ as defined in Table 3.

TABLE 3

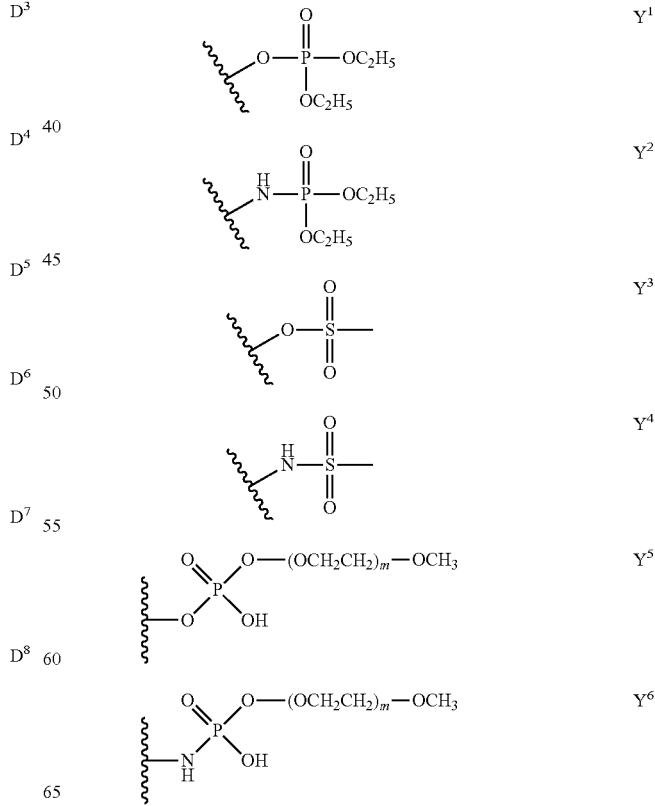

TABLE 3-continued

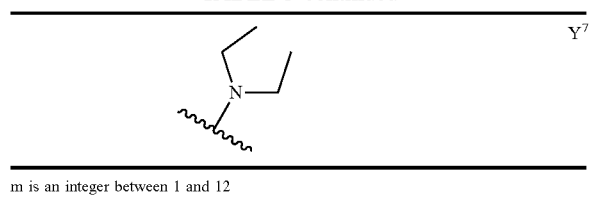

m is an integer between 1 and 12

In some embodiments, the invention relates to a compound of Formula A-D-Y, or a pharmaceutically acceptable salt, solvate, hydrate, cocrystal, or prodrug thereof, wherein the compound has anti-inflammatory, anticancer, or antiangiogenic effects.

In some embodiments, the invention relates to a pharmaceutical composition including a compound of Formula A-D-Y, or a pharmaceutically acceptable salt, solvate, hydrate, cocrystal, or prodrug thereof. In some embodiments, A is selected from the group consisting of $A^1$ to $A^{40}$ as defined in Table 1. In some embodiments, D is selected from the group consisting of $D^1$ to $D^9$ as defined in Table 2. In some embodiments, Y is selected from the group consisting of $Y^1$ to $Y^7$ as defined in Table 3.

In one embodiment, the invention relates to compound 1, or a pharmaceutically acceptable salt, solvate, hydrate, cocrystal, or prodrug thereof. In one embodiment, the invention relates to a pharmaceutical composition including compound 1, or a pharmaceutically acceptable salt, solvate, hydrate, cocrystal, or prodrug thereof, and a pharmaceutically acceptable excipient.

Compound 1

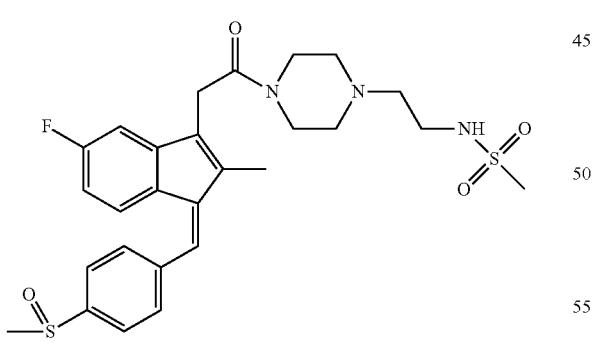

In one embodiment, the invention relates to compound 2, or a pharmaceutically acceptable salt, solvate, hydrate, cocrystal, or prodrug thereof. In one embodiment, the invention relates to a pharmaceutical composition including compound 2, or a pharmaceutically acceptable salt, solvate, hydrate, cocrystal, or prodrug thereof, and a pharmaceutically acceptable excipient.

Compound 2

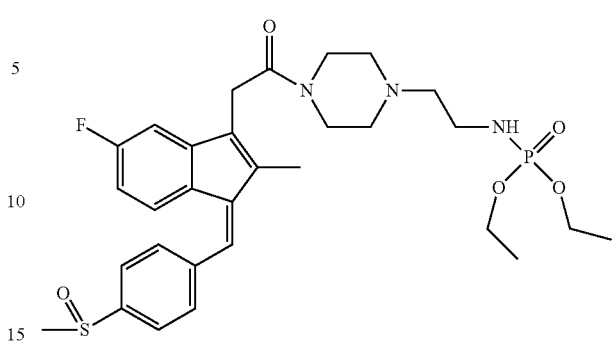

In one embodiment, the invention relates to compound 3, or a pharmaceutically acceptable salt, solvate, hydrate, cocrystal, or prodrug thereof. In one embodiment, the invention relates to a pharmaceutical composition including compound 3, or a pharmaceutically acceptable salt, solvate, hydrate, cocrystal, or prodrug thereof, and a pharmaceutically acceptable excipient.

Compound 3

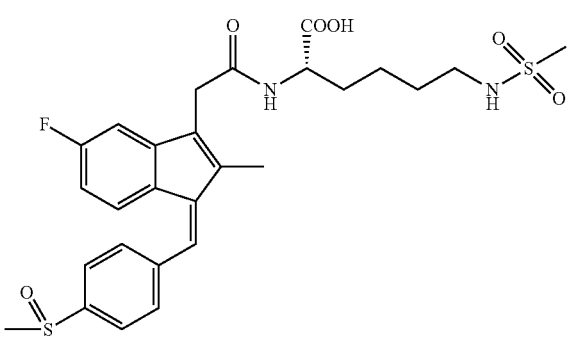

In one embodiment, the invention relates to compound 4, or a pharmaceutically acceptable salt, solvate, hydrate, cocrystal, or prodrug thereof. In one embodiment, the invention relates to a pharmaceutical composition including compound 4, or a pharmaceutically acceptable salt, solvate, hydrate, cocrystal, or prodrug thereof, and a pharmaceutically acceptable excipient.

Compound 4

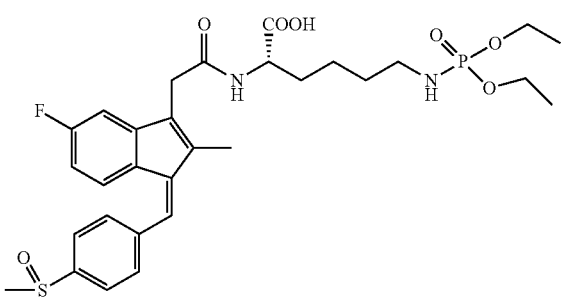

In one embodiment, the invention relates to compound 5, or a pharmaceutically acceptable salt, solvate, hydrate, cocrystal, or prodrug thereof. In one embodiment, the invention relates to a pharmaceutical composition including compound 5, or a pharmaceutically acceptable salt, solvate, hydrate, cocrystal, or prodrug thereof, and a pharmaceutically acceptable excipient.

Compound 5

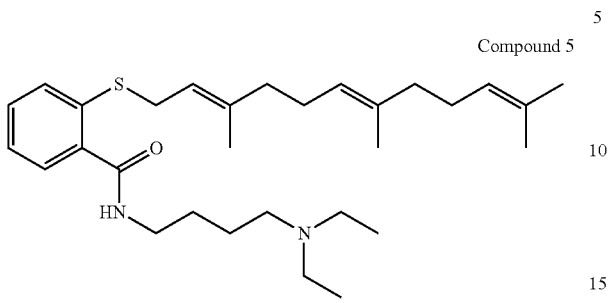

In one embodiment, the invention relates to compound 6, or a pharmaceutically acceptable salt, solvate, hydrate, cocrystal, or prodrug thereof. In one embodiment, the invention relates to a pharmaceutical composition including compound 6, or a pharmaceutically acceptable salt, solvate, hydrate, cocrystal, or prodrug thereof, and a pharmaceutically acceptable excipient.

Compound 6

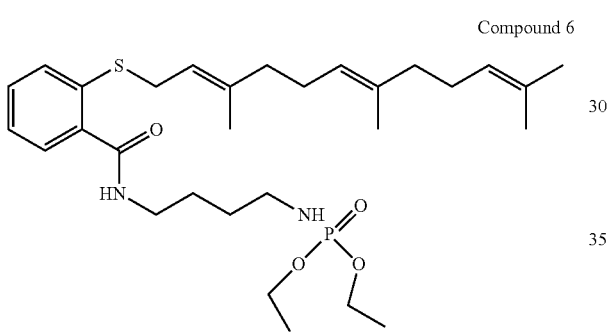

In one embodiment, the invention relates to compound 7, or a pharmaceutically acceptable salt, solvate, hydrate, cocrystal, or prodrug thereof. In one embodiment, the invention relates to a pharmaceutical composition including compound 7, or a pharmaceutically acceptable salt, solvate, hydrate, cocrystal, or prodrug thereof, and a pharmaceutically acceptable excipient.

Compound 7

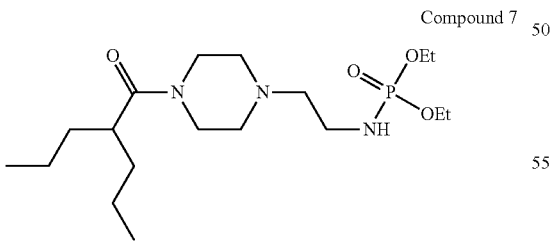

In some embodiments, the invention relates to compounds 10 to 107 as described in Table 4, or pharmaceutically acceptable salts, solvates, hydrates, cocrystals, or prodrugs thereof. In some embodiments, the invention relates to pharmaceutical compositions including one or more of compounds 10 to 107, or pharmaceutically acceptable salts, solvates, hydrates, cocrystals, or prodrugs thereof, and one or more pharmaceutically acceptable excipients.

TABLE 4

| | |
|---|---|
| 10 | A19-D1-Y1 |
| 11 | A19-D1-Y2 |
| 12 | A19-D1-Y3 |
| 13 | A19-D1-Y4 |
| 14 | A19-D1-Y5 |
| 15 | A19-D1-Y6 |
| 16 | A19-D1-Y7 |
| 17 | A19-D2-Y1 |
| 18 | A19-D2-Y2 |
| 19 | A19-D2-Y3 |
| 20 | A19-D2-Y4 |
| 21 | A19-D2-Y5 |
| 22 | A19-D2-Y6 |
| 23 | A19-D2-Y7 |
| 24 | A19-D3-Y1 |
| 25 | A19-D3-Y2 |
| 26 | A19-D3-Y3 |
| 27 | A19-D3-Y4 |
| 28 | A19-D3-Y5 |
| 29 | A19-D3-Y6 |
| 30 | A19-D3-Y7 |
| 31 | A19-D4-Y1 |
| 32 | A19-D4-Y2 |
| 33 | A19-D4-Y3 |
| 34 | A19-D4-Y4 |
| 35 | A19-D4-Y5 |
| 36 | A19-D4-Y6 |
| 37 | A19-D4-Y7 |
| 38 | A19-D5-Y1 |
| 39 | A19-D5-Y2 |
| 40 | A19-D5-Y3 |
| 41 | A19-D5-Y4 |
| 42 | A19-D5-Y5 |
| 43 | A19-D5-Y6 |
| 44 | A19-D5-Y7 |
| 45 | A19-D6-Y1 |
| 46 | A19-D6-Y2 |
| 47 | A19-D6-Y3 |
| 48 | A19-D6-Y4 |
| 49 | A19-D6-Y5 |
| 50 | A19-D6-Y6 |
| 51 | A19-D6-Y7 |
| 52 | A19-D7-Y1 |
| 53 | A19-D7-Y2 |
| 54 | A19-D7-Y3 |
| 55 | A19-D7-Y4 |
| 56 | A19-D7-Y5 |
| 57 | A19-D7-Y6 |
| 58 | A19-D7-Y7 |
| 59 | A30-D1-Y1 |
| 60 | A30-D1-Y2 |
| 61 | A30-D1-Y3 |
| 62 | A30-D1-Y4 |
| 63 | A30-D1-Y5 |
| 64 | A30-D1-Y6 |
| 65 | A30-D1-Y7 |
| 66 | A30-D2-Y1 |
| 67 | A30-D2-Y2 |
| 68 | A30-D2-Y3 |
| 69 | A30-D2-Y4 |
| 70 | A30-D2-Y5 |
| 71 | A30-D2-Y6 |
| 72 | A30-D2-Y7 |
| 73 | A30-D3-Y1 |
| 74 | A30-D3-Y2 |
| 75 | A30-D3-Y3 |
| 76 | A30-D3-Y4 |
| 77 | A30-D3-Y5 |
| 78 | A30-D3-Y6 |
| 79 | A30-D3-Y7 |
| 80 | A30-D4-Y1 |
| 81 | A30-D4-Y2 |
| 82 | A30-D4-Y3 |
| 83 | A30-D4-Y4 |
| 84 | A30-D4-Y5 |
| 85 | A30-D4-Y6 |
| 86 | A30-D4-Y7 |
| 87 | A30-D5-Y1 |
| 88 | A30-D5-Y2 |
| 89 | A30-D5-Y3 |

TABLE 4-continued

| | |
|---|---|
| 90 | A30-D5-Y4 |
| 91 | A30-D5-Y5 |
| 92 | A30-D5-Y6 |
| 93 | A30-D5-Y7 |
| 94 | A30-D6-Y1 |
| 95 | A30-D6-Y2 |
| 96 | A30-D6-Y3 |
| 97 | A30-D6-Y4 |
| 98 | A30-D6-Y5 |
| 99 | A30-D6-Y6 |
| 100 | A30-D6-Y7 |
| 101 | A30-D7-Y1 |
| 102 | A30-D7-Y2 |
| 103 | A30-D7-Y3 |
| 104 | A30-D7-Y4 |
| 105 | A30-D7-Y5 |
| 106 | A30-D7-Y6 |
| 107 | A30-D7-Y7 |

Methods of Treatment

The compounds and compositions described herein can be used in methods for treating diseases. In one embodiment, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof. In one embodiment, the patient or subject is a mammal, such as a human. In an embodiment, the patient or subject is a human. In an embodiment, the patient or subject is an animal, for example a farm animal, or a companion animal. In an embodiment, the patient or subject is a canine, feline, or equine.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein A is selected from the group consisting of $A^1$ to $A^{40}$ as defined in Table 1.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein D is selected from the group consisting of $D^1$ to $D^9$ as defined in Table 2.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein Y is selected from the group consisting of $Y^1$ to $Y^7$ as defined in Table 3.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein the compound, or a pharmaceutically acceptable salt, solvate, hydrate, cocrystal, or prodrug thereof, is included in a pharmaceutical composition further including a pharmaceutically acceptable excipient.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein the disease or disorder is an inflammation disease or disorder, a cancer, a neurodegenerative diseases or disorder, a cardiovascular disease or disorder, an ocular disease or disorder, or an angiogenic disease or disorder.

In some embodiments, the invention relates to a method of treating cancer in a patient in need thereof, including administering to the patient a therapeutically effective amount of a compound of Formula A-D-Y, or a pharmaceutically acceptable salt, solvate, hydrate, cocrystal, or prodrug thereof, wherein the cancer is ovarian cancer, colon cancer, leukemia, gastric cancer, lung cancer, pancreatic cancer, or a cancer characterized by a K-Ras mutation.

In some embodiments, the invention relates to a method of treating cancer in a patient in need thereof, including administering to the patient a therapeutically effective amount of a compound of Formula A-D-Y, or a pharmaceutically acceptable salt, solvate, hydrate, cocrystal, or prodrug thereof, wherein the cancer is chemoresistant to other therapeutic agents.

In some embodiments, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, wherein treatment includes inhibiting VEGF expression.

In some embodiments, the invention relates to a method of treating diabetic retinopathy in a patient in need thereof, including administering to the patient a therapeutically effective amount of a compound of Formula A-D-Y, or a pharmaceutically acceptable salt, solvate, hydrate, cocrystal, or prodrug thereof.

In some embodiments, the invention relates to a method of treating inflammation in the eye in a patient in need thereof, including administering to the patient a therapeutically effective amount of a compound of Formula A-D-Y, or a pharmaceutically acceptable salt, solvate, hydrate, cocrystal, or prodrug thereof.

In some embodiments, the invention relates to a method of treating dry eye in a patient in need thereof, including administering to the patient a therapeutically effective amount of a compound of Formula A-D-Y, or a pharmaceutically acceptable salt, solvate, hydrate, cocrystal, or prodrug thereof.

In some embodiments, the invention relates to a method of treating a disease or disorder of the anterior of the eye in a patient in need thereof, including administering to the patient a therapeutically effective amount of a compound of Formula A-D-Y, or a pharmaceutically acceptable salt, solvate, hydrate, cocrystal, or prodrug thereof.

In some embodiments, the invention relates to a method of treating a disease or disorder of the posterior of the eye in a patient in need thereof, including administering to the patient a therapeutically effective amount of a compound of Formula A-D-Y, or a pharmaceutically acceptable salt, solvate, hydrate, cocrystal, or prodrug thereof.

In some embodiments, the compounds and compositions described herein can be used in methods for treating diseases associated with the up- and/or downregulation of VEGF expression, and/or K-Ras expression.

In one embodiment, the invention relates to a method of treating a disease alleviated by administering a compound of Formula A-D-Y in a patient in need thereof, including administering to the patient a therapeutically effective amount of a compound of Formula A-D-Y in a dosage unit form. In one embodiment, the dosage unit comprises a physiologically compatible carrier medium.

In one embodiment, the invention relates to a method of treating a disease alleviated by administering a compound of Formula A-D-Y to a patient in need thereof, including administering to the patient a therapeutically effective amount of a compound of Formula A-D-Y, wherein the disease is cancer or an inflammatory disease. In some embodiments, the disease is rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In one embodiment, the disease is a hyperproliferative diseases. In some embodiments, the hyperproliferative disorder is cancer. In some embodiments, the cancer is pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma, and the like. In other embodiments, the cancer is acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom's macroglobulinemia.

In some embodiments, the hyperproliferative disorder (e.g., cancer) treated by the compounds and compositions described herein includes cells having VEGF and/or K-Ras related protein expression.

In one embodiment, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, and one or more additional therapeutic agents, including chemotherapeutic and/or immunotherapeutic agents.

In one embodiment, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, and one or more additional therapeutic agents, including an antibiotic. In some embodiments, the antibiotic may include one or more of tetracycline, chlortetracycline, bacitracin, neomycin, polymyxin, gramicidin, oxytetracycline, chloramphenicol, gentamycin, and erythromycin. Other antibiotics include aminoglycoside, ampicillin, carbenicillin, cefazolin, cephalosporin, chloramphenicol, clindamycin, everninomycin, gentamycin, kanamycin, lipopeptides, methicillin, nafcillin, novobiocia, oxazolidinones, penicillin, quinolones, rifampin, streptogramins, streptomycin, sulfamethoxazole, sulfonamide, trimethoprim and vancomycin. In some embodiments, the compound of Formula A-D-Y does not inhibit, impede, or otherwise delay or prevent the efficacy of the antibiotic, for example a co-administered antibiotic. In some embodiments, the antibiotic does not inhibit, impede, or otherwise delay or prevent the efficacy of the compound of Formula A-D-Y, for example a co-administered compound of Formula A-D-Y.

In one embodiment, the invention relates to a method of treating a disease or disorder in a patient in need thereof, including administering to the patient a therapeutically effective amount of a compound of Formula A-D-Y, or a pharmaceutically acceptable salt, solvate, hydrate, cocrystal, or prodrug thereof, and one or more additional therapeutic agents, including an antibiotic, including topical treatment of ocular inflammatory conditions. Inflammatory conditions of the eye are frequent. Often when the eye is inflamed, it is clinically difficult to assess whether the inflammation is due to an infectious agent, to non-infectious causes, or both. As the treatment for these two etiologies is different, in some embodiments, there is a need for timely treatment because, if untreated, these diseases or disorders can have catastrophic consequences for the eye. In some embodiments, the use of a combination drug with an anti-infective component is indicated where there is a risk of infection, and/or bacteria is potentially present in the eye. In some embodiments, an effective amount of a compound of Formula A-D-Y, or a pharmaceutically acceptable salt, solvate, hydrate, cocrystal, or prodrug thereof, is combined with one or more additional therapeutic agents in an eye drop formulation, or an ophthalmic ointment formulation. In some embodiments, the additional therapeutic agent is neomycin sulfate. In some embodiments, the additional therapeutic agent is polymyxin B sulfate. In some embodiments, the additional therapeutic agent is an anti-inflammatory agent.

In some embodiments, the additional therapeutic agent is dexamethasone. In some embodiments, the additional therapeutic agent is cortisone or other corticosteroid. In some embodiments, the additional therapeutic agent is tobramycin. In some embodiments, an effective amount of a compound of Formula A-D-Y, or a pharmaceutically acceptable salt, solvate, hydrate, cocrystal, or prodrug thereof, is combined with one or more additional therapeutic agents in an eye drop formulation, or an ophthalmic ointment formulation, excluding dexamethasone.

The term "compound with reduced risk of corneal melt" refers to compounds that are less likely to cause corneal melt in a patient being treated when compared to an NSAID known to cause corneal melt (e.g., diclofenac (see, e.g., Julianne, C. et al. "Corneal Melting Associated with Use of Topical Nonsteroidal Anti-Inflammatory Drugs after Ocular Surgery," (2000) 118:1129-1132)) at about the same dosage. In some embodiments, the compounds of Formula A-D-Y, or pharmaceutically acceptable salts, solvates, hydrates, cocrystals, or prodrugs thereof, are compounds with reduced risk of corneal melt.

The compounds and compositions described herein can be used in methods for treating diseases of the eye. One example is ovarian cancer. Ovarian cancer is the most lethal gynecologic cancer, affecting women of all ages. About 95% are epithelial ovarian cancers (referred to here as OvCa); germ cell tumors and sex cord-stromal tumors comprise the remainder. The 5-year survival is only 17%-28% for those with advanced-stage tumors.

For a minority of ovarian cancer patients, surgery is curative. All others are treated with cytoreductive surgery plus chemotherapy with a combination of cisplatin and paclitaxel, which achieves a response rate of ~80%. About 70% of patients with stage III or IV ovarian cancer recur within 5 years and drug resistance emerges. Patients with a relapse-free interval of >6 months are considered "cisplatin-sensitive" while those who progress on or relapse within 6 months of the initial therapy are considered "cisplatin-resistant." Patients with resistant disease are treated with other agents, such as liposomal doxorubicin, gemcitabine, topotecan, or etoposide. The overall response rates with these drugs are 10%-25% and the duration of response is short.

Available drugs have reached a therapeutic ceiling. During the last 20 years the extension in overall survival has been sluggish, Sadly, recent targeted therapies of ovarian cancer. e.g., PARP inhibitors, anti-TNF antibodies and folate antagonists, have extended overall survival minimally or not at all. Thus novel agents are required to improve outcomes for advanced ovarian cancer.

The compounds and compositions described herein can be used in methods for treating diseases of the eye. In some embodiments, the diseases of the eye that are treated by the compounds, compositions, methods, and kits described herein include dry eye disease and retinopathy. In some embodiments, retinopathy may include the diseases of diabetic retinopathy, retinopathy of prematurity, VEGF retinopathy, age related macular degeneration, retinal vein occlusion, and/or hypertensive retinopathy. In certain embodiments, retinopathy may be diabetic retinopathy.

Dry eye disease (DED) is a multi-factorial disease of the ocular surface characterized by loss of homeostasis of the tear film and accompanied by ocular symptoms. The tear film in DED is abnormal because of one or more of three reasons: tear production is decreased; tear evaporation is increased; or the mucus or lipids of the tear are abnormal. The clinical manifestations of DED can vary in severity from very mild to the point that they decrease the ability to perform activities requiring visual attention such as reading and driving, seriously affecting the patient's quality of life. Given its worldwide distribution and the lack of a single definitive test or consensus of criteria for its diagnosis, prevalence figures for DED vary. The best estimate of its prevalence is 15% (17.9% for women and 10.5% for men); some authors consider even 15% an underestimate.

DED is an inflammatory disease whose pathogenesis is under extensive study. For example, dysfunction of the tear glands, chronic irritative stress or systemic autoimmune diseases can lead to ocular inflammation. In turn, inflammation causes dysfunction or death of cells responsible for tear secretion establishing a vicious cycle, which, regardless of the initiating insult, leads to ocular surface disease. The important contributors to the inflammatory process in DED are: (1) activation of pro-inflammatory cytokines; tear hyperosmolarity, which stimulates inflammatory mediators through MAPKs; (2) matrix metalloproteinases (MMPs), which lyse components of the corneal epithelial basement membrane and tight junction proteins; (3) chemokines, which recruit nearby responsive cells; and (4) T cells, which can amplify the cascade by attracting inflammatory cells, e.g., in Sjögren's syndrome.

The treatment of DED depends on its clinical severity. The symptoms of very mild disease are often treated with artificial tears, which provide partial relief but do not suppress inflammation. Advanced disease is managed with the immunosuppressant cyclosporine, the recently approved integrin antagonist lifitegrast, punctal plugs, or rarely corticosteroids. Non-steroidal anti-inflammatory drugs (NSAIDs) have no role in DES.

Diabetic retinopathy refers to retinal changes that occur in patients with diabetes mellitus. These changes affect the small blood vessels of the retina and can lead to vision loss through several different pathways. Macular edema, defined as retinal thickening and edema involving the macula can occur at any stage of diabetic retinopathy. Diabetic retinopathy is one of the commonest causes of vision loss. Vascular endothelial growth factor (VEGF) is secreted by ischemic retina. VEGF leads to (a) increased vascular permeability resulting in retinal swelling/edema and (b) angiogenesis—new blood vessel formation. In some embodiments, agents that suppress VEGF can control diabetic retinopathy.

In addition to diabetic retinopathy, several other ocular diseases are characterized by abnormal vascular phenomena that are predominantly dependent on VEGF. Given the role of VEGF in these disorders, controlling VEGF is an approach to their prevention and treatment. Prominent among them is age-related macular degeneration (AMD), a degenerative disease of the central portion of the retina (the macula) that results primarily in loss of central vision. Central vision is required for activities such as driving, reading, watching television, and performing activities of daily living. AMD is classified as dry (atrophic) or wet (neovascular or exudative) for clinical purposes. Wet AMD, also referred to as choroidal neovascularization is characterized by growth of abnormal vessels into the subretinal space, usually from the choroidal circulation and less frequently from the retinal circulation. These abnormal blood vessels leak, leading to collections of subretinal fluid and/or blood beneath the retina.

Retinal vein occlusion (RVO) is an important cause of visual loss among older adults throughout the world. An important component of RVO are its secondary complications that affect vision, including macular edema, retinal neovascularization, and anterior segment neovascularization. VEGF pays a crucial role in these vision-determining complications. Patients with severe (ischemic) central retinal vein occlusion are at particularly high risk for neovascular glaucoma, often within the first few months of diagnosis, and should be observed at least monthly for development of anterior segment neovascularization during this period. Indeed, patients with severe (ischemic) central retinal vein occlusion are at particularly high risk for neovascular glaucoma, and are observed closely for development of anterior segment neovascularization. VEGF inhibitors in patients with RVO are hypothesized to limit macular edema and improve vision by decreasing vascular permeability.

Without wishing to be bound by any particular theory, the invention is based at least in part on several unexpected observations relating to the combination of compounds of Formula A-D-Y, or pharmaceutically acceptable salts, solvates, hydrates, cocrystals, or prodrugs thereof, with anti-infective agents. In some embodiments, such combinations can be used to treat ocular conditions. In some embodiments, certain chemical moieties in the compounds of Formula A-D-Y, for example "A," are residues relating to nonsteroidal anti-inflammatory active compounds (NSAIDs). However, in some embodiments, the compounds of Formula A-D-Y do not behave like NSAIDs when applied to the eye. For example, in some embodiments, compounds of Formula A-D-Y do not inhibit the synthesis of prostaglandins in the eye, as is typically the case with NSAIDs. In other embodiments, the compounds of Formula A-D-Y do not cause corneal melt, which is a complication of ocular application of NSAIDs, and which typically prohibits or restricts the use of topical ophthalmic NSAIDs. However, the compounds of Formula A-D-Y of the current invention unexpectedly possess beneficial analgesic properties similar to NSAIDs. In some embodiments, the compounds of Formula A-D-Y of the current invention provide corneal analgesia. In some embodiments, the compounds of Formula A-D-Y of the current invention provide short-term corneal analgesia. Thus, in some embodiments, the compounds of Formula A-D-Y of the current invention provide symptomatic relief from the ocular discomfort associated with various ophthalmic diseases or disorders. In some embodiments, the compounds of Formula A-D-Y of the current invention do not inhibit the antibacterial efficacy of antibiotics administered in a combination.

Efficacy of the compounds and combinations of compounds described herein in treating the indicated diseases or disorders can be tested using various models known in the art, and described herein, which provide guidance for treatment of human disease. Any and all of the described methods of treatment may include medical follow-up to determine the therapeutic or prophylactic effect brought about in the subject undergoing treatment with the compound(s) and/or composition(s) described herein.

Pharmaceutical Compositions

In an embodiment, an active pharmaceutical ingredient or combination of active pharmaceutical ingredients, such as any of the compounds of Formula A-D-Y of the invention, is provided as a pharmaceutically acceptable composition.

In one embodiment, the invention relates to a pharmaceutical composition including a therapeutically effective amount of a compound of Formula A-D-Y for the treatment of a disease alleviated by administering a compound of Formula A-D-Y in a patient in need thereof, or a pharmaceutically acceptable salt, solvate, hydrate, cocrystal, or prodrug thereof, and a physiologically compatible carrier medium.

In one embodiment, the invention relates to a pharmaceutical composition including a therapeutically effective amount of a compound of Formula A-D-Y for the treatment of a disease alleviated by administering a compound of Formula A-D-Y in a patient in need thereof, or a pharmaceutically acceptable salt, solvate, hydrate, cocrystal, or prodrug thereof, and a physiologically compatible carrier medium, wherein the disease is cancer or an inflammatory disease. In one embodiment, the disease is rheumatoid arthritis, a cardiovascular disease, multiple sclerosis, inflammatory bowel disease, chronic obstructive pulmonary disease (COPD), asthma, acute respiratory distress syndrome (ARDS), or acute lung injury (ALI). In one embodiment, the diseases is a cancer such as acoustic neuroma, adenocarcinoma, angiosarcoma, astrocytoma, basal cell carcinoma, bile duct carcinoma, bladder carcinoma, brain cancer, breast cancer, bronchogenic carcinoma, cervical cancer, chordoma, choriocarcinoma, colon cancer, colorectal cancer, craniopharyngioma, cystadenocarcinoma, embryonal carcinoma, endotheliocarcinoma, ependymoma, epithelial carcinoma, esophageal cancer, Ewing's tumor, fibrosarcoma, gastric cancer, glioblastoma multiforme, glioma, head and neck cancer, hemangioblastoma, hepatoma, kidney cancer, leiomyosarcoma, liposarcoma, lung cancer, lymphangioendotheliosarcoma, lymphangiosarcoma, medullary carcinoma, medulloblastoma, melanoma, meningioma, mesothelioma, myxosarcoma, nasal cancer, neuroblastoma, oligodendroglioma, oral cancer, osteogenic sarcoma, ovarian cancer, pancreatic cancer, papillary adenocarcinoma, papillary carcinoma, pinealoma, prostate cancer, rabdomyosarcoma, rectal cancer, renal cell carcinoma, retinoblastoma, sarcoma, sebaceous gland carcinoma, seminoma, skin cancer, squamous cell carcinoma, stomach cancer, sweat gland carcinoma, synovioma, testicular cancer, small cell lung carcinoma, throat cancer, uterine cancer, Wilm's tumor, blood cancer, acute erythroleukemic leukemia, acute lymphoblastic B-cell leukemia, acute lymphoblastic T-cell leukemia, acute lymphoblastic leukemia, acute megakaryoblastic leukemia, acute monoblastic leukemia, acute myeloblastic leukemia, acute myelomonocytic leukemia, acute nonlymphocytic leukemia, acute promyelocytic leukemia, acute undifferentiated leukemia, chronic lymphocytic leukemia, chronic myelocytic leukemia, hairy cell leukemia, multiple myeloma, heavy chain disease, Hodgkin's disease, multiple myeloma, non-Hodgkin's lymphoma, polycythemia vera, or Waldenstrom's macroglobulinemia.

In some embodiments, the compositions described herein may be formulated for administration topically to the eye and surrounding tissues, particularly to the inner surface of the eye and the inner surface of the eyelids, including e.g., cornea, conjunctiva and sclera. Such compositions, for example, may be formulated for instillation administration, administration into conjunctival sac and conjunctival administration. In particular, the compositions described herein may be formulated as eye drops. Such eye drop formulations may include a liquid or semisolid pharmaceutical composition adapted to administration to the eye. A typical example of an eye drop composition is an ophthalmic solution to be administered dropwise to the eye.

In some embodiments, the concentration of each of the active pharmaceutical ingredients provided in the pharmaceutical compositions of the invention, such as any of the compounds of Formula A-D-Y of the invention, is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the compounds of Formula A-D-Y of the invention, is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v of the pharmaceutical composition.

In some embodiments, the concentration of each of the active pharmaceutical ingredients provided in the pharmaceutical compositions of the invention, such as any of the compounds of Formula A-D-Y of the invention, is in the range from about 0.0001% to about 50%, about 0.001% to about 40%, about 0.01% to about 30%, about 0.02% to about 29%, about 0.03% to about 28%, about 0.04% to about 27%, about 0.05% to about 26%, about 0.06% to about 25%, about 0.07% to about 24%, about 0.08% to about 23%, about 0.09% to about 22%, about 0.1% to about 21%, about 0.2% to about 20%, about 0.3% to about 19%, about 0.4% to about 18%, about 0.5% to about 17%, about 0.6% to about 16%, about 0.7% to about 15%, about 0.8% to about 14%, about 0.9% to about 12% or about 1% to about 10% w/w, w/v, or v/v of the pharmaceutical composition.

In some embodiments, the concentration of each of the active pharmaceutical ingredients provided in the pharmaceutical compositions of the invention, such as any of the compounds of Formula A-D-Y of the invention, is in the range from about 0.001% to about 10%, about 0.01% to about 5%, about 0.02% to about 4.5%, about 0.03% to about 4%, about 0.04% to about 3.5%, about 0.05% to about 3%, about 0.06% to about 2.5%, about 0.07% to about 2%, about 0.08% to about 1.5%, about 0.09% to about 1%, about 0.1% to about 0.9% w/w, w/v, or v/v of the pharmaceutical composition.

In some embodiments, the concentration of each of the active pharmaceutical ingredients provided in the pharmaceutical compositions of the invention, such as any of the compounds of Formula A-D-Y of the invention, is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the amount of each of the active pharmaceutical ingredients provided in the pharmaceutical compositions of the invention, such as any of the foregoing compounds of Formula A-D-Y of the invention, is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of each of the active pharmaceutical ingredients provided in the pharmaceutical compositions of the invention, such as any of the compounds of Formula A-D-Y of the invention, is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5 g, 3 g, 3.5, 4 g, 4.5 g, 5, 5.5 g, 6 g, 6.5 g, 7 g, 7.5 g, 8 g, 8.5 g, 9 g, 9.5 g, or 10 g.

Each of the active pharmaceutical ingredients according to the invention is effective over a wide dosage range. For example, in the treatment of adult humans, dosages independently range from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician. The clinically-established dosages of the compounds of Formula A-D-Y of the invention may also be used if appropriate.

In an embodiment, the molar ratio of two active pharmaceutical ingredients in the pharmaceutical compositions is in the range from 10:1 to 1:10, preferably from 2.5:1 to 1:2.5, and more preferably about 1:1. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20. In an embodiment, the weight ratio of the molar ratio of two active pharmaceutical ingredients in the pharmaceutical compositions is selected from the group consisting of 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20.

In an embodiment, the pharmaceutical compositions described herein, such as any of the compounds of Formula A-D-Y of the invention, are for use in the treatment of an inflammation disease or disorder, a cancer, a neurodegenerative diseases or disorder, a cardiovascular disease or disorder, an ocular disease or disorder, or an angiogenic disease or disorder. In an embodiment, the pharmaceutical compositions described herein, such as any of the compounds of Formula A-D-Y of the invention, are for use in the treatment of ovarian cancer, colon cancer, leukemia, gastric cancer, lung cancer, pancreatic cancer, or a cancer characterized by a K-Ras mutation. In an embodiment, the pharmaceutical compositions described herein, such as any of the compounds of Formula A-D-Y of the invention, are for use in the treatment of a cancer chemoresistant to other therapeutic agents, for example cisplatin, or taxol. In an embodiment, the pharmaceutical compositions described herein, such as any of the compounds of Formula A-D-Y of the invention, are for use in the treatment of diabetic retinopathy.

In an embodiment, the pharmaceutical compositions described herein, such as any of the compounds of Formula A-D-Y of the invention, are for use in the treatment of hyperproliferative disorders associated with the overexpression or up- and/or downregulation of VEGF and/or K-Ras. In a some embodiments, the pharmaceutical compositions described herein are for use in the treatment of a cancer associated with overexpression or up- and/or downregulation of VEGF and/or K-Ras, such as pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, or retinoblastoma.

In an embodiment, the invention includes a composition for treating an ophthalmic condition in a patient in need thereof, wherein the ophthalmic condition is selected from the group consisting of dry eye disease and retinopathy, the composition comprising a therapeutically effective amount of a compound of Formula A-D-Y, or a pharmaceutically acceptable salt, solvate, hydrate, cocrystal, or prodrug thereof. In some embodiments, the compositions described herein include a pharmaceutically acceptable carrier. In some embodiments, the compositions described herein include one or more of a solubilizing agent, an alcohol, an acid, and a preservative.

In some embodiments, the compositions described herein include a solubilizing agent and an alcohol. In some embodiments, the compositions described herein include a solubilizing agents and an acid. In some embodiments, the compositions described herein include a solubilizing agents and a preservative. In some embodiments, the compositions described herein include a solubilizing agent, an alcohol, and an acid. In some embodiments, the compositions described herein include a solubilizing agent, an alcohol, an acid, and a preservative.

In some embodiments, the compositions of the invention may include a compound of Formula A-D-Y, or a pharmaceutically acceptable salt, solvate, hydrate, cocrystal, or prodrug thereof, in an amount, by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the solubilizing agent is vitamin E TPGS (d-α-tocopheryl polyethylene glycol 1000 succinate). In some embodiments, the compositions described herein include a solubilizing agent in an amount, by weight, of about 0.5% to about 75%, or about 1% to about 70%, or about 1% to about 65%, or about 1% to about 60%, or about 1% to about 55%, or about 1% to about 50%, or about 1% to about 45%, or about 1% to about 40%, or about 1% to about 35%, or about 1% to about 30%, or about 1% to about 25%, or about 1% to about 20%, or about 1% to about 15%, or about 1% to about 10%, or about 1% to about 5%.

In some embodiments, the alcohol is a sugar alcohol, such as mannitol. In some embodiments, the compositions described herein include an alcohol in an amount by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the acid is boric acid. In some embodiments, the compositions described herein include an acid in an amount, by weight, of about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In some embodiments, the preservative is polyquaternium-1 (polyquad). In some embodiments, the compositions described herein include a preservative in an amount, by weight, of about 0.001% to about 5%, or about 0.001% to about 4%, or about 0.001% to about 3%, or about 0.001% to about 2%, or about 0.001% to about 1%, or about 0.001% to about 0.5%, or about 0.001% to about 0.1%, or about 0.001% to about 0.009%, or about 0.001% to about 0.008%, or about 0.007%, or about 0.001% to about 0.006%, or about 0.001% to about 0.005%.

In some embodiments, the compositions described herein may include a gelling excipient, such as gellan gum or sodium alginate. In some embodiments, the compositions described herein include a gelling excipient in an amount, by weight, of about 0.5% to about 20%, or about 0.1% to about 15%, or about 0.1% to about 10%, or about 0.1% to about 9%, or about 0.1% to about 8%, or about 0.1% to about 7%, or about 0.1% to about 6%, or about 0.1% to about 5%, or about 0.1% to about 4%, or about 0.1% to about 3%, or about 0.1% to about 2%, or about 0.1% to about 1%, or about 0.1% to about 0.9%, or about 0.1% to about 0.8%, or about 0.1% to about 0.7%, or about 0.1% to about 0.6%, or about 0.1% to about 0.5%.

In some embodiments, the compositions described herein may include a poloxamer. In some embodiments, the compositions described herein include a poloxamer in an amount, by weight, of about 1% to about 75%, or about 1% to about 70%, or about 1% to about 65%, or about 1% to about 60%, or about 1% to about 55%, or about 1% to about 50%, or about 1% to about 45%, or about 1% to about 40%, or about 1% to about 35%, or about 1% to about 30%, or about 1% to about 25%, or about 1% to about 20%, or about 1% to about 15%, or about 1% to about 10%, or about 1% to about 9%, or about 1% to about 8%, or about 1% to about 7%, or about 1% to about 6%, or about 1% to about 5%, or about 1% to about 4%, or about 1% to about 3%, or about 1% to about 2%.

In some embodiments, the compositions described herein include a surfactant, such as Tween 80 or polyoxyl stearate. In some embodiments, the compositions described herein include a surfactant in an amount, by weight, of about 0.01% to about 20%, or about 0.01% to about 15%, or about 0.01% to about 10%, or about 0.01% to about 9%, or about 0.01% to about 8%, or about 0.01% to about 7%, or about 0.01% to about 6%, or about 0.01% to about 5%, or about 0.01% to about 4%, or about 0.01% to about 3%, or about 0.01% to about 2%, or about 0.01% to about 1%, or about 0.01% to about 0.5%, or about 0.01% to about 0.1%, or about 0.01% to about 0.09%, or about 0.01% to about 0.08%, or about 0.07%, or about 0.01% to about 0.06%, or about 0.01% to about 0.05%.

In some embodiments, the compositions described herein include a cyclodextrin, such as (2-hydroxypropyl)-β-cyclodextrin. In some embodiments, the compositions described herein include a cyclodextrin in amount, by weight, of about 0.5% to about 95%, or about 0.5% to about 90%, or about 0.5% to about 85%, or about 0.5% to about 80%, or about 0.5% to about 75%, or about 0.5% to about 70%, or about 0.5% to about 65%, or about 0.5% to about 60%, or about 0.5% to about 55%, or about 0.5% to about 50%, or about 0.5% to about 45%, or about 0.5% to about 40%, or about 0.5% to about 35%, or about 0.5% to about 30%, or about 0.5% to about 25%, or about 0.5% to about 20%, or about 0.5% to about 15%, or about 0.5% to about 10%, or about 0.5% to about 9%, or about 0.5% to about 8%, or about 0.5% to about 7%, or about 0.5% to about 6%, or about 0.5% to about 5%, or about 0.5% to about 4%, or about 0.5% to about 3%, or about 0.5% to about 2%, or about 0.5% to about 1%.

In an embodiment, the compositions described herein may include a therapeutically effective amount of a compound of Formula A-D-Y, or a pharmaceutically acceptable salt, solvate, hydrate, cocrystal, or prodrug thereof, and one or more of a gelling excipient, e.g., gellan gum or sodium alginate, a poloxamer, a solubilizing agent, e.g., vitamin E TPGS, a surfactant, e.g., Tween 80 or polyoxyl stearate, a polyether, e.g., a polyethylene glycol, propylene glycol, Cremophor, and a cyclodextrin, e.g., (2-hydroxypropyl)-β-cyclodextrin. In some embodiments, such formulations may allow for delivery of PS to anterior segments of the eye following topical administration. In some embodiments, such formulations may be used to deliver PS to the anterior segments of the eye in an amount sufficient to treat a disease described herein that is associated with such anterior segments of the eye, i.e., a therapeutically effective amount.

In certain embodiments, a substantial portion of the total compound of Formula A-D-Y, or a pharmaceutically acceptable salt, solvate, hydrate, cocrystal, or prodrug thereof, that is distributed to the tissues after 1 hour, as determined by HPLC, is in a particular, or targeted, tissue or area. In certain embodiments, greater than 30% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens, referred to as tissues or areas of the eye, can be found in a single tissue or area of the eye. In certain embodiments, greater than 30% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 40% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 50% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 60% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 70% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 80% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area. In certain embodiments, greater than 90% of the total compound of Formula A-D-Y, or a pharmaceutically acceptable salt, solvate, hydrate, cocrystal, or prodrug thereof, in the cornea, conjunctiva, aqueous humor, vitreous body, retina, choroid, sclera, lacrimal gland and lens can be found in a single tissue or area.

As used herein, an amount described as "about 0%," by weight, is understood to be an amount that is greater than 0%.

Described below are non-limiting pharmaceutical compositions and methods for preparing the same.

Pharmaceutical Compositions for Oral Administration

In an embodiment, the invention provides a pharmaceutical composition for oral administration containing the active pharmaceutical ingredient or combination of active pharmaceutical ingredients, such as the compounds of Formula A-D-Y described herein, and a pharmaceutical excipient suitable for oral administration.

In some embodiments, the invention provides a solid pharmaceutical composition for oral administration containing: (i) an effective amount of an active pharmaceutical ingredient or combination of active pharmaceutical ingredients, and (ii) a pharmaceutical excipient suitable for oral administration. In selected embodiments, the composition further contains (iii) an effective amount of a third active pharmaceutical ingredient, and optionally (iv) an effective amount of a fourth active pharmaceutical ingredient.

In some embodiments, the pharmaceutical composition may be a liquid pharmaceutical composition suitable for oral consumption. Pharmaceutical compositions of the invention suitable for oral administration can be presented as discrete dosage forms, such as capsules, sachets, or tablets, or liquids or aerosol sprays each containing a predetermined amount of an active ingredient as a powder or in granules, a solution, or a suspension in an aqueous or non-aqueous liquid, an oil-in-water emulsion, a water-in-oil liquid emulsion, powders for reconstitution, powders for oral consumptions, bottles (including powders or liquids in a bottle), orally dissolving films, lozenges, pastes, tubes, gums, and packs. Such dosage forms can be prepared by any of the methods of pharmacy, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

Each of the active pharmaceutical ingredients can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols, or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, sodium stearyl fumarate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, silicified microcrystalline cellulose, or mixtures thereof. A lubricant can optionally be added in an amount of less than about 0.5% or less than about 1% (by weight) of the pharmaceutical composition.

When aqueous suspensions and/or elixirs are desired for oral administration, the active pharmaceutical ingredient(s) may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts, fusidic acid salts, fatty acid derivatives of amino acids, oligopeptides, and polypeptides, glyceride derivatives of amino acids, oligopeptides, and polypeptides, lecithins and hydrogenated lecithins, lysolecithins and hydrogenated lysolecithins, phospholipids and derivatives thereof, lysophospholipids and derivatives thereof, carnitine fatty acid ester salts, salts of alkylsulfates, fatty acid salts, sodium docusate, acyl-lactylates, mono- and di-acetylated tartaric acid esters of mono- and di-glycerides, succinylated mono- and di-glycerides, citric acid esters of mono- and di-glycerides, and mixtures thereof.

Within the aforementioned group, ionic surfactants include, by way of example, lecithins, lysolecithin, phospholipids, lysophospholipids and derivatives thereof, carnitine fatty acid ester salts, salts of alkylsulfates, fatty acid salts, sodium docusate, acyllactylates, mono- and di-acetylated tartaric acid esters of mono- and di-glycerides, succinylated mono- and di-glycerides, citric acid esters of mono- and di-glycerides, and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides, alkylmaltosides, alkylthioglucosides, lauryl macrogolglycerides, polyoxyalkylene alkyl ethers such as polyethylene glycol alkyl ethers, polyoxyalkylene alkylphenols such as polyethylene glycol alkyl phenols, polyoxyalkylene alkyl phenol fatty acid esters such as polyethylene glycol fatty acids monoesters and polyethylene glycol fatty acids diesters, polyethylene glycol glycerol fatty acid esters, polyglycerol fatty acid esters, polyoxyalkylene sorbitan fatty acid esters such as polyethylene glycol sorbitan fatty acid esters, hydrophilic transesterification products of a polyol with at least one member of the group consisting of glycerides, vegetable oils, hydrogenated vegetable oils, fatty acids, and sterols, polyoxyethylene sterols, derivatives, and analogs thereof, polyoxyethylated vitamins and derivatives thereof, polyoxyethylene-polyoxypropylene block copolymers, and mixtures thereof, polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols, glycerol fatty acid esters, acetylated glycerol fatty acid esters, lower alcohol fatty acids esters, propylene glycol fatty acid esters, sorbitan fatty acid esters, polyethylene glycol sorbitan fatty acid esters, sterols and sterol derivatives, polyoxyethylated sterols and sterol derivatives, polyethylene glycol alkyl ethers, sugar esters, sugar ethers, lactic acid derivatives of mono- and di-glycerides, hydrophobic transesterification products of a polyol with at least one member of the group consisting of glycerides, vegetable oils, hydrogenated vegetable oils, fatty acids and sterols, oil-soluble vitamins/vitamin derivatives, and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use—e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives, ethers of polyethylene glycols having an average molecular weight of about 200 to about 6000, such as tetrahydrofurfuryl alcohol PEG ether (glycofurol) or methoxy PEG, amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone, esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In some embodiments, a pharmaceutical composition is provided for injection containing an active pharmaceutical ingredient or combination of active pharmaceutical ingredients, such as a compound of Formula A-D-Y, and a pharmaceutical excipient suitable for injection.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, and thimerosal.

Sterile injectable solutions are prepared by incorporating an active pharmaceutical ingredient or combination of active pharmaceutical ingredients in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical Delivery

In some embodiments, a pharmaceutical composition is provided for transdermal delivery containing an active pharmaceutical ingredient or combination of active pharmaceutical ingredients, such as compounds of Formula A-D-Y described herein, and a pharmaceutical excipient suitable for topical, for example transdermal delivery, or transcorneal delivery. Any ocular drug delivery systems known in the art can be used to deliver the compounds and compositions of the invention (Patel et al., "Ocular drug delivery systems: An overview," World J Pharmacol. 2013; 2(2): 47-64).

Compositions of the present invention can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of an active pharmaceutical ingredient or combination of active pharmaceutical ingredients in controlled amounts, either with or without another active pharmaceutical ingredient.

The construction and use of transdermal patches for the delivery of pharmaceutical agents is well known in the art. See, e.g., U.S. Pat. Nos. 5,023,252, 4,992,445, and 5,001,139, the entirety of which are incorporated herein by reference. Such patches may be constructed for continuous, pulsatile, or on demand delivery of pharmaceutical agents.

Pharmaceutical Compositions for Inhalation

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra and the compounds of Formula A-D-Y described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner. Dry powder inhalers may also be used to provide inhaled delivery of the compositions.

Other Pharmaceutical Compositions and Formulations

Pharmaceutical compositions of the compounds of Formula A-D-Y described herein may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; and Pratt and Taylor, eds., Principles of Drug Action, Third Edition, Churchill Livingston, N.Y., 1990, each of which is incorporated by reference herein in its entirety.

Administration of an active pharmaceutical ingredient or combination of active pharmaceutical ingredients or a pharmaceutical composition thereof can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. The active pharmaceutical ingredient or combination of active pharmaceutical ingredients can also be administered intraadiposally or intrathecally. In some embodiments, a compound of Formula A-D-Y, or a pharmaceutical composition thereof, can be administered intraperitoneally.

Exemplary parenteral administration forms include solutions or suspensions of active compound in sterile aqueous solutions, for example, aqueous propylene glycol or dextrose solutions. Such dosage forms can be suitably buffered, if desired.

Exemplary liquid formulations include ophthalmic solutions, microemulsions, and in-situ gel formulations. Various excipients can be used in these formulations, for example excipients for regulating osmotic pressure, pH, and/or viscosity of the formulation. In some embodiments, formulations are designed to extend the contact time of liquid dosage forms with ocular tissues and to increase the tissue uptake of an active pharmaceutical ingredient. In some embodiments, such excipients are included in order to increase viscosity, and/or enhance penetration. In some embodiments, cyclodextrins are added. Cyclodextrins are cyclic oligosaccharides that form inclusion complexes with active pharmaceutical ingredients, thus increasing their aqueous solubility and bioavailability. In some embodiments, such approaches are useful for formulating hydrophobic active pharmaceutical ingredients.

In some embodiments, the invention relates to a liquid formulation including from about 0.05% to about 25%, for example about 3.5%, of a compound of Formula A-D-Y, or a pharmaceutically acceptable salt, solvate, hydrate, cocrystal, or prodrug thereof. In some embodiments, the liquid formulation includes from about 0.05% to about 25%, for example about 16%, vitamin E TPGS. In some embodiments, the liquid formulation includes from about 0.05% to about 25%, for example about 3.18%, mannitol. In some embodiments, the liquid formulation includes from about 0.05% to about 25%, for example about 1.2%, boric acid. In some embodiments, the liquid formulation includes from about 0.001% to about 2.5%, for example about 0.005% polyquaternium-1. In some embodiments, the liquid formulation includes from about 0.001% to about 2.5%, for example 0.005% of a preservative. In some embodiments, the formulation can be made by dissolving polyquaternium-1 and vitamin E TPGS (D-α-tocopheryl polyethylene glycol 1000 succinate) in purified water, adding a compound of Formula A-D-Y to the solution, and stirring at 70° C. for a period of time, for example 30 min. The solution is then centrifuged, for example at 13,200 rpm for a period of time, for example 10 min, and the supernatant is collected. Mannitol and boric acid are added to the harvested supernatant. Purified water is added to the final solution after pH adjustment to 6.7±0.2 using an alkali, for example NaOH.

In some embodiments, the invention relates to a liquid formulation including from about 0.05% to about 25%, for example from about 3% to about 4% of a compound of Formula A-D-Y, or a pharmaceutically acceptable salt, solvate, hydrate, cocrystal, or prodrug thereof. In some embodiments, the invention relates to a liquid formulation including from about 5% to about 95%, for example about 80%, 2-hydroxypropyl)-β-cyclodextrin (HP-β-CD). In some embodiments, the invention relates to a liquid formulation including from about 0.05% to about 5%, for example about 0.1% Cremophor EL (F1). In some embodiments, the invention relates to a liquid formulation including from about 0.05% to about 5%, for example about 1% Tween 80 (F2). In some embodiments, the formulation can be made by dissolving HP-β-CD (CAS No 128446-35-5), about 6 g, in 5 mL of purified water at 55° C. (on water bath). An amount of a compound of Formula A-D-Y, or a pharmaceutically acceptable salt, solvate, hydrate, cocrystal, or prodrug thereof is added to the solution, and the mixture is kept at 55° C. on a water bath overnight, or until the compound of Formula A-D-Y is fully dissolved. Kolliphor EL or Tween 80 is respectively added into the. The solution is then centrifuged at 3000 rpm for about 10 min to remove undissolved particles. The supernatant is collected.

In some embodiments, the invention relates to a liquid formulation including from about 0.05% to about 25%, for example from about 3% to about 4%, or about 3.5%, of a compound of Formula A-D-Y, or a pharmaceutically acceptable salt, solvate, hydrate, cocrystal, or prodrug thereof. In some embodiments, the invention relates to a liquid formulation including from about 90% to about 99%, for example about 96.5% propylene glycol (PG). In some embodiments, propylene glycol is well tolerated by the eye. The formulation can be administered topically to the eyes of New Zealand white rabbits as a 3.5% compound of Formula A-D-Y concentration in propylene glycol, as eye drops, and its 1-hour biodistribution determined by HPLC thereafter.

In some embodiments, each of the various exemplary formulations exemplified herein targets a compound described herein, for example a compound of Formula A-D-Y, or a pharmaceutically acceptable salt, solvate, hydrate, cocrystal, or prodrug thereof, to specific ocular tissues in a specific manner. In some embodiments, the biodistribution profiles of a compound of Formula A-D-Y, or a pharmaceutically acceptable salt, solvate, hydrate, cocrystal, or prodrug thereof, formulated as described herein are the result of an inherent physicochemical property of the compound, or a pharmaceutically acceptable salt, solvate, hydrate, cocrystal, or prodrug thereof. In some embodiments, the biodistribution profiles of a compound of Formula A-D-Y, or a pharmaceutically acceptable salt, solvate, hydrate, cocrystal, or prodrug thereof, formulated as described herein are not the result of an inherent physicochemical property of the compound, or a pharmaceutically acceptable salt, solvate, hydrate, cocrystal, or prodrug thereof. In some embodiments, the biodistribution profiles of a compound of Formula A-D-Y, or a pharmaceutically acceptable salt, solvate, hydrate, cocrystal, or prodrug thereof, formulated as described herein, result from the specific formulations described herein. In some embodiments, the formulations described herein can direct a compound of Formula A-D-Y, or a pharmaceutically acceptable salt, solvate, hydrate, cocrystal, or prodrug thereof, to tissues of therapeutic interest, e.g., cornea and conjunctiva for treatment of dry eye disease, or retina for treatment of various retinopathies.

Exemplary semi-solid formulations include high viscosity formulations that increase bioavailability by increasing the residence time of the active pharmaceutical ingredients in the precorneal area. In situ gels are viscous liquids that undergo sol-to-gel transitions upon ocular application because of changes in pH, temperature or electrolyte concentration. Gelling excipients with favorable mucoadhesive properties further increase the residence time. Polymers employed in developing these drug formulations include gellan gum, poloxamer, and cellulose acetate phthalate. Thermogels can for example be generated using poloxamer 407 or gellan gum.

In some embodiments, the invention relates to a gel formulation including from about 0.05% to about 25%, for example from about 2.4% to about 3% of a compound of Formula A-D-Y, or a pharmaceutically acceptable salt, solvate, hydrate, cocrystal, or prodrug thereof. In some embodiments, the invention relates to a gel formulation including from about 0.05% to about 5%, for example about 0.4% or about 0.5% gellan gum. In some embodiments, the invention relates to a gel formulation including from about 0.05% to about 25%, for example about 5% or about 10% vitamin E TPGS. In some embodiments, the invention relates to a gel formulation including from about 0.05% to about 25%, for example about 5% or about 10% (2-hydroxypropyl)-β-cyclodextrin. In some embodiments, a gellan gum solution is prepared by adding an appropriate amount of gellan gum to deionized water and heating the mixture to 90° C. with fast stirring (500 rpm). Once the gum is completely dissolved, the solution is filtered through a 0.22 μm filter. Then, the compound of Formula A-D-Y, or a pharmaceutically acceptable salt, solvate, hydrate, cocrystal, or prodrug thereof, and additional excipients are added to the system to achieve the desired concentration, followed by stirring at 50° C. at 500 rpm until complete dissolution.

In some embodiments, the invention relates to a gel formulation including from about 0.05% to about 25%, for example about 3% of a compound of Formula A-D-Y, or a pharmaceutically acceptable salt, solvate, hydrate, cocrystal, or prodrug thereof, and an alginate. In some embodiments, the invention relates to a gel formulation including from about 0.05% to about 5%, for example about 1.5% sodium alginate. In some embodiments, the invention relates to a gel formulation including from about 0.05% to about 25%, for example about 15% Tween 80. In some embodiments, the invention relates to a gel formulation including from about 0.05% to about 25%, for example about 10% (2-hydroxypropyl)-β-cyclodextrin. In some embodiments, the invention relates to a gel formulation including from about 0.05% to about 25%, for example about 10% polyethylene glycol 400 (PEG400). In some embodiments, the invention relates to a gel formulation including from about 0.05% to about 25%, for example about 5% polyoxyl stearate. In some embodiments, a sodium alginate solution is prepared by adding an appropriate amount of sodium alginate to deionized water and heating the mixture to 90° C. with fast stirring (500 rpm). Once sodium alginate is completely dissolved, the solution is filtered through a 0.22 μm filter. Then, a compound of Formula A-D-Y, or a pharmaceutically acceptable salt, solvate, hydrate, cocrystal, or prodrug thereof and any additional excipients are added to achieve any desired concentration and stirred at 50° C. at 500 rpm until complete dissolution.

In some embodiments, the invention relates to a nanoparticle formulation including from about 0.05% to about 25%, for example from about 3% to about 3.5% of a compound of Formula A-D-Y, or a pharmaceutically acceptable salt, solvate, hydrate, cocrystal, or prodrug thereof. In some embodiments, the invention relates to a nanoparticle formulation including from about 75% to about 99%, for example from about 96.5% to about 97% methoxy poly(ethylene glycol)-poly(lactide) (mPEG-PLA). In some embodiments, an oil phase is prepared by dissolving an amount of a compound of Formula A-D-Y, or a pharmaceutically acceptable salt, solvate, hydrate, cocrystal, or prodrug thereof, and an amount of PEG-PLA in 20 mL dichloromethane (DCM). In some embodiments, a water phase is prepared by dissolving an amount of sodium cholate in an amount of purified water. Then an amount of oil phase is gently added into an amount of water phase in an Eppendorf conical tube. To create an emulsion, probe sonication can be used for an amount of time, for example about for 2 min at 75% output (Branson 150, Fisher Scientific™, USA; watt output at about 12-13). The emulsion is then transferred into a beaker and stirred overnight at about 600 rpm in a chemical hood until the DCM is fully evaporated. The mixture is then transferred into ultrafilter tubes (Amicon Ultra-15), centrifuged at 5000 rpm for about 1 h. PBS is added into the resulting concentrated nanoparticle formulation in the ultrafilter tubes to a specific volume, and the centrifugation step is repeated once. The concentrated nanoparticles are resuspended into PBS to a desired final volume, transferred to an Eppendorf tube and spun for a short period of time, for example a few seconds, to remove aggregates. The supernatant is harvested as the final product. Nanoparticles are characterized in terms of effective diameter (nm), particle size distribution (polydispersity index), drug encapsulation efficiency (EE; calculated as EE %=drug encapsulated/drug added×100). The compound of Formula A-D-Y formulated in nanoparticles is administered topically as eye drops to New Zealand white rabbits, and the biodistribution of the compound of Formula A-D-Y in ocular tissues at various time points post administration is determined by HPLC. Biodistribution of a compound of Formula A-D-Y can also be determined after intravitreal injection. An amount of compound of Formula A-D-Y formulated in nanoparticles and diluted with PBS to about 0.2% to about 2% concentration is injected directly into the vitreous of New Zealand white rabbits, and the biodistribution is determined by HPLC. Biodistribution of a compound of Formula A-D-Y in human eyes ex vivo can be determined as described elsewhere herein. The anterior surface of the human eye (corresponding to an area slightly larger than the palpebral fissure) is brought into direct contact with a compound of Formula A-D-Y nanoparticle solution of a concentration of about 0.2%, about 1%, or about 2%, then the tissue is processed as described herein. Biodistribution of a compound of Formula A-D-Y can also be determined in porcine eyes ex vivo. Explanted pig eyes are exposed to a compound of Formula A-D-Y nanoparticle solution (concentration of about 2%) and treated similar to the human eyes.

In some embodiments, the compounds of Formula A-D-Y of the invention are capable of reaching the retina when applied topically to the anterior surface of the eye. In some embodiments, this unexpected property is realized when the compound of Formula A-D-Y of the invention is formulated in as described herein. In some embodiments, the property of a compound of Formula A-D-Y to be rapidly transported to the posterior segment of the eye can be changed, inhibited, or otherwise modulated by changing its corresponding formulation. In some embodiments, the unexpected feature of restricting the distribution of a compound of Formula A-D-Y can be used to direct the compound to a specific part of the entire eye. In some embodiments, a compound of Formula A-D-Y is directed to the anterior segment of the eye. In some embodiments, a compound of Formula A-D-Y is directed to the posterior segment of the eye.

Exemplary multicompartment formulations include nanoparticles, liposomes, dendrimers, and niosomes. Nanoparticles are polymeric carriers, which improve bioavailability thanks to increased corneal penetration and a larger surface area for dissolution. Niosomes and discosomes are twolayered carriers which increase active pharmaceutical ingredients bioavailability by extending precorneal residence time.

Kits

The invention also provides kits. The kits include an active pharmaceutical ingredient or combination of active pharmaceutical ingredients, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. In selected embodiments, an active pharmaceutical ingredient or combination of active pharmaceutical ingredients are provided as separate compositions in separate containers within the kit. In selected embodiments, an active pharmaceutical ingredient or combination of active pharmaceutical ingredients are provided as a single composition within a container in the kit. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer.

In some embodiments, the invention provides a kit including a composition including a therapeutically effective amount of an active pharmaceutical ingredient (e.g., a compound of Formula A-D-Y) or combination of active pharmaceutical ingredients or a pharmaceutically acceptable salt, solvate, hydrate, cocrystal, or prodrug thereof. These compositions are typically pharmaceutical compositions. The kit is for co-administration of the active pharmaceutical ingredient or combination of active pharmaceutical ingredients, either simultaneously or separately.

In some embodiments, the invention provides a kit including (1) a composition including a therapeutically effective amount of an active pharmaceutical ingredient (e.g., a compound of Formula A-D-Y) or combination of active pharmaceutical ingredients or a pharmaceutically acceptable salt, solvate, hydrate, cocrystal, or prodrug thereof, and (2) a diagnostic test for determining whether a patient's cancer is a particular subtype of a cancer. Any of the foregoing diagnostic methods may be utilized in the kit.

The kits described above are preferably for use in the treatment of the diseases and conditions described herein. In some embodiments, the kits are for use in the treatment of an inflammatory disease. In some embodiments, the kits are for use in the treatment of a cancer, a neurodegenerative diseases or disorder, a cardiovascular disease or disorder, an ocular disease or disorder, an angiogenic disease or disorder, ovarian cancer, colon cancer, leukemia, gastric cancer, lung cancer, pancreatic cancer, a cancer characterized by a K-Ras mutation, a cancer chemoresistant to other therapeutic agents (e.g., cisplatin or taxol), or diabetic retinopathy.

In a particular embodiment, the kits are for use in the treatment of hyperproliferative disorders, such as cancer. In some embodiments, the kits described herein are for use in the treatment of a cancer selected from the group consisting of pancreatic cancer, breast cancer, prostate cancer, lymphoma, skin cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In particular embodiments, the kits described herein are for use in the treatment of malignant melanoma.

Dosages and Dosing Regimens

The amounts of the pharmaceutical compositions administered using the methods herein, such as the dosages of compounds of Formula A-D-Y, will be dependent on the subject, e.g., human or mammal being treated, the severity of the disorder or condition, the rate of administration, the disposition of the active pharmaceutical ingredients and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day. The dosage of the pharmaceutical compositions and active pharmaceutical ingredients may be provided in units of mg/kg of body mass or in $mg/m^2$ of body surface area.

In some embodiments, the compounds described herein are delivered to mammals for the treatment of disease. A person having ordinary skill in the art would understand that, in certain embodiments, dosages of such compounds may be adjusted depending upon the mammal to be treated. For example, in certain embodiments, the treatment of rabbits is described herein and such dosages may or may not be revised upon the administration of the compounds of the invention to a human. However, a person having ordinary skill in the art may, if necessary, convert the dosages provided herein as set forth in Guidance for Industry: Estimating the Maximum Safe Starting Dose in Initial Clinical Trials for Therapeutics in Adult Healthy Volunteers, U.S. Department of Health and Human Services, Food and Drug Administration, Center for Drug Evaluation and Research (CDER), July 2005, the entirety of which is incorporated herein by reference. In some embodiments, a human equivalent dose (HED) may be determined from an animal dose, the animal dose may be multiplied by the following conversion factors, to provide units in mg/kg:

mouse=0.08, hamster=0.13, rat=0.16, ferret=0.19, guinea pig=0.22, rabbit=0.32, dog=0.54, monkey=0.32, marmoset=0.16, squirrel monkey=0.19, baboon=0.54, micropig=0.73, and mini-pig=0.95. The foregoing conversion factors are exemplary and in no way limit the dosages provided herein as would be understood by a person having ordinary skill in the art.

In some embodiments, the invention includes methods of treating a cancer in a human subject, the method comprising the steps of administering a therapeutically effective dose of an active pharmaceutical ingredient that is a compound of Formula A-D-Y to the human subject.

In some embodiments, the invention includes methods of treating a cancer in a human subject suffering from the cancer in which cancer cells overexpress K-Ras, the method comprising the steps of administering a therapeutically effective dose of an active pharmaceutical ingredient that is a compound of Formula A-D-Y to the human subject to inhibit or decrease the activity of K-Ras protein.

In some embodiments, a pharmaceutical composition or active pharmaceutical ingredient is administered in a single dose. Such administration may be by injection, e.g., intravenous injection, in order to introduce the active pharmaceutical ingredient quickly. However, other routes, including the preferred oral route, may be used as appropriate. A single dose of a pharmaceutical composition may also be used for treatment of an acute condition.

In some embodiments, a pharmaceutical composition or active pharmaceutical ingredient is administered in multiple doses. In an embodiment, a pharmaceutical composition is administered in multiple doses. Dosing may be once, twice, three times, four times, five times, six times, or more than six times per day. Dosing may be once a month, once every two weeks, once a week, or once every other day. In other embodiments, a pharmaceutical composition is administered about once per day to about 6 times per day. In some embodiments, a pharmaceutical composition is administered once daily, while in other embodiments, a pharmaceutical composition is administered twice daily, and in other embodiments a pharmaceutical composition is administered three times daily.

Administration of the active pharmaceutical ingredients may continue as long as necessary. In selected embodiments, a pharmaceutical composition is administered for more than 1, 2, 3, 4, 5, 6, 7, 14, or 28 day(s). In some embodiments, a pharmaceutical composition is administered for less than 28, 14, 7, 6, 5, 4, 3, 2, or 1 day(s). In some embodiments, a pharmaceutical composition is administered chronically on an ongoing basis—e.g., for the treatment of chronic effects. In some embodiments, the administration of a pharmaceutical composition continues for less than about 7 days. In yet another embodiment the administration continues for more than about 6, 10, 14, 28 days, two months, six months, or one year. In some cases, continuous dosing is achieved and maintained as long as necessary.

In some embodiments, an effective dosage of an active pharmaceutical ingredient disclosed herein is in the range of about 1 mg to about 500 mg, about 10 mg to about 300 mg, about 20 mg to about 250 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of an active pharmaceutical ingredient disclosed herein is less than about 25 mg, less than about 50 mg, less than about 75 mg, less than about 100 mg, less than about 125 mg, less than about 150 mg, less than about 175 mg, less than about 200 mg, less than about 225 mg, or less than about 250 mg. In some embodiments, an effective dosage of an active pharmaceutical ingredient disclosed herein is greater than about 25 mg, greater than about 50 mg, greater than about 75 mg, greater than about 100 mg, greater than about 125 mg, greater than about 150 mg, greater than about 175 mg, greater than about 200 mg, greater than about 225 mg, or greater than about 250 mg.

In some embodiments, an effective dosage of an active pharmaceutical ingredient disclosed herein is in the range of about 0.01 mg/kg to about 200 mg/kg, or about 0.1 to 100 mg/kg, or about 1 to 50 mg/kg.

In some embodiments, an active pharmaceutical ingredient is administered at a dosage of 10 to 200 mg BID, including 50, 60, 70, 80, 90, 100, 150, or 200 mg BID. In some embodiments, an active pharmaceutical ingredient is administered at a dosage of 10 to 500 mg BID, including 1, 5, 10, 15, 25, 50, 75, 100, 150, 200, 300, 400, or 500 mg BID.

In some instances, dosage levels below the lower limit of the aforesaid ranges may be more than adequate, while in other cases still larger doses may be employed without causing any harmful side effect, e.g., by dividing such larger doses into several small doses for administration throughout the day. As those skilled in the art will appreciate, the dosage actually administered will depend upon the condition being treated, the age, health and weight of the recipient, the type of concurrent treatment, if any, and the frequency of treatment. Moreover, the effective dosage amount may be determined by one skilled in the art on the basis of routine empirical activity testing to measure the bioactivity of the compound(s) in a bioassay, and thus establish the appropriate dosage to be administered.

An effective amount of the combination of the active pharmaceutical ingredient may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

In some embodiments, the compositions described herein further include controlled-release, sustained release, or extended-release therapeutic dosage forms for administration of the compounds described herein, which involves incorporation of the compounds into a suitable delivery system in the formation of certain compositions. This dosage form controls release of the compound(s) in such a manner that an effective concentration of the compound(s) in the bloodstream may be maintained over an extended period of time, with the concentration in the blood remaining relatively constant, to improve therapeutic results and/or minimize side effects. Additionally, a controlled-release system would provide minimum peak to trough fluctuations in blood plasma levels of the compound.

The following examples describe the invention in further detail. These examples are provided for illustrative purposes only, and should in no way be considered as limiting the invention.

EXAMPLES

Materials and Methods

General Methods for Chemistry: All air or moisture sensitive reactions were performed under positive pressure of nitrogen with oven-dried glassware. Chemical reagents and anhydrous solvents are obtained from commercial sources and used as-is. HPLC conditions: Column: Halo C18 4.6×150 mm, 2.7 μm, Part #: 92814-702; flow rate: 0.8 mL/min; mobile phase A: 0.05% TFA/water; B: 0.05% trifluoroacetic acid/acetonitrile; gradient: time (min)–% A/% B: 0 min=90%/10%; 8 min=20%/80%; 10 min 0%/100%; 10.1 min=90%/10%; 15 min=90%/10%.

Example 1: Synthesis of Compound 1

Scheme 1

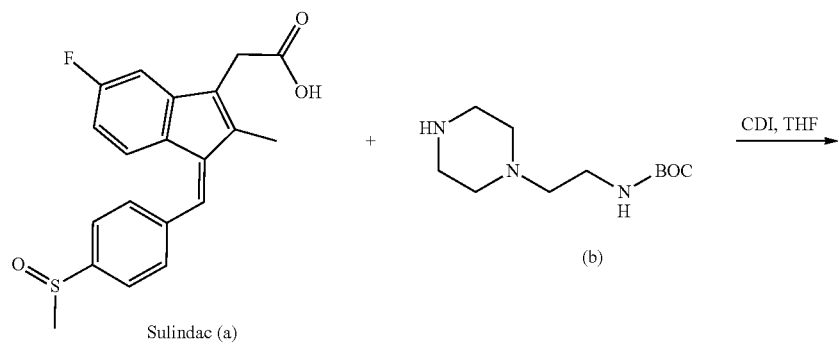

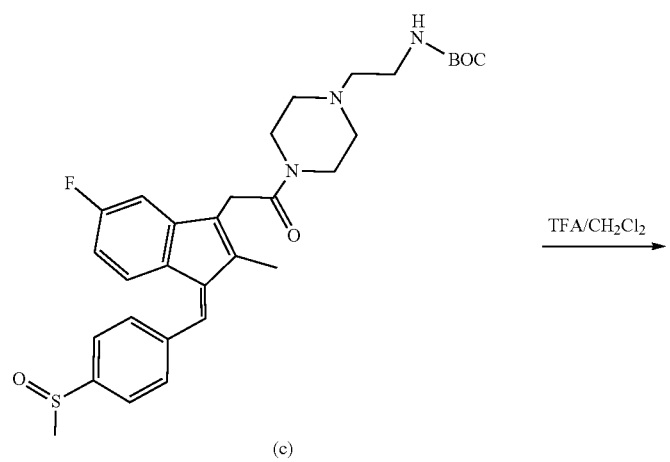

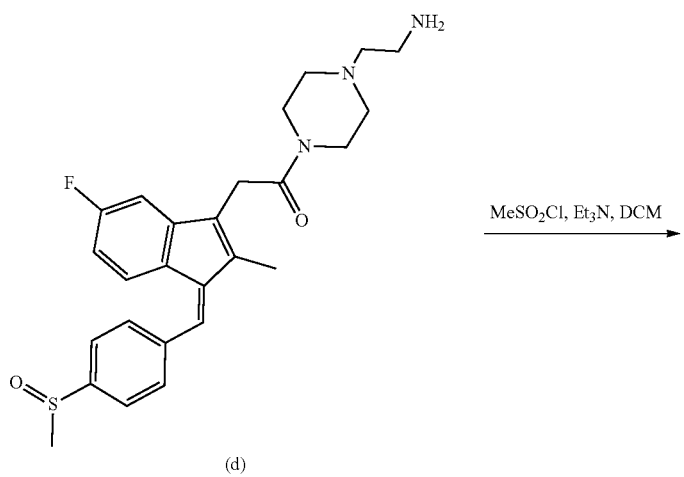

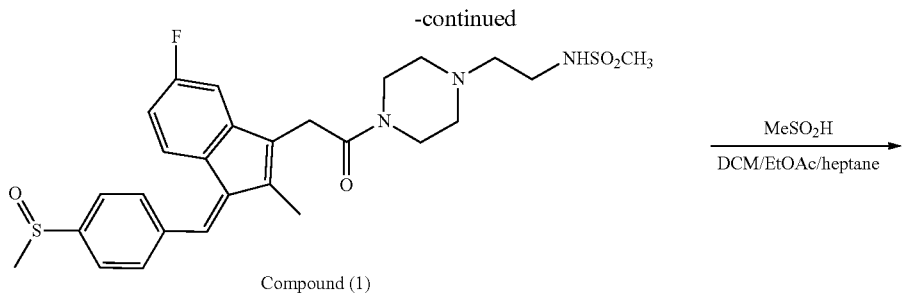

Compound (1)

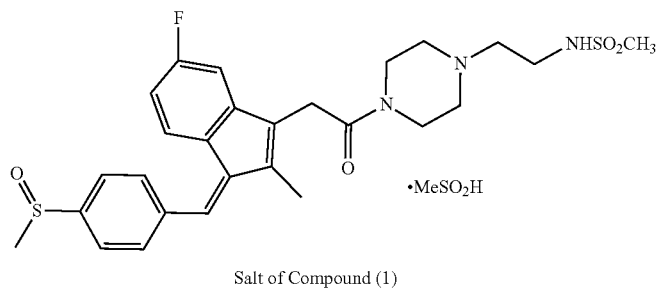

Salt of Compound (1)

Synthesis of intermediate (c): a mixture of sulindac (9.36 g, 26.2 mmol) and CDI (4.92 g, 30.1 mmol, 1.15 eq.) in THF (150 mL), was stirred at room temperature for 1-2 h to generate a thick slurry. After the complete consumption of sulindac, compound (b) (7.83 g, 34.1 mmol, 1.30 eq.) was added to the slurry. The resulting mixture was stirred at room temperature overnight to give a clear yellowish solution. After the reaction was complete as monitored by HPLC, the solvent was evaporated under reduced pressure at room temperature. EtOAc (200 mL) and $H_2O$ (60.0 mL) were then added to the reaction mixture. The organic layer was washed with $H_2O$ (40.0 mL×3), brine (30.0 mL), dried over $MgSO_4$, and evaporated to give intermediate (c) (17.2 g). The material was used in the next step without further purification.

Synthesis of intermediate (d): to a solution of intermediate (c) (17.2 g) in DCM (90.0 mL) was added TFA (35.0 mL) in ice bath. The resulting solution was stirred overnight. After the reaction was complete as monitored by HPLC, the reaction mixture was evaporated under reduced pressure at room temperature to give intermediate (d) (40.6 g with excess TFA residue). The material was used in the next step without further purification.

Synthesis of compound 1: to a solution of intermediate (d) (36.8 g with excess TFA, 23.7 mmol) in DCM (120 mL) in the presence of $Et_3N$ (100 mL) in ice bath was added methanesulfonyl chloride (4.5 g, 1.5 eq.) in DCM (20 mL) over 4 h via a syringe pump. After the reaction was complete as monitored by HPLC, the reaction mixture was diluted with DCM (150 mL), washed with $NaHCO_3$ (50 mL×2), $H_2O$ (40 mL×3), brine (50 mL), and evaporated to give a reaction mixture with excess $Et_3N$ residue. The reaction mixture was dissolved in EtOAc (200 mL) and $H_2O$ (100 mL) were added to the reaction mixture. The organic layer was washed with $H_2O$ (40.0 mL×4), brine (40.0 mL×2), dried over $MgSO_4$, evaporated, and purified by flash chromatography (0%-5% MeOH/DCM) to afford compound 1 (4.86 g) (yield: 34.0% overall 3 steps).

Figure 2:
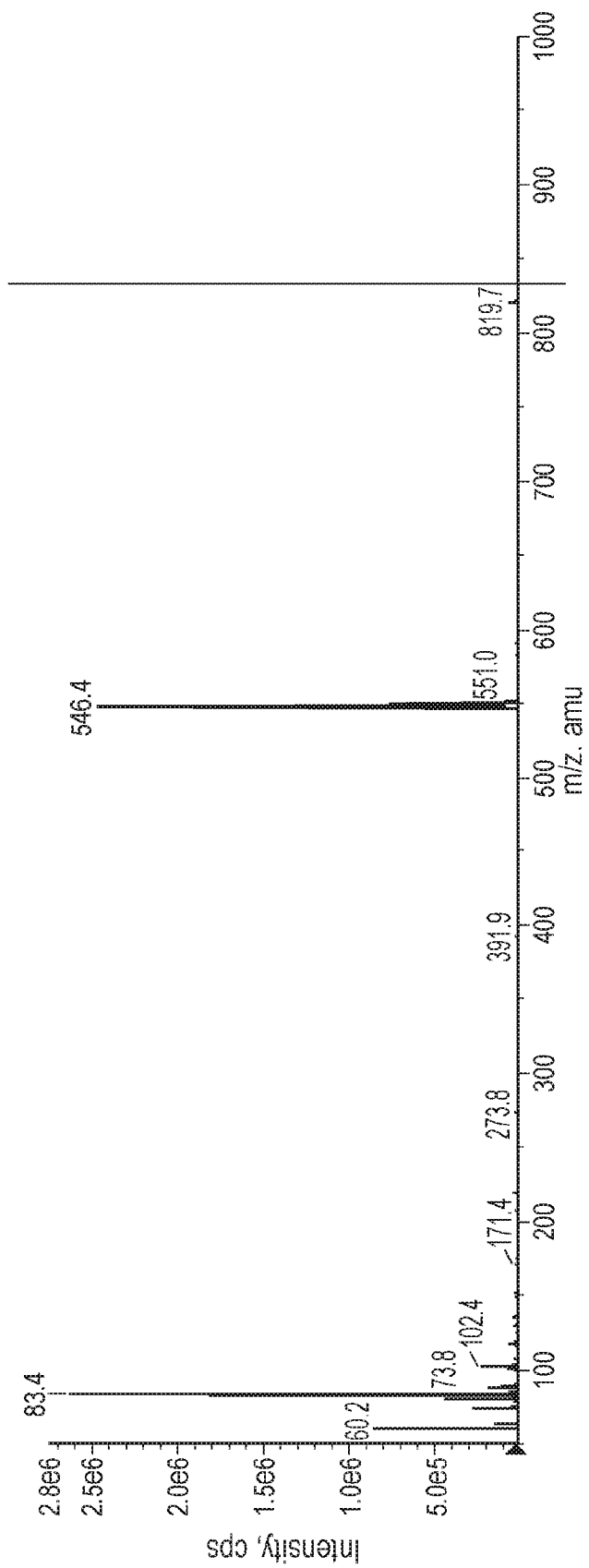
FIG. 2 illustrates the MS of compound 1 salt.

Synthesis of compound 1 salt: a solution of compound 1 (7.86 g) in DCM (100 mL) was stirred at 0° C., then methanesulfonic acid (1.38 g, 1.0 eq.) in DCM (10.0 mL) was added slowly. EtOAc (100 mL) was added to the above mixture very slowly followed by heptane (200 mL). The resulting suspension was stirred for 2 h, filtered, washed with heptane (30.0 mL×3) to give yellow solid. This yellow solid was dried under high vacuum, then dissolved in $H_2O$ (40 mL), freeze drying to furnish compound 1 salt (8.4 g). FIG. 1 illustrates the $^1$HNMR spectra of compound 1 salt, and FIG. 2 illustrates the MS of compound 1 salt.

Example 2: Synthesis of Compound 2

Scheme 2

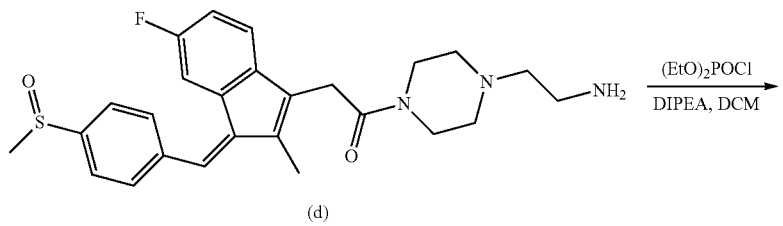

(d)

-continued

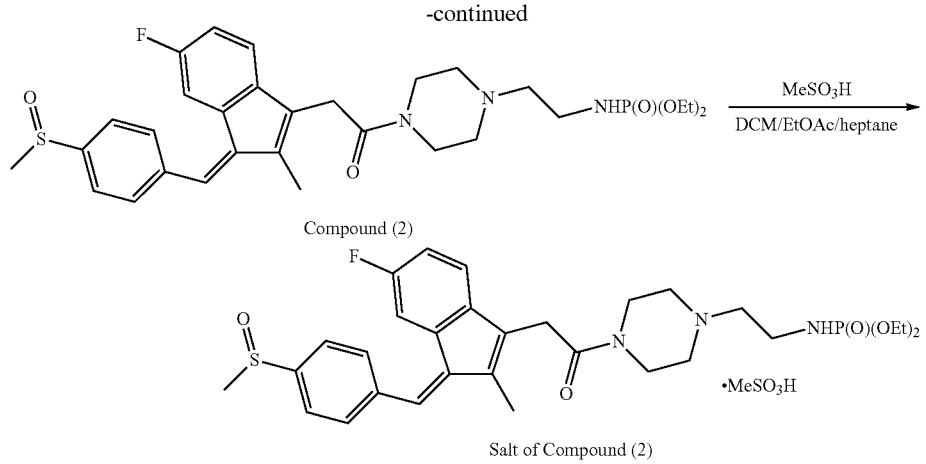

Compound (2)

Salt of Compound (2)

Synthesis of compound 2: To a solution of intermediate (d) (40.7 g with excess TFA, about 26 mmol) in DCM (200 mL) in the presence of DIPEA (150 mL) in ice bath was added diethyl chlorophosphate (6.7 g, 1.5 eq.) in DCM (20 mL) over 4 h via a syringe pump. After the reaction was complete as monitored by HPLC, the reaction mixture was concentrated, then diluted with EtOAc (200 mL), washed with NaHCO$_3$ (50 mL×2), H$_2$O (40 mL×4), brine (50 mL×2), and evaporated and purified by flash chromatography (0%-5% MeOH/DCM) to afford compound 2 (6.56 g) (yield: 41.8% over 3 steps).

Figure 3:
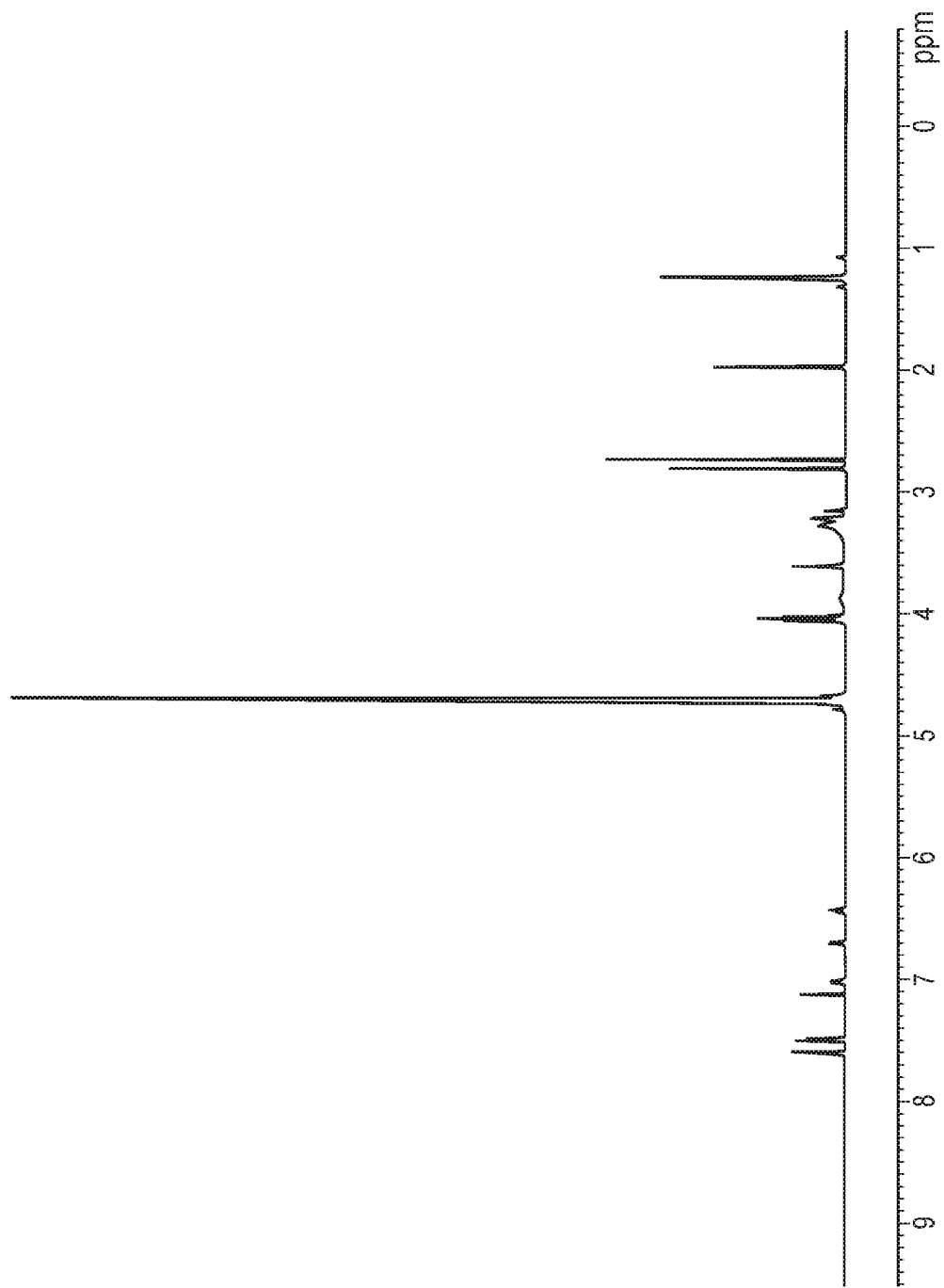
FIG. 3 illustrates the $^1$HNMR spectra of compound 2 salt.
Figure 4:
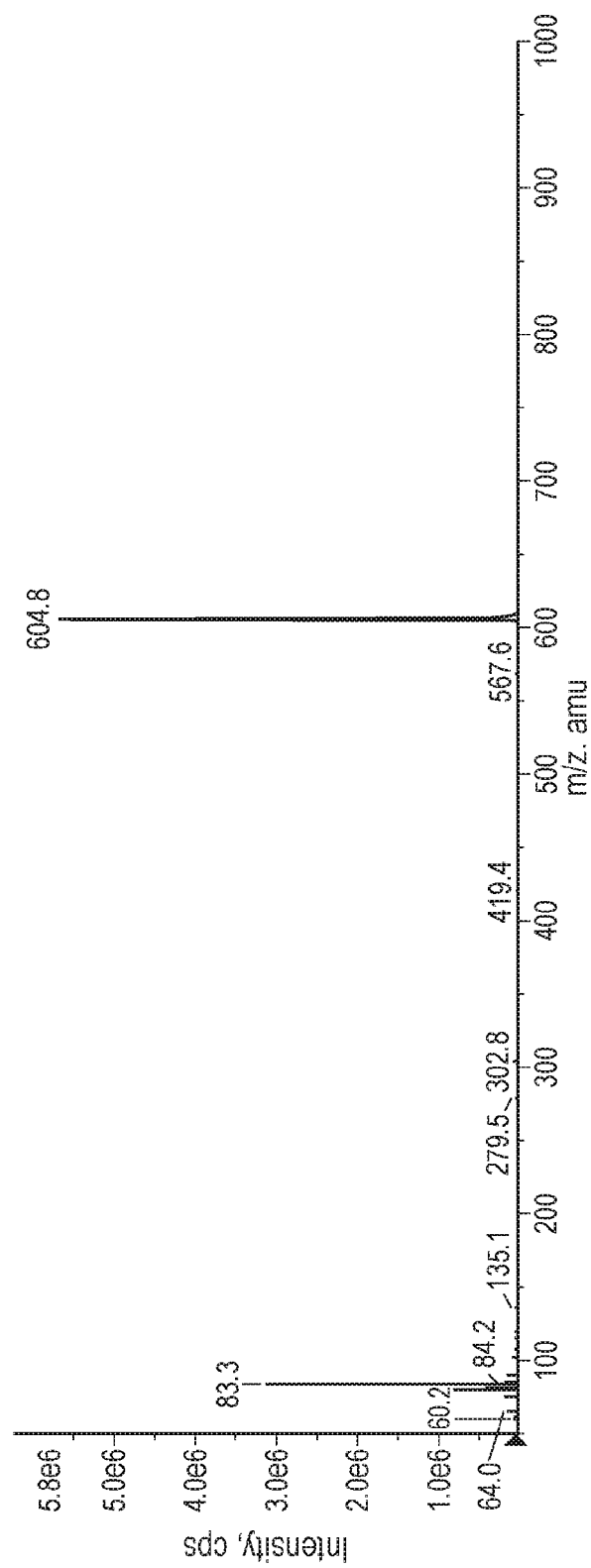
FIG. 4 illustrates the MS of compound 2 salt.

Synthesis of compound 2 salt: a solution of compound 2 (8.41 g) in DCM (100 mL) was stirred at 0° C., then methanesulfonic acid (1.32 g, 1.0 eq.) in DCM (10.0 mL) was added slowly. EtOAc (100 mL) was added to the above mixture very slowly followed by heptane (400 mL). The resulting suspension was stirred for 2 h, filtered, washed with heptane (30.0 mL×3) to give yellow solid. This yellow solid was dried under high vacuum, then dissolved in H$_2$O (50 mL), freeze drying to furnish compound 2 salt (9.40 g). FIG. 3 illustrates the $^1$HNMR spectra of compound 2 salt, and FIG. 4 illustrates the MS of compound 2 salt.

Example 3: Synthesis of Compound 5

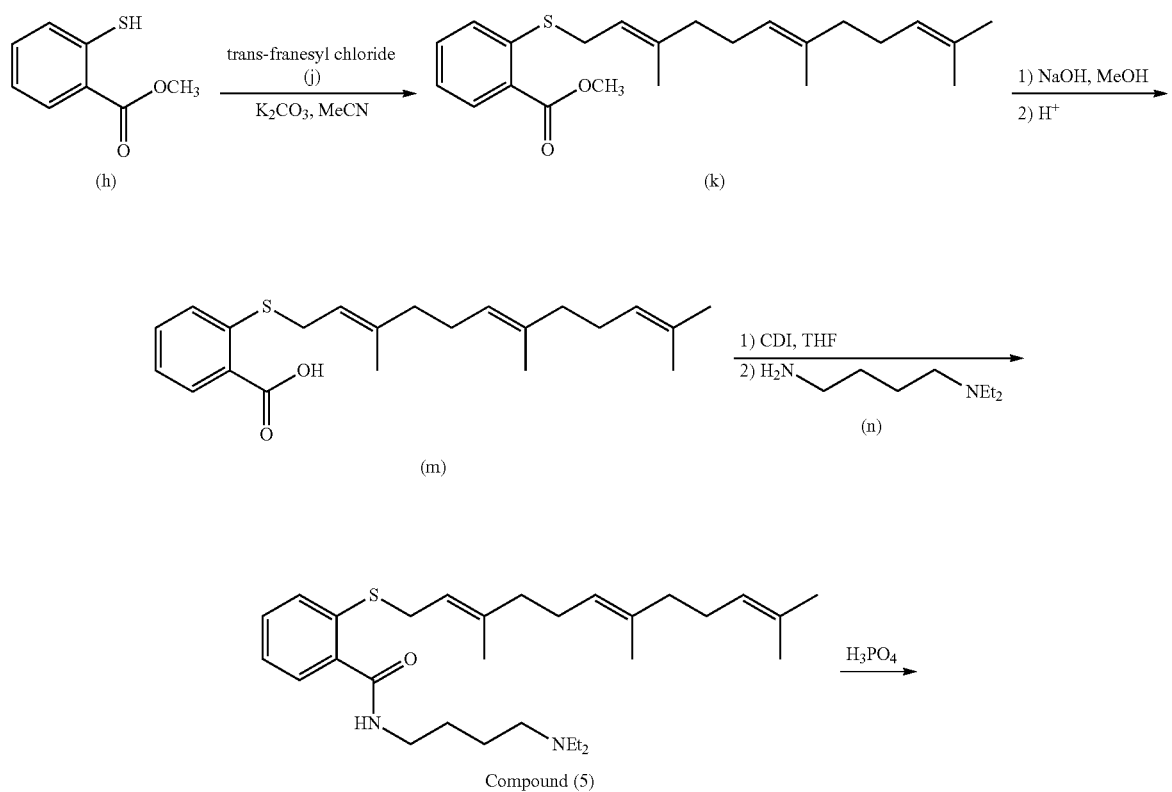

Scheme 3

Compound (5)

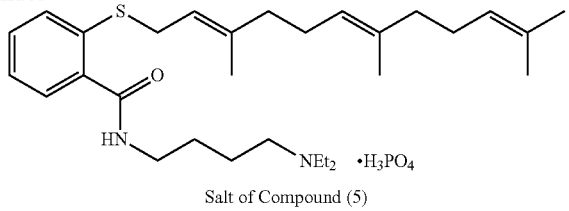

Salt of Compound (5)

Synthesis of intermediate (k): a mixture of compound (h) (4.90 g, 29.2 mmol) and compound (j) (7.1 g, 29.5 mmol, 1.01 eq.) in ACN (150 mL) was refluxed for 12 h to generate a slurry. After the reaction was complete as monitored by HPLC, solvent was evaporated under reduced pressure at room temperature. Then EtOAc (200 mL) and H₂O (60.0 mL) were added to the reaction mixture. The organic layer was washed with H₂O (40.0 mL×2), brine (30.0 mL), dried over MgSO₄, evaporated and purified by flash chromatography (5%-10% EtOAc/heptane) to afford compound (k) (10.5 g) in 96.7% yield.

Synthesis of intermediate (m): to a solution of intermediate (k) (17.2 g) in methanol (150 mL) was added NaOH (80.0 mL, 1.0 N) at room temperature. The resulting mixture was refluxed at 60° C. for 3 h. After the reaction was complete as monitored by TLC, the reaction mixture was evaporated under reduced pressure at room temperature and neutralized with HCl (2.0 N) to pH 5-6. The mixture was extracted with EtOAc (50.0 mL×4). The combined organic layer was washed with brine, dried over MgSO₄, and concentrated in vacuo, affording (m) as a solid (9.9 g, 98.0%). The material was used in the next step without further purification.

Synthesis of compound 5: a mixture of compound (m) (3.59 g, 11.0 mmol) and CDI (2.33 g, 14.3 mmol, 1.30 eq.) in THF (40.0 mL) was stirred at 30-40° C. for 2 h. Compound (m) (2.38 g, 16.5 mmol, 1.5 eq.) in THF (15 mL) was added to the mixture at room temperature slowly. The resulting mixture was stirred at room temperature overnight to give a clear yellowish solution. After the reaction was complete as monitored by HPLC, solvent was evaporated under reduced pressure. Then DCM (100 mL) and H₂O (30.0 mL) were added to the reaction mixture. The aqueous layer was extracted with DCM (40.0 mL×3). The combined organic layer was washed with H₂O (40.0 mL×3), brine (30.0 mL), dried over MgSO₄, evaporated and purified by flash chromatography (0%-15% MeOH/DCM) to afford compound 5 (4.95 g) in 92.7% yield.

Figure 5:
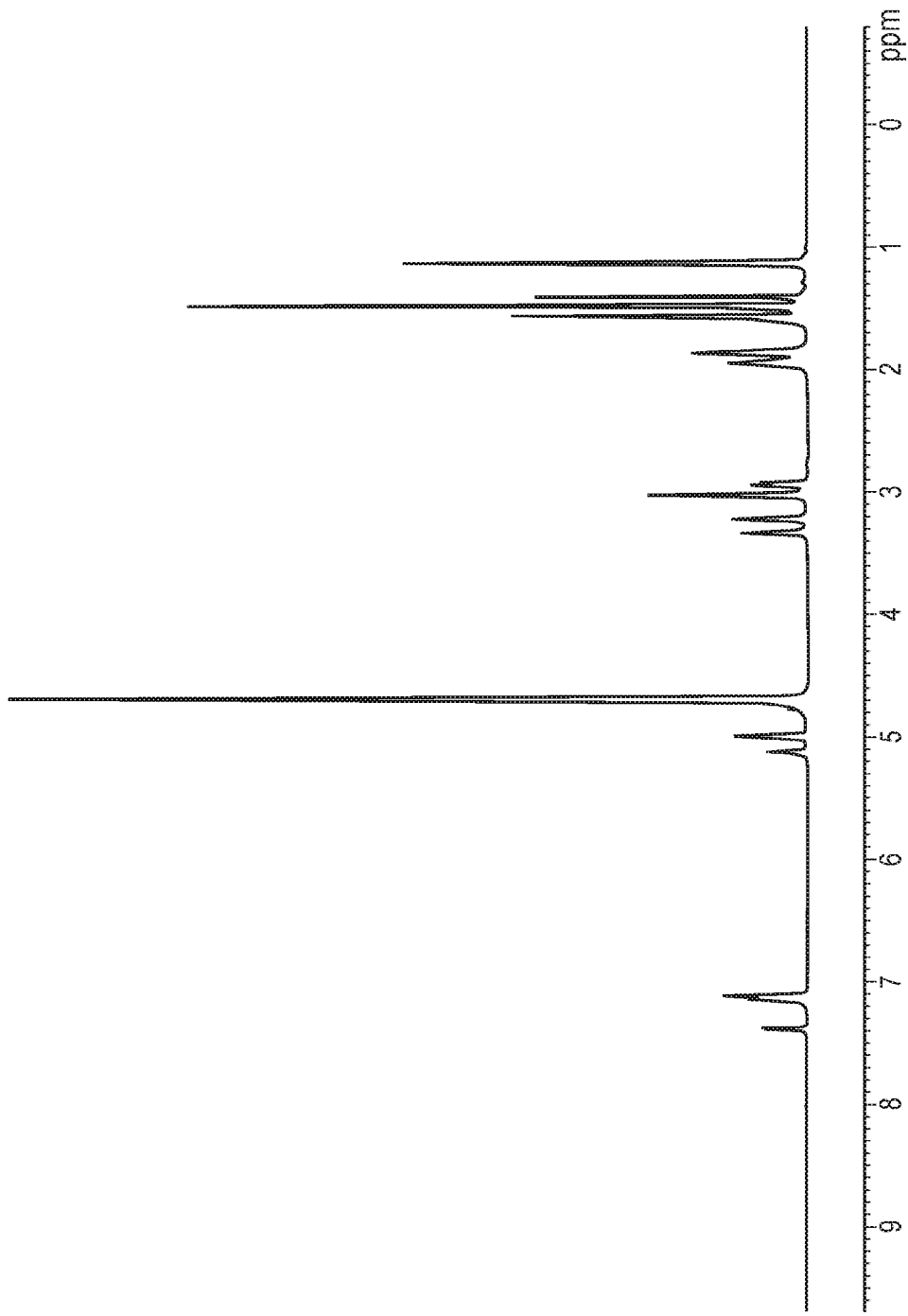
FIG. 5 illustrates the $^1$HNMR spectra of compound 5 salt.
Figure 6:
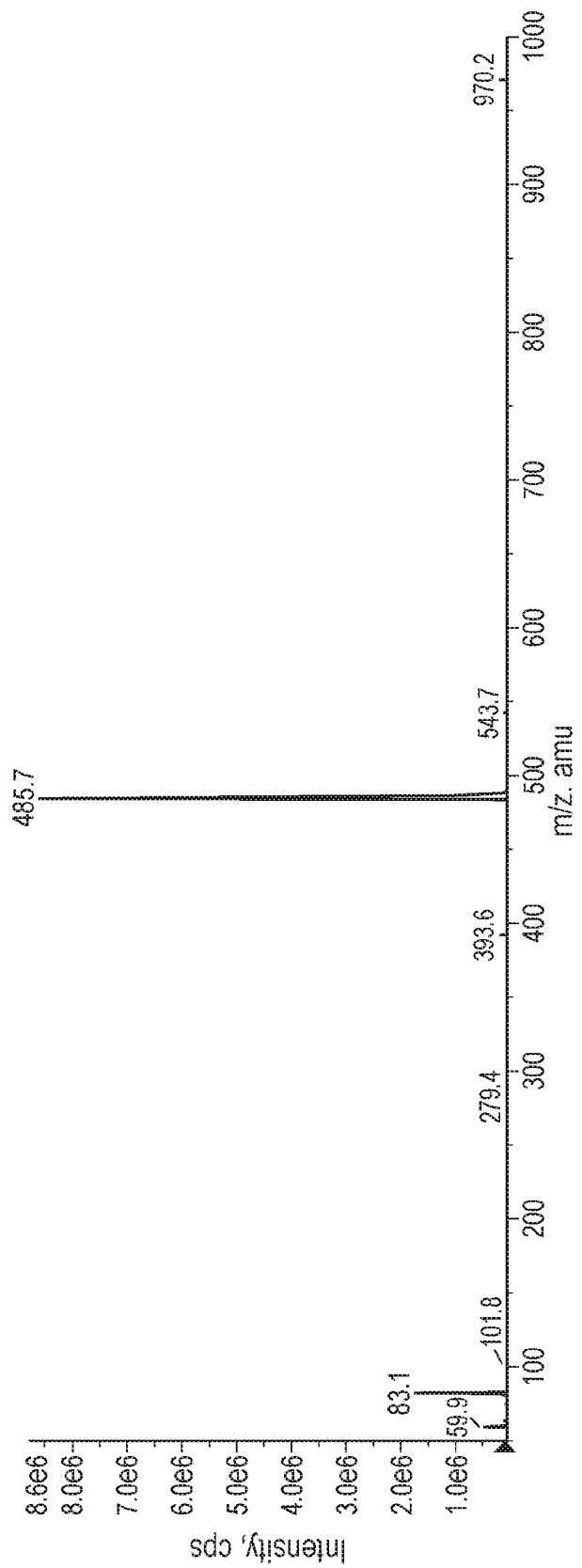
FIG. 6 illustrates the MS of compound 5 salt.

Synthesis of compound 5 salt: to a solution of compound 5 (7.40 g, 15.3 mmol) in EtOAc (25.0 mL) at 0° C. was added phosphoric acid (1.05 mL, 1.0 eq.) in EtOAc (10.0 mL) slowly. Heptanes (500 mL) were added to the above mixture very slowly. The resulting suspension was stirred for 2 h, filtered, washed with heptanes (30.0 mL×3) to afford a white solid. The solid was dried under high vacuum, dissolved in H₂O (80 mL), and then freeze dried to furnish compound 5 phosphate salt as an off-white gummy solid (9.2 g). FIG. 5 illustrates the ¹HNMR spectra of compound 5 salt, and FIG. 6 illustrates the MS of compound 5 salt.

Example 4: Synthesis of Compound 6

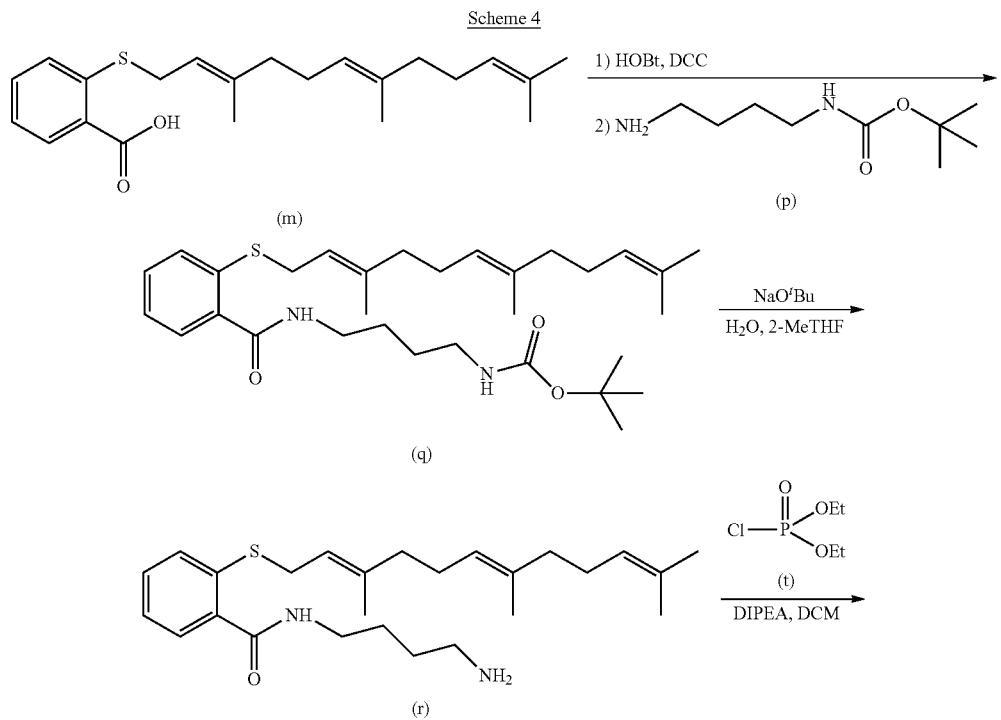

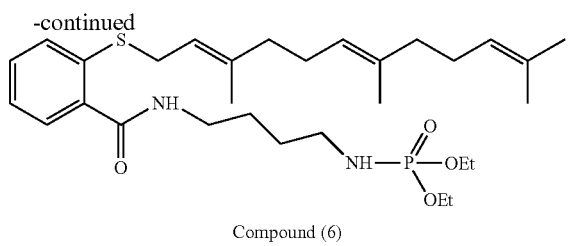

Compound (6)

Synthesis of compound (q): to a mixture of intermediate (m) (5.00 g, 13.95 mmol) and HOBt (1.89 g, 13.95 mmol, 1.0 eq.) in THF (60.0 mL) in an ice bath was added DCC (3.45 g, 16.74 mmol, 1.2 eq.). The resulting slurry was stirred at room temperature for 2 h. Compound (p) (3.15 g, 16.74 mmol, 1.2 eq.) in THF (30.0 mL) was added to this slurry. The reaction mixture was stirred at room temperature overnight, concentrated, then diluted with EtOAc (200 mL), filtered, washed with EtOAc (20 mL×3). The combined organic layer was treated with NaHCO₃ (40.0 mL), NaOH (40 mL, 2.0 N), brine (40 mL×2), dried over MgSO₄, evaporated, and purified by flash chromatography (0%-30% EtOAc/heptane) to afford compound (q) (6.51 g, 88.2%).

Synthesis of compound (r): a suspension of compound (q) (3.86 g, 7.3 mmol), NaOtBu (6.92 g, 72.0 mmol, 10 eq.), H₂O (0.17 mL, 1.0 eq.) in 2-MeTHF (800 mL) was heated to reflux for 15 h. After the reaction was complete, the mixture was cooled in an ice bath, quenched with saturated ammonium chloride (50.0 mL) to adjust pH to 10-11. The aqueous layer was extracted with EtOAc (40.0 mL×4), washed with H₂O (40.0 mL×2), brine (30.0 mL), dried over MgSO₄, evaporated, and purified by flash chromatography (5%-50% MeOH/DCM) to afford compound (r) (2.64 g) in 84.3% yield.

Figure 7:
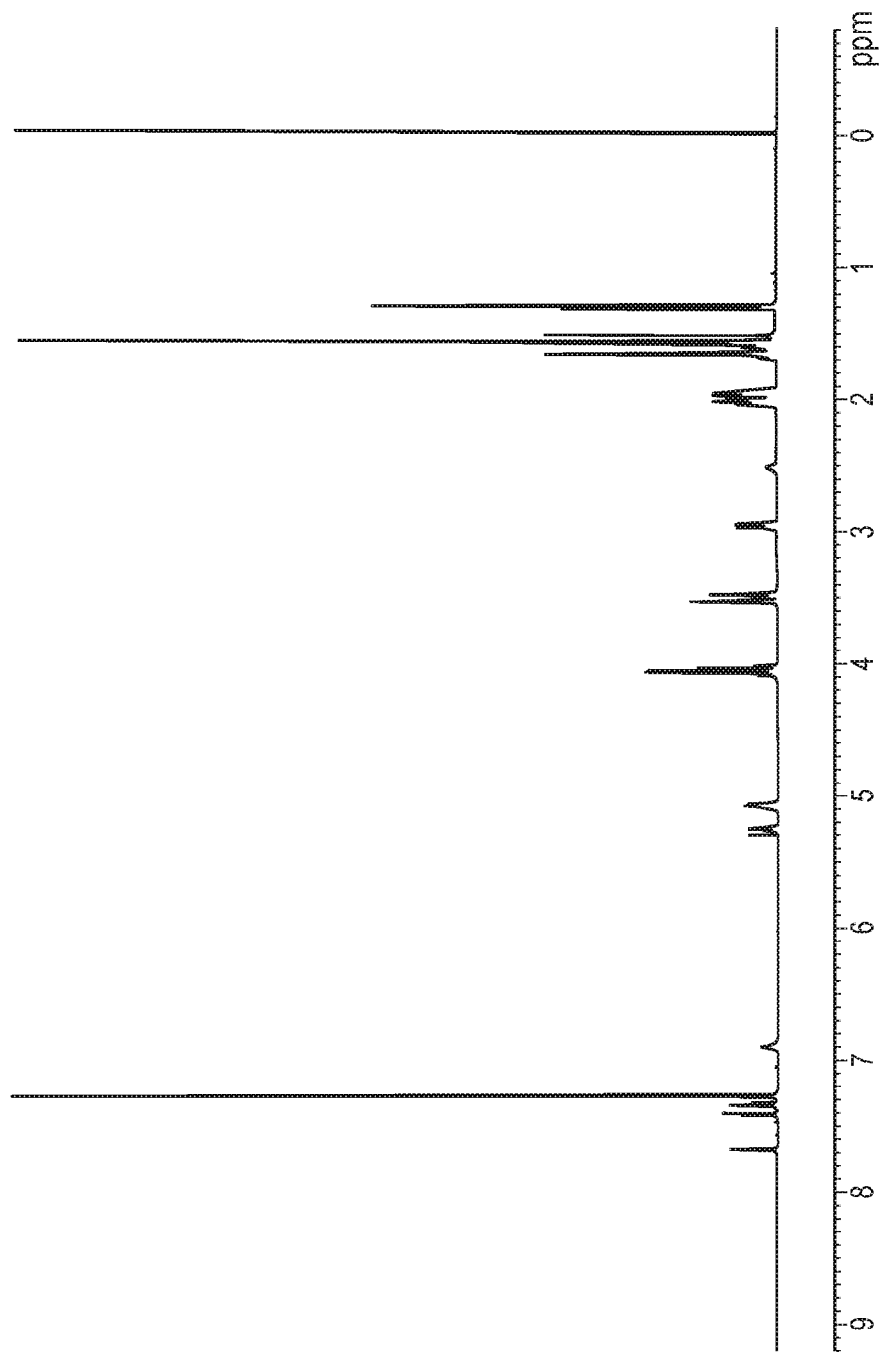
FIG. 7 illustrates the $^1$HNMR spectra of compound 6.
Figure 8:
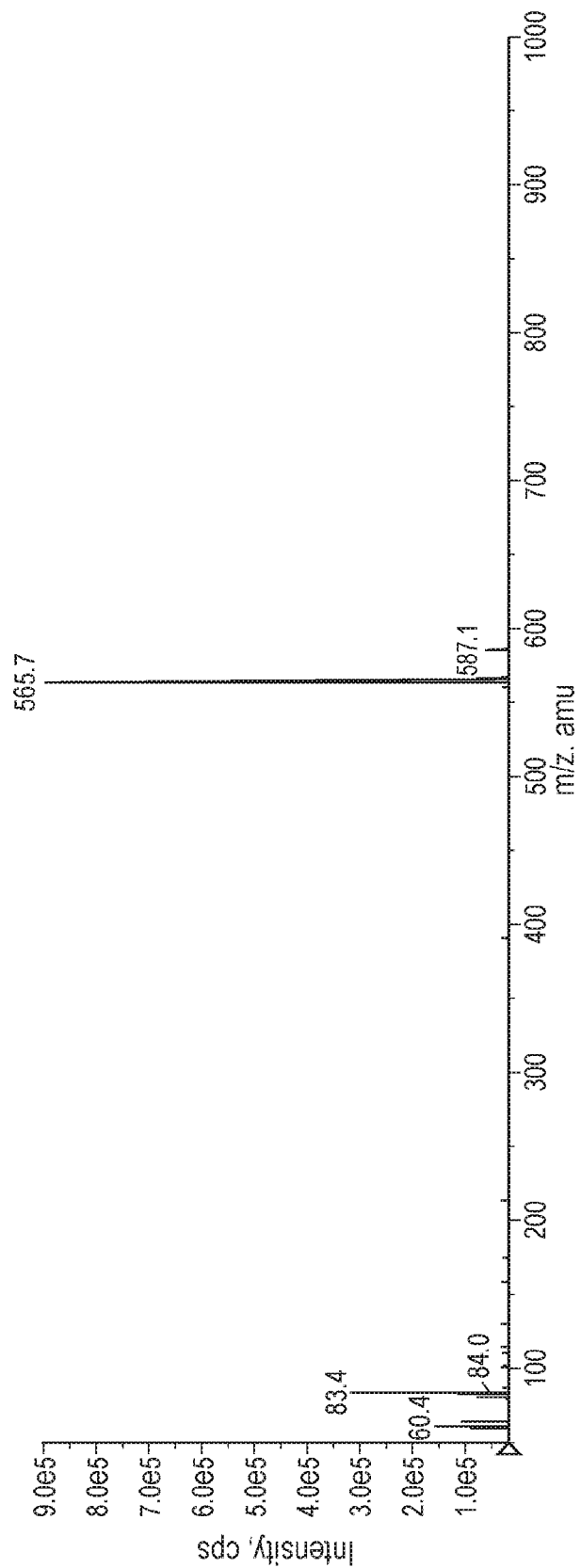
FIG. 8 illustrates the MS of compound 6.

Synthesis of compound 6: to a solution of compound (r) (4.73 g, 11.04 mmol), DIPEA (5.80 mL, 3 eq.) in DCM (80 mL) was added compound (t) (1.92 mL, 1.2 eq.) in an ice bath. The resulting mixture was stirred at room temperature for 2 h. The mixture was evaporated, diluted with EtOAc (150 mL), washed with NaHCO₃ (40.0 mL), H₂O (40.0 mL×3), brine (30.0 mL), dried over MgSO₄, evaporated, purified by different solvent systems (0%-5% MeOH/DCM) and (50%-100% EtOAc/heptane) to give product 6 (5.05 g) as a light yellow oil in 83.7% yield. FIG. 7 illustrates the ¹HNMR spectra of compound 6, and FIG. 8 illustrates the MS of compound 6.

Example 5: Synthesis of Compound 7

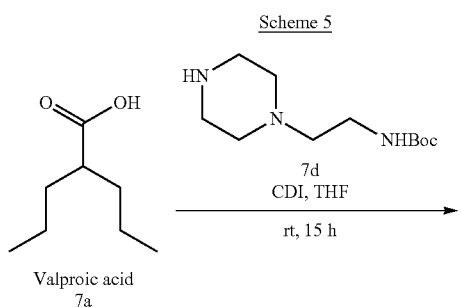

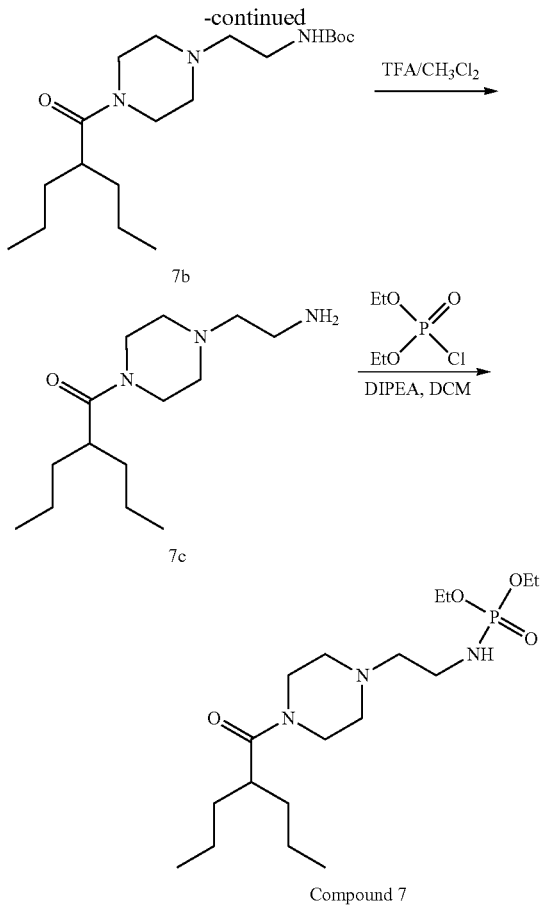

Step-1: Synthesis of tert-butyl (2-(4-(2-propylpentanoyl)piperazin-1-yl)ethyl)carbamate (7b): To a stirred solution of Compound 7a (22.0 g, 15.22 mmol, 1.0 eq.) in THF (170 mL) was added CDI (28.5 g, 17.56 mmol, 1.0 eq.) at rt. The reaction mixture was stirred at room temperature for 2 h. After 2 h, Compound 7d (45.0 g, 19.86 mmol, 1.3 eq.) in THF (170 mL) was added drop wise to the reaction mixture. After addition was complete the reaction mixture was stirred at rt for 18 h (The reaction mixture was monitored by TLC). After completion of reaction, the reaction mixture was concentrated under reduced pressure to get residue. The residue was suspended with water (300 mL) and extracted with EtOAc (2×400 mL). The combined organic layer was dried over sodium sulfate and filtered. The solvent was concentrated under reduced pressure to get the crude. The crude was purified through basic silica gel column chromatography using Ethyl acetate: Hexane (30:70) as an eluent to get Compound-7b (34.0 g) as a pale-yellow color liquid. ¹H-NMR (400 MHz, CDCl₃): δ 5.01 (bs, 0.8H), 3.67 (t, J=9.6 Hz, 2H), 3.56 (t, J=9.6 Hz, 2H), 3.24 (t, J=5.2 Hz, 2H), 2.66-2.52 (m, 1H), 2.49-2.40 (m, 6H), 1.65-1.62 (m, 2H), 1.47 (s, 9H), 1.41-1.34 (m, 3H), 1.30-1.20 (m, 4H), 0.88 (t, J=7.2 Hz, 6H).

Step-2: Synthesis of 1-(4-(2-aminoethyl)piperazin-1-yl)-2-propylpentan-1-one (7c): To a stirred solution of Compound 7b (32.0 g, 90.14 mmol, 1.0 eq.) in DCM (425 mL) was added TFA (71.9 mL, 63.09 mmol, 7.0 eq.) drop wise at 0° C. for 10 min. The reaction mixture was stirred at rt for 2.5 h. After 2.5 h, the reaction mixture was concentrated under reduced pressure to get residue. The obtained residue was co-distilled with toluene (2×60 mL). The obtained reside was washed with Di Ethyl Ether and dried under vacuum to get Compound-7c. TFA salt. Which was dissolved in mixture of dichloromethane:water (9:1) and NaHCO$_3$ (64 g, 2 gram equiv.) was added and stirred for 30 min. After 30 min, the reaction mixture was filtered, solvent was dried over Na$_2$SO$_4$ and filtered. The solvent was concentrated under reduced pressure to get the get Compound-7c (32.0 g) as a colorless liquid. $^1$H-NMR (400 MHz, CD$_3$OD): δ 3.90-3.80 (m, 4H), 3.37-3.33 (m, 2H), 3.32-3.30 (m, 2H), 3.28-3.10 (m, 4H), 2.87-2.83 (m, 1H), 1.62-1.53 (m, 2H), 1.45-1.38 (m, 2H), 1.37-1.17 (m, 4H), 0.90 (t, J=7.2 Hz, 6H).

Step-3: Synthesis of diethyl (2-(4-(2-propylpentanoyl) piperazin-1-yl)ethyl)-phosphoramidate (Compound 7): To a stirred solution of Compound 7c (12.0 g, 47.05 mmol, 1.0 eq.) in DCM (384 mL) was added DIPEA (18.25 g, 14.11 mmol, 3.0 eq.) at rt over a period of 20 min. After 20 min, the reaction mixture was cooled at 0° C., diethyl chlorophosphate (9.97 g, 56.47 mmol, 1.0 eq.) was added drop wise over a period of 10 min at 0° C. The reaction mixture was stirred at rt for 4 h. Reaction was monitored by TLC. After completion of reaction, the reaction mixture was concentrated under reduced pressure to get the residue. The residue was dissolved in EtOAc (800 mL) and extracted with saturated NaHCO$_3$ solution (2×250 mL). The organic layer was dried over sodium sulfate and filtered. The solvent was concentrated under reduced pressure to get the crude. The crude was purified by basic silica gel column chromatography using MeOH: DCM (2:98) as an eluent to get the compound 7 (6.0 g) as a light brown color liquid in pure form. $^1$H-NMR (400 MHz, CDCl$_3$): δ 4.10-4.05 (m, 4H), 3.67-3.55 (m, 2H), 3.40 (bs, 1H), 3.04-2.91 (m, 2H,), 2.54-2.52 (m, 1H), 2.50-2.43 (m, 6H), 1.65-1.63 (m, 2H), 1.41-1.29 (m, 9H), 1.28-1.21 (m, 4H), 0.88 (t, J=7.2 Hz, 6H). $^{31}$P-NMR (161.9 MHz, CDCl$_3$): δ 9.16

Example 6: Cancer Growth Inhibition

Exemplary compounds inhibit the growth of cancer. The therapeutic efficacy of compounds 2, 5, and 6 was assessed in human and murine cell lines of varied tissue origin, and their 24 hr 50% inhibitory concentration was determined by following standard methodologies. Typical results are shown in the Table 5, indicating a broad anticancer effect.

TABLE 5

| Compound | 24 hr IC$_{50}$ (µM) | | | | |
|---|---|---|---|---|---|
| | SKOV-3 ovarian cancer | HCT116 colon cancer | RAW264 murine macrophage | AGS gastric cancer | A549 lung cancer |
| 2 | 480 | 460 | 160 | 306 | 400 |
| 5 | 9 | 10 | 5 | 14 | 19 |
| 6 | 26 | 7 | 6 | 15 | 31 |

Ovarian cancer cells were studied in greater detail using the following ovarian cancer cell lines: SKOV-3, OVCAR3, A2780 (and two cell lines derived from it, A2870cis that is resistant to cisplatin, and A2870ADR that is resistant to doxorubicin (Adriamycin)), and HEY (sensitive to paclitaxel (Taxol), and its derivative HEY-T30 that is Taxol-resistant). Compounds 5 and 6 potently inhibited the growth of these cancer cell lines. Table 6 summarizes the results obtained with compound 6. Similar results were obtained with compound 5.

TABLE 6

| Cell line | 24-h IC$_{50}$ µM mean ± SEM |
|---|---|
| SKOV-3 | 26.0 ± 3.2 |
| OVCAR3 | 22.0 ± 1.6 |
| A2780 | 20.3 ± 1.4 |
| A2780cis platinum resistant | 20.5 ± 1.1 |
| A2780ADR Adriamycin resistant | 21.3 ± 0.8 |
| HEY Taxol sensitive | 25.3 ± 0.3 |
| HEY T30 Taxol resistant | 24.6 ± 0.6 |

Example 7: In Vivo Cancer Growth Inhibition

The ability of compound 5 to inhibit the growth of human ovarian cancer cell xenografts in nude mice was determined. A mouse model that recapitulates the features of peritoneal spread was used, the peritoneal spread being the clinically most relevant presentation of ovarian cancer. In this model, luciferase-expressing ovarian cancer cells are injected intraperitoneally (ip) into nude mice. Multiple tumors grow in the peritoneal cavity and their growth is monitored periodically using the IVIS Lumina II imaging system following the intraperitoneal administration of luciferin, the substrate of luciferase. The luciferase gene was transfected into SKOV-3 cells, and 2×10$^6$ cells were intraperitoneally injected into mice. Two weeks later, when tumors had grown, mice treatment was started by intraperitoneally injecting compound 5, 15 mg/kg or vehicle (corn oil), once a day, six days a week (n=10 mice/group).

Figure 9:
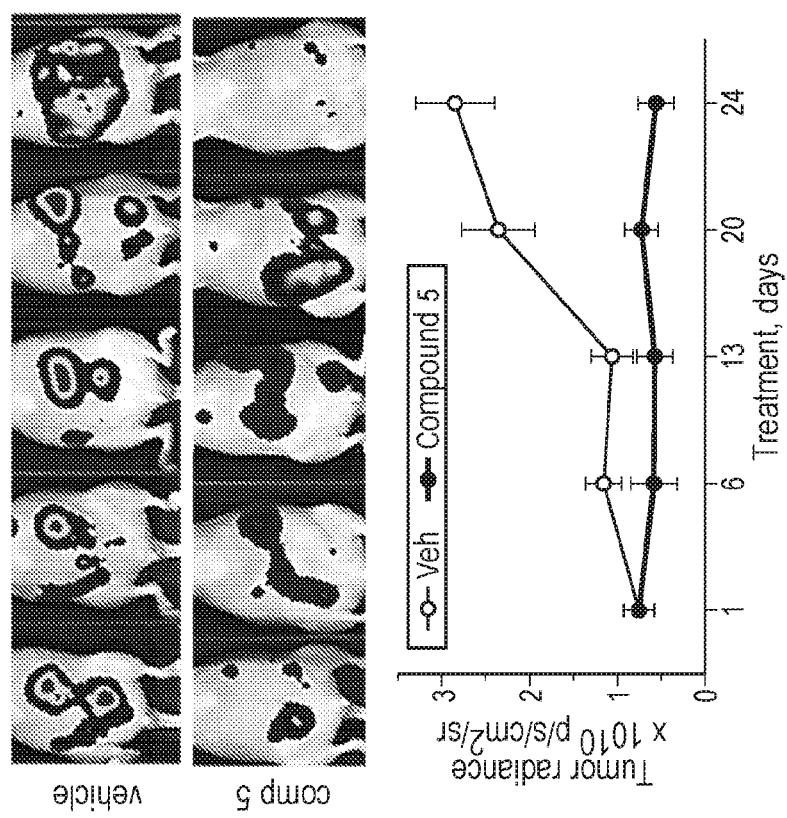
FIG. 9 illustrates images and tumor growth curves in animals treated with compound 5 vs. control animals. Luciferase expressing SKOV-3 cells were implanted into the peritoneal cavity of nude mice and treated with compound 5 or vehicle. Compound 5 suppresses the growth of intraperitoneal SKOV-3 tumors.

As shown in FIG. 9, compound 5 profoundly inhibited the growth of the ip tumors. On day 24, compound 5 reduced tumor volume by 153% compared to control (p<0.001). When the tumor volume of the compound 5 treated mice at the end of the study is compared to that of the day when treatment started (baseline), compound 5 caused 53% tumor regression, with 3 out of 10 mice having barely detectable tumors by imaging and no tumors visible at necropsy. Compound 6 produced virtually identical results.

Compound 6 administered to the same animal model at the dose of 100 mg/kg once a day, six days a week, produced virtually identical results with compound 5. Compound 6 was also efficacious against chemotherapy-resistant ovarian cancer. This was demonstrated in human ovarian cancer cell-line subcutaneous xenografts in nude mice. The effect of compound 6 in cisplatin resistant (A2780cis) and doxorubicin (Adriamycin) resistant (A2780ADR) tumors was studied. Briefly, each of these cell lines was subcutaneously inoculated into athymic nude mice and when the tumor size reached 100-200 mm$^3$, compound 6 150 mg/kg/day or its vehicle were given i.p. After 11 days of treatment, for the cisplatin-resistant tumors the tumor volume of the vehicle group was 2388±127 mm³ and for compound 6 group 1032±108 mm³ (mean±SEM; P<0.02); while for the doxorubicin-resistant tumors these values were: vehicle group=1369±337 mm³ and compound 6 group=396±182 mm³ (P<0.02).

Example 8: In Vivo Efficacy Against Chemotherapy-Resistant Ovarian Cancer

Figure 10:
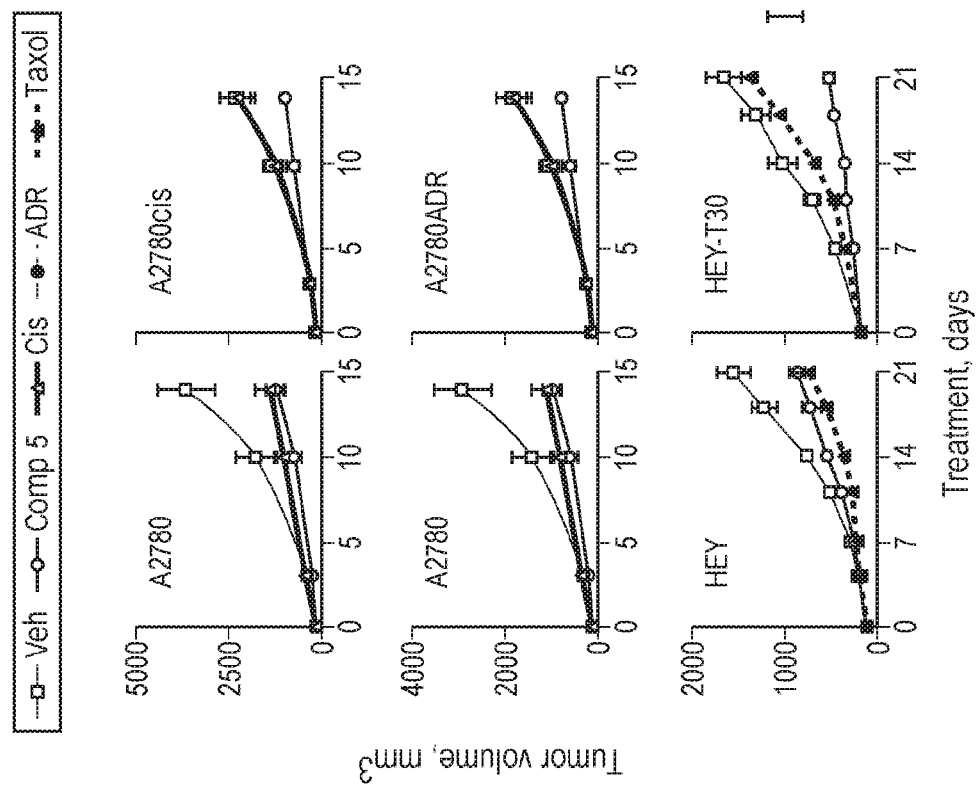
FIG. 10 illustrates tumor growth curves in animals treated with compound 5 vs. control animals. A2780 and HEY are chemotherapy sensitive tumors, while the A2780cis are resistant to cisplatin, A2780ADR are resistant to doxorubicin (Adriamycin) and HWY-T30 are resistant to paclitaxel. Compound 5 inhibited tumor growth in both chemotherapy sensitive and resistant tumors, in contrast to the conventional chemotherapeutic agents. Values: mean±SD.

To determine whether compound 5 is efficacious against chemotherapy-resistant ovarian cancer, three pairs of sensitive and resistant human ovarian cancer cell lines were grown as subcutaneous xenografts in nude mice and treated as summarized in FIG. 10. These cell lines were: A2780, sensitive to both cis-platinum and Adriamycin (doxorubicin); A2780cis, resistant to cis-platinum; A2780ADR, resistant to Adriamycin: HEY, sensitive to Taxol; HEY-T30, resistant to Taxol. When tumor volume was about 150 mm³, mice were treated as indicated in the figure. The treatments administered were: vehicle control; compound 5, 15 mg/kg/day six days a week, ip; cis-platinum 5.5 mg/kg, one time a week ip; Adriamycin 3 mg/kg twice a week ip; and Taxol 20 mg/kg twice a week ip. As shown in FIG. 10, compound 5 and cis-platinum suppressed the growth of the platinum-sensitive xenografts with equal efficacy. In the platinum-resistant xenografts, compound 5 was as efficacious as in the platinum sensitive xenografts, whereas platinum failed to significantly inhibit tumor growth. The same pattern of response was observed for compound 5 vs. Adriamycin, and compound 5 vs. Taxol. These results, consistent with the in vitro data, demonstrate the ability of compound 5 to overcome drug resistance in ovarian cancer, a critical determinant of the clinical outcome in this often lethal malignancy.

Example 9. The Mechanism of the Anticancer Effects of Compounds 5 and 6

Further studies devaluated the mechanism of action of exemplary compounds 5 and 6, demonstrating that they are distinct from each other and also from other known compounds.

Figure 11:
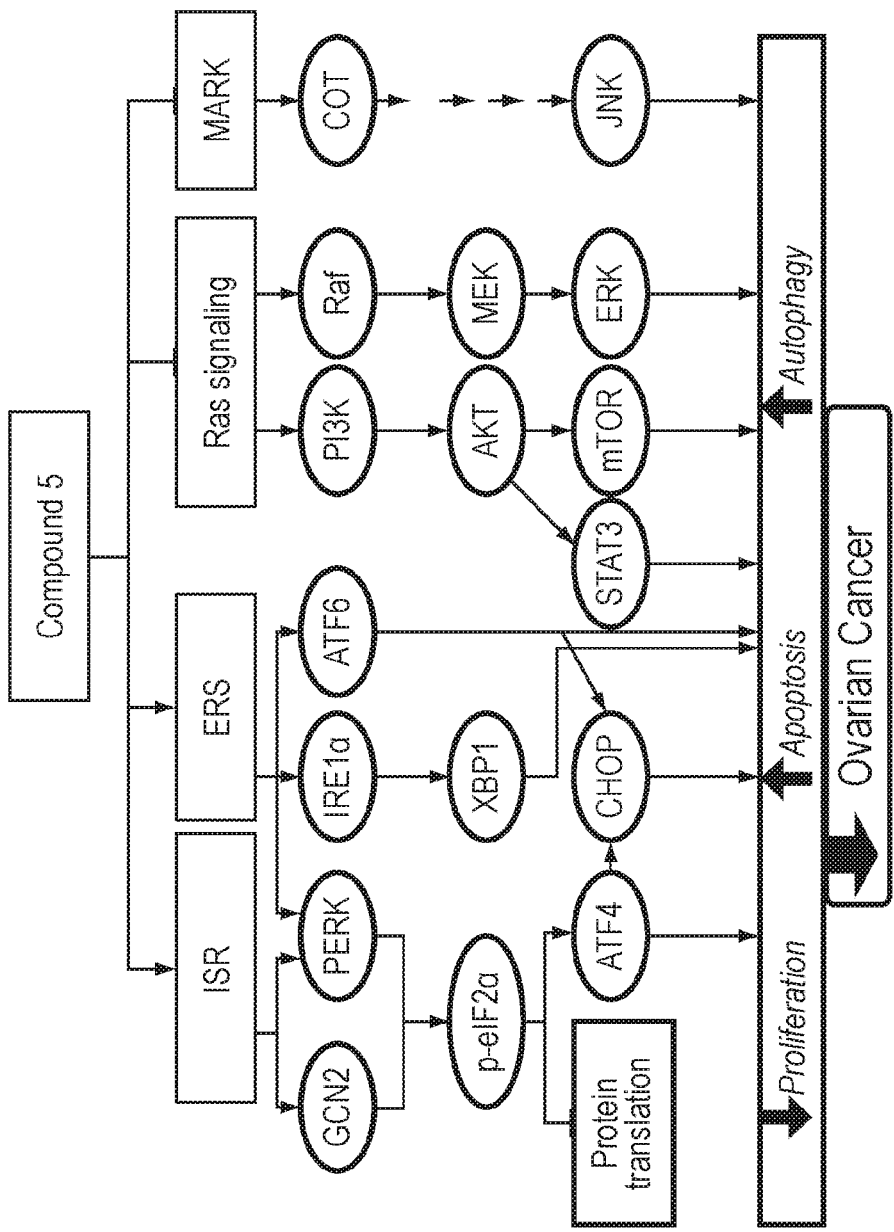
FIG. 11 illustrates the mechanism of the anti-ovarian cancer effect of compound 5. The main signaling pathways modulated by compound 5 are shown. Pointed arrows (→) indicate stimulation; T-shaped arrows indicate inhibition (AKT: Ak strain transforming; also known as Protein Kinase B; ATF4: Activating transcription factor 4; ATF6: Activating transcription factor 6; CHOP: CCAAT-enhancer-binding protein (C/EBP) homologous protein; COT: Cancer osaka thyroid; ERK: Extracellular signal-regulated kinases; ERS: Endoplasmic reticulum stress response; GAPDH: Glyceraldehyde 3-phosphate dehydrogenase; GCN2: General control nonderepressible 2; IRE1α: Inositol-requiring enzyme 1α; ISR: Integrated stress response; JNK: c-Jun N-terminal kinase; mTOR: The mammalian target of rapamycin; MAPK: Mitogen-activated protein kinases; MEK: Mitogen-activated protein kinase kinase; p-eIF2α: phospho-Eukaryotic translation initiation factor 2A; PERK: Protein kinase RNA (PKR)-like endoplasmic reticulum kinase; PI3K: Phosphatidylinositol 3 kinase; Raf: Rapidly accelerated fibrosarcoma; Ras: Retrovirus-associated DNA sequences; STAT3: Signal transducer and activator of transcription 3; XBP1: X-box binding protein).
Figures 12A, 12B, 12C:
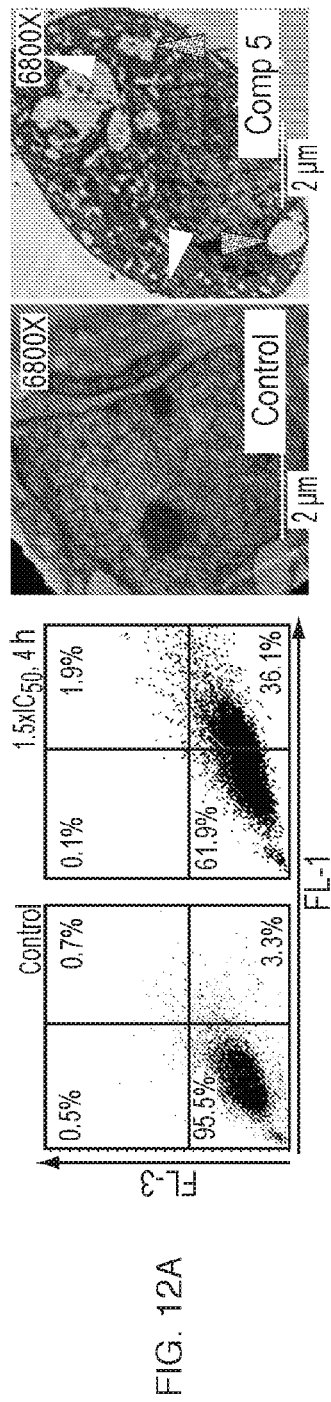
FIGS. 12A-12C and FIGS. 13A-13C illustrate key findings related to the mechanism of action of compound 5 against ovarian cancer. The studies shown here were performed in SKOV-3 human ovarian cancer cells.
Figure 13A:
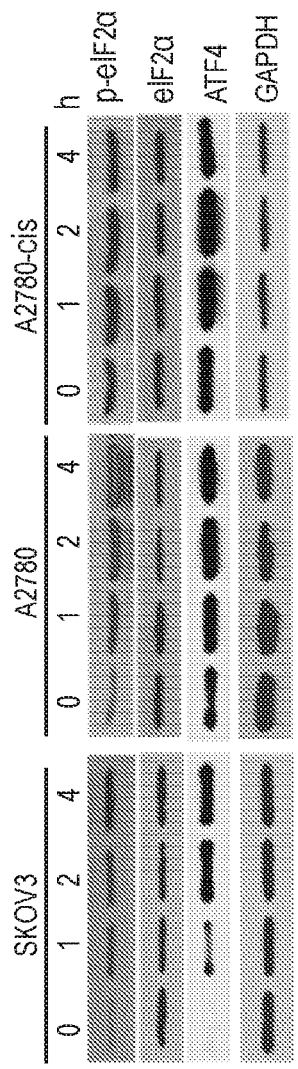
Figure 13B:
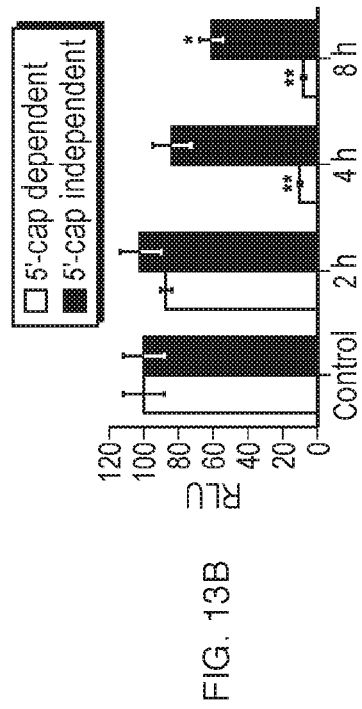
Figure 13C:
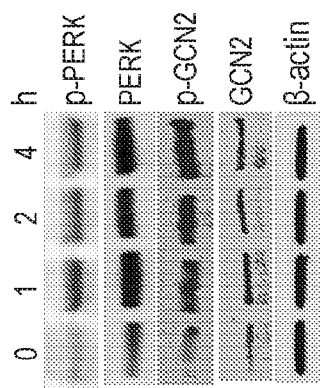

The dominant mechanistic effect of compound 5 is the induction of the integrated stress response (ISR) and endoplasmic reticulum stress (ERS). These stresses are of such magnitude that they exceed the pro-survival threshold, triggering cell death through autophagy and apoptosis, a therapeutically useful outcome. Normal cells are spared this effect. This mechanism of action operates in both sensitive and resistant cells and may explain the ability of compound 5 to overcome resistance to chemotherapy. This mechanism is summarized in FIG. 11, while FIGS. 12A-12C and 13A-13C illustrate the key findings that support this mechanism.

Figure 14:
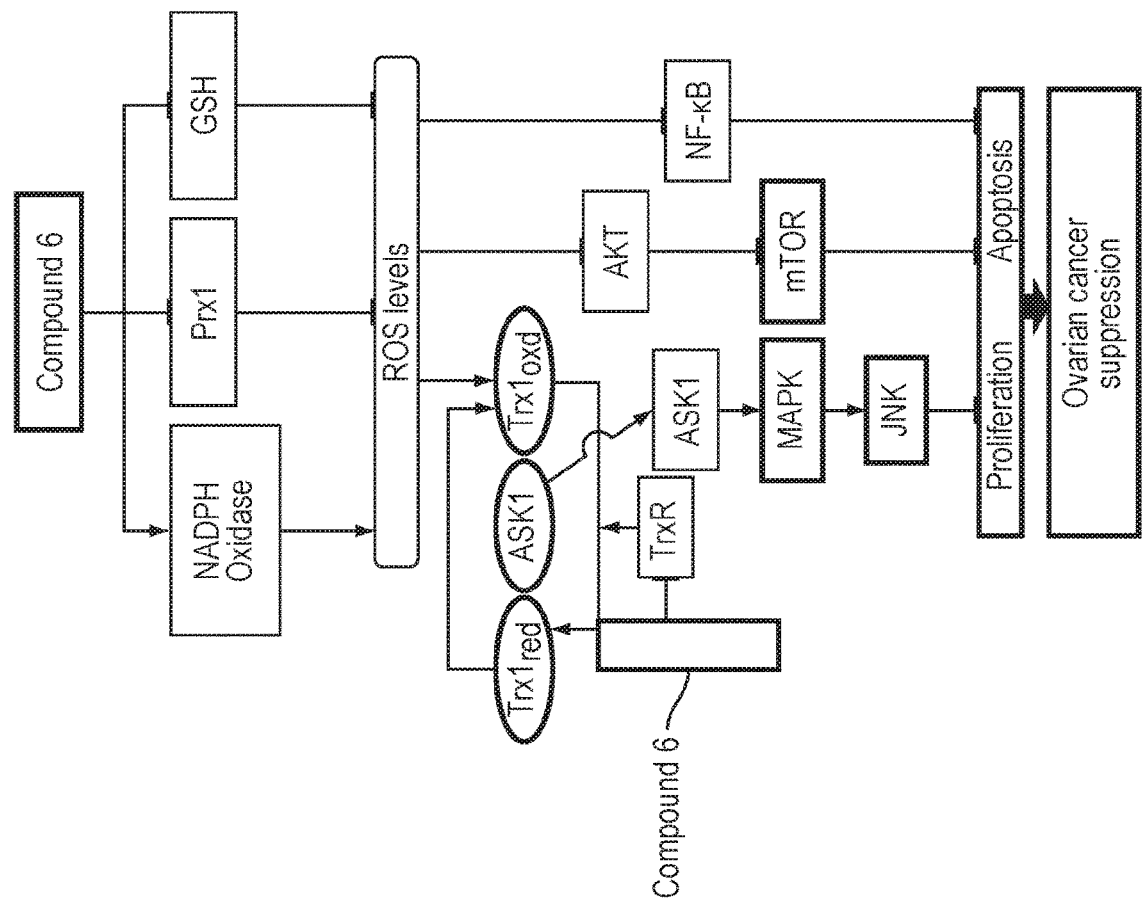
FIG. 14 illustrates key mechanistic steps in the induction of oxidative stress by compound 6 in SKOV-3 ovarian cancer cells and signaling through redox-sensitive pathways. (AKT: Ak strain transforming; also known as Protein Kinase B; ASK1: apoptosis signal-regulating kinase 1; C6: compound 6; JNK: c-Jun N-terminal kinase; GAPDH: Glyceraldehyde 3-phosphate dehydrogenase; GSH: glutathione; MAPK: mitogen-activated protein kinase; mTOR: the mammalian target of rapamycin; NADPH: nicotinamide adenine dinucleotide phosphate; NF-κB: nuclear factor kappa-light-chain-enhancer of activated B cells; p38: mitogen-activated protein kinase; Prx1: peroxiredoxin 1; Prx-SO$_3$: peroxiredoxin-sulfur trioxide; ROS; reactive oxygen species; Trx1: thioredoxin 1; TrxR: thioredoxin reductase; TTFA: thenoyltrifluoroacetone).
Figure 16A:
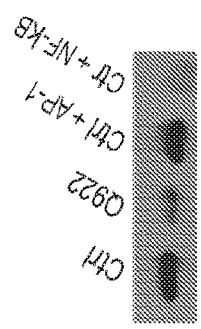
FIG. 16A. Compound 6 suppressed the activation of NF-κB-DNA determined by electrophoretic mobility shift assay in nuclear fractions of cells. To determine the specificity of the NF-κB transcription factor-DNA complex, the control nuclear fraction was incubated in the presence of 100-fold molar excess of unlabeled oligonucleotide containing the consensus sequence for either the specific (+NF-κB) or a non-specific (+AP-1) transcription factor.
Figure 16B:
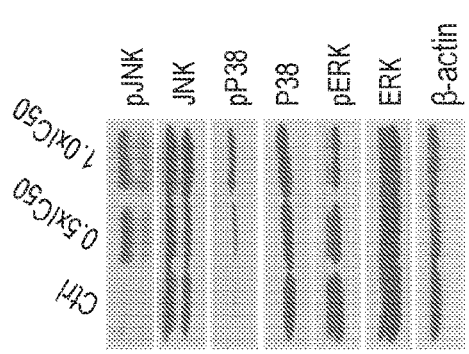
FIG. 16B. MAPK activation in response to compound 6 was determined by immunoblotting cell lysates as indicated.
Figure 16C:
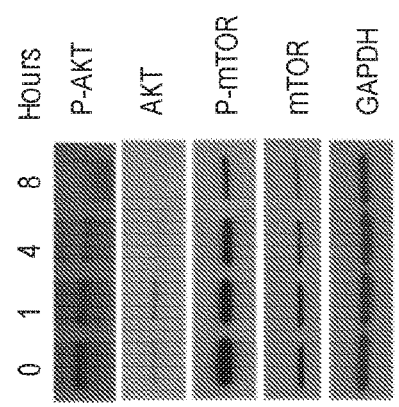
FIG. 16C. AKT and mTOR activation by compound 6 was determined by immunoblotting cell lysates as indicated.

Compound 6 has an entirely different mechanism of action, based predominantly on the induction of a different type of stress in ovarian cancer cells, namely oxidative stress. Oxidative stress, depending on its degree, can induce cancer cell death, mainly through apoptosis, thus mediating the effect of anticancer agents. This mechanism is summarized in FIG. 14, FIG. 15, and FIG. 16, which illustrate the key findings that support this mechanism.

Example 10. Synergy with Chemotherapeutic Agents

Figure 17:
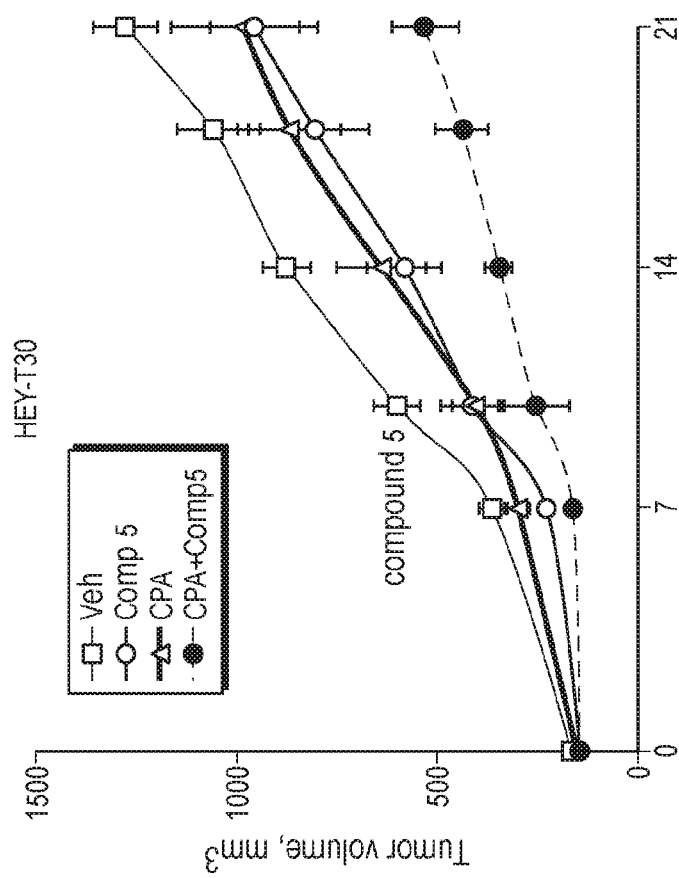
FIG. 17 illustrates the synergistic effect between compound 5 and cyclophosphamide (CPA) in the inhibition of Taxol-resistant human ovarian cancer cell (HEY-T30) xenografts. Animals treated with either or both compounds, responded similarly to compound 5 and CPA at the doses used. Their combination produced tumor inhibition greater than the sum of each drug alone, i.e., synergistic inhibition.

It was further demonstrated that at low doses an exemplary compound 5 synergizes with low doses of cyclophosphamide to inhibit the growth of chemotherapy-resistant ovarian cancer. As shown in FIG. 17, subcutaneous xenografts in nude mice of the Taxol resistant human ovarian cancer cell line HEY-T30 were treated with vehicle control or compound 5 10 mg/kg/day six days a week ip, or cyclophosphamide 10 mg/kg six days a week orally or both of them at the same doses. Compared to control, neither agent alone produced significant imbibition of tumor growth. Their combination, however, not only inhibited significantly tumor growth (58% on day 21), but its magnitude established synergy as it exceeded the sum of each drug alone (26% and 23%, respectively, on day 21).

Furthermore, in vitro studies using cultured human cancer cells revealed the synergistic action of exemplary compounds with various anticancer agents. For example, compound 5 synergizes with tamoxifen to essentially eliminate (when tamoxifen is administered prior to compound 5) or significantly reduce (if given concurrently with, or prior to, tamoxifen) the growth of MIA PaCa2 human pancreatic cancer cells. Additionally, synergy has been documented between compounds 5 and 6 individually and several chemotherapeutic and other agents, including but not limited to various camptothecins (e.g., camptothecin 11), resveratrol, gemcitabine, docetaxel, curcumin, progesterone, and methotrexate. Such synergy concerned the ability of these combinations to markedly suppress the growth of various human cancer cell lines originating in the pancreas, lung and other tissues. Furthermore, extremely efficacious was the combination of compounds 5, 6 and tamoxifen in completely suppressing the growth of K-ras mutant human pancreatic cancer cell lines.

Example 11: Exemplary Compounds Inhibit VEGF Expression

Pathological angiogenesis is a hallmark of cancer. Tumor growth and metastasis rely heavily on development of new blood vessels. The vascular endothelial growth factor (VEGF) is the most prominent molecule involved in vascular growth. VEGF promotes the formation of tumor blood vessels, and tumors cannot grow beyond a critical size without adequate blood supply. Pathological angiogenesis is also important in diabetic retinopathy, a common cause of blindness. VEGF plays a critical role in the diabetic retinopathy and is a therapeutic target.

The effect of compounds 2, 5, and 6 on VEGF production was examined. For example, SKOV-3 ovarian cancer cells grown in culture were treated with compound 5 1×IC$_{50}$ for up to 24 h. Secreted VEGF was assayed in the culture medium by ELISA (R&D Systems). Compound 5 time-dependently suppressed VEGF-A levels, reaching 80% by 6 hr and 100% at 24 hr. Similar results were obtained with additional ovarian cancer cell lines. For example, at 24 h, the reduction of secreted VEGF-A over the corresponding controls was: OVCAR3=100%, A2780=86%, A2780cis=100%, and A2780ADR=100%. Compound 5 suppressed VEGF-B by 90-92% compared to control. The anti-VEFG effect of Compound 5 is as strong in the drug-resistant as in the drug-sensitive cell lines. Compound 6 gave similar results.

Example 12: Exemplary Compounds Inhibit the Activation of Mutant K-Ras

Figure 18A:
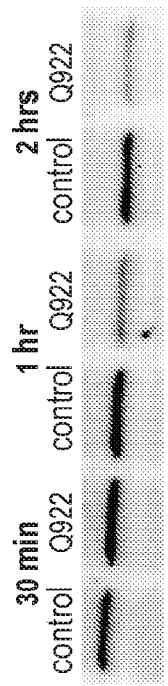
FIG. 18A: Compound 6 suppressed of K-Ras activation. Cells with mutant K-Ras were treated with compound 6 $1.5 \times IC_{50}$ for the respective time periods. K-Ras activity was determined by Ras pull-down (Thermo Scientific; following vendor instructions). K-Ras activation is suppressed 37% at 1 hr and 88% at 2 hrs compared to respective controls.
Figure 18B:
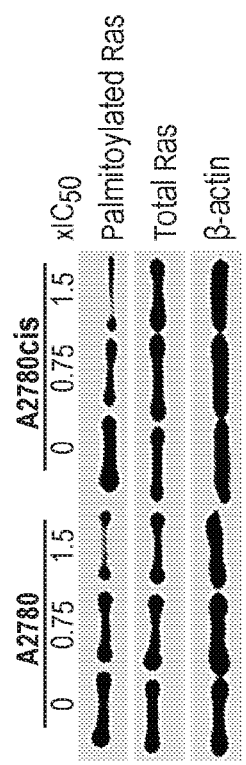
FIG. 18B: Compound 5 suppressed the palmitoylation of Ras in A2780 and A2780cis (resistant to cisplatin) ovarian cancer cells. Palmitoylation is detected by removing S-palmitate groups from proteins, creating new free thiols (where the palmitic acid group used to be) and capturing the previously S-palmitoylated proteins on a resin, using a commercial kit (Badrilla, Leeds, UK). Ras was detected in the eluate by immunoblot.

An unexpected property of the compounds of the invention is that they strongly inhibit the activation of mutant K-Ras. This effect may be particularly useful in types of cancer characterized by K-Ras mutation such as, for example, pancreatic, lung and ovarian cancer. FIG. 18A illustrates the inhibition of K-Ras activation by compound 6. Notably and unexpectedly, exemplary compound 5 suppressed the activation of mutant K-Ras not by the mechanism by which compound 6 inhibited it, but by suppressing its palmitoylation (FIG. 18B), a lipid modification that is required for Ras action in driving cancer. This property of compound 5 is not shared for example by compound 6 or phosphosulindac.

Example 13: Exemplary Compounds Reach the Posterior Chamber of the Eye

Biodistribution of the compounds of Formula A-D-Y is determined after topical administration as in vivo eye drops to the eyes of New Zealand white rabbits. Biodistribution of the compound of Formula A-D-Y can also be determined after topical administration to human cadaveric eyes, preserved on ice and used within 2 h from removal from the donors. The anterior surface of the human eye (corresponding to an area slightly larger than the palpebral fissure) is brought into direct contact with a formulation of the invention and incubated for about 10 min at 37° C. The eye is then rinsed with 10% dimethylsulfoxide (DMSO) to remove residual PS from the surface of the eye without damaging ocular tissue, and incubated in PBS for 60 min. At specific time intervals, ocular tissues are dissected and Formula A-D-Y compounds levels determined by HPLC.

The pharmacokinetics and biodistribution of compounds 1, 2, and 5 in the eye of rabbits were determined. Each of these compounds was dissolved in phosphate buffered saline (PBS) and used as eye drops. The eye drops were sterilized before application to rabbits by filtration through a 0.2 μm membrane. New Zealand rabbits were each administered three 25 μl eye drops, one drop every 5 min, and euthanatized 1 or 3 h later. The eyes were harvested and eye tissues and the lacrimal glands were dissected, homogenized and the test compounds were extracted by acetonitrile and analyzed by HPLC, as described under Compound Synthesis described herein. Compounds 1 and 2 were detected at 328 nm, and compound 5 at 260 nm. Table 7 shows the results obtained. All three compounds can unexpectedly, readily, and rapidly reach the posterior chamber of the eye.

TABLE 7

Drug levels in rabbit ocular tissues

| Tissue | Compound 1 20% | | Compound 2 20% | | Compound 5 20% | |
| --- | --- | --- | --- | --- | --- | --- |
| | 1 hr | 3 hr | 2 hr | 3 hr | 40 min | 60 min |
| Cornea | 61.8 | 16.2 | 106.1 | 46.0 | 75.7 | 96.7 |
| Conjunctiva | 71.6 | 52.5 | 16.1 | 13.5 | 33.2 | 35.1 |
| Sclera | 10.1 | 2.5 | 50.7 | 22.4 | 1.3 | 0.6 |
| Iris | 6.9 | 7.6 | 9.9 | 9.8 | 0.6 | 1.9 |
| Lens | 20.2 | 4.6 | 0.3 | 4.0 | 0.0 | 0.0 |
| Aqueous humor | 1.5 | 0.8 | 8.2 | 2.0 | 0.0 | 0.0 |
| Vitreous | 0.9 | 0.5 | 1.2 | NA | 0.0 | 0.0 |
| Retina | 7.5 | 1.8 | 4.1 | 1.7 | 1.8 | 3.4 |
| Ciliary body | ND | ND | ND | ND | 0.0 | 4.2 |
| Choroid | 4.1 | 2.1 | 5.3 | 6.4 | NA | NA |
| Lacrimal gland | 2.2 | 0.2 | ND | ND | 0.0 | 0.0 |

ND: Not Detectable;
NA: Not Assayed

Ocular PK/biodistribution studies in rats using another exemplary compound, compound 6, demonstrated the following. Compound 6 3% (formulated in polyethylene glygol 155; Tween 80% 1%; Kolliphor EL 10%, made to 100% with normal saline; pH 7.2) was injected iv as a single dose of 30 mg/kg. Its retina levels were 4.9 μM and 1 μM at 1 h and 2 h, respectively (the corresponding sclera levels were similar, 3.2 μM and 2.0 μM). When compound 6 was given ip (in corn oil) as a single dose of 100 mg/kg its retina levels became detectable at 3 h (3.2 μM) and remained at 2.8 μM at 4 h and 6 h. Similarly, after its single topical administration, compound 6 3% (formulated in vitamin E TPGS 16%, mannitol 3.2% boric acid 1.2% and polyquad 0.005%, pH 7.2) produced retinal levels of 2.1 μM at 4 h. The biodistribution of compound 2 in human eyes that were recently removed from deceased donors and kept on ice until used within hours was also evaluated. In this study, compound 2 was dissolved in pure water; its pH was adjusted to 4.8±0.1 and its osmolarity to 290 mOsm. The final concentration of compound 2 was 10% (w/v).

The anterior surface of each was brought into contact with the above solution of compound 2 at 37° C.; the solution level was about 3 mm above the cornea edge. After 1 minute or 10 minutes the eyes were rinsed thoroughly with PBS, incubated for 1 h, and dissected to harvest the retina, choroid, aqueous humor, ciliary body, iris and cornea, which ere assayed by HPLC. As shown in the below table, compound 2 did reach the posterior segment of the eye.

| | Compound 2, μM | |
| --- | --- | --- |
| Tissue | 1 minute exposure | 10 minutes exposure |
| retina | 12.6 | 46.6 |
| choroid | 425.9 | 273.5 |
| aqueous humor | 1.0 | 5.3 |
| ciliary body | 124.6 | 206.9 |
| iris | 43.1 | 10.3 |
| cornea | 166.3 | 512.6 |

Example 14: Exemplary Compounds Inhibit Oxygen Induced Retinopathy In Vivo

Several animal models have been explored to understand retinal vascular development. The mouse model of oxygen-induced retinopathy is the most widely used, and has played a pivotal role in our understanding of retinal angiogenesis and in the development of therapeutics such as anti-vascular endothelial growth factor injections for wet age-related macular degeneration. In this model, retinas possess extensive central vaso-obliteration with pathologic neovessels forming around the junction of the vascular and avascular zones, mirroring oxygen-induced retinopathy in humans.

C57BL/6 mice were reared in 75±2% oxygen air starting on postnatal day 7 (P7) and moved into room air on P12, when they were injected intravitreally with 1 μl of 1% compound 6 solution or vehicle. On P17, the pups were euthanized, both eyes were enucleated and fixed with 4% paraformaldehyde (PFA). Following several intermediate steps, the retina was existed and fixed further with 4% PFA overnight. After appropriate washings, the retina was incubated with 10 μg/ml of FITC-conjugated anti-lectin antibody overnight and retina flat-mounts were prepared on glass slides and evaluated by fluorescence microscopy. The areas of the avascular, neovascular and whole retina were determined using ImageJ software.

As shown in FIG. 19, compared to vehicle-treated controls, treatment of these mice with compound 6, dramatically reduced the central avascular area (75% inhibition; p<0.001)

as well as the peripheral neovascularization (51% inhibition; p<0.04), returning retinal vasculature towards normal.

Figure 20:
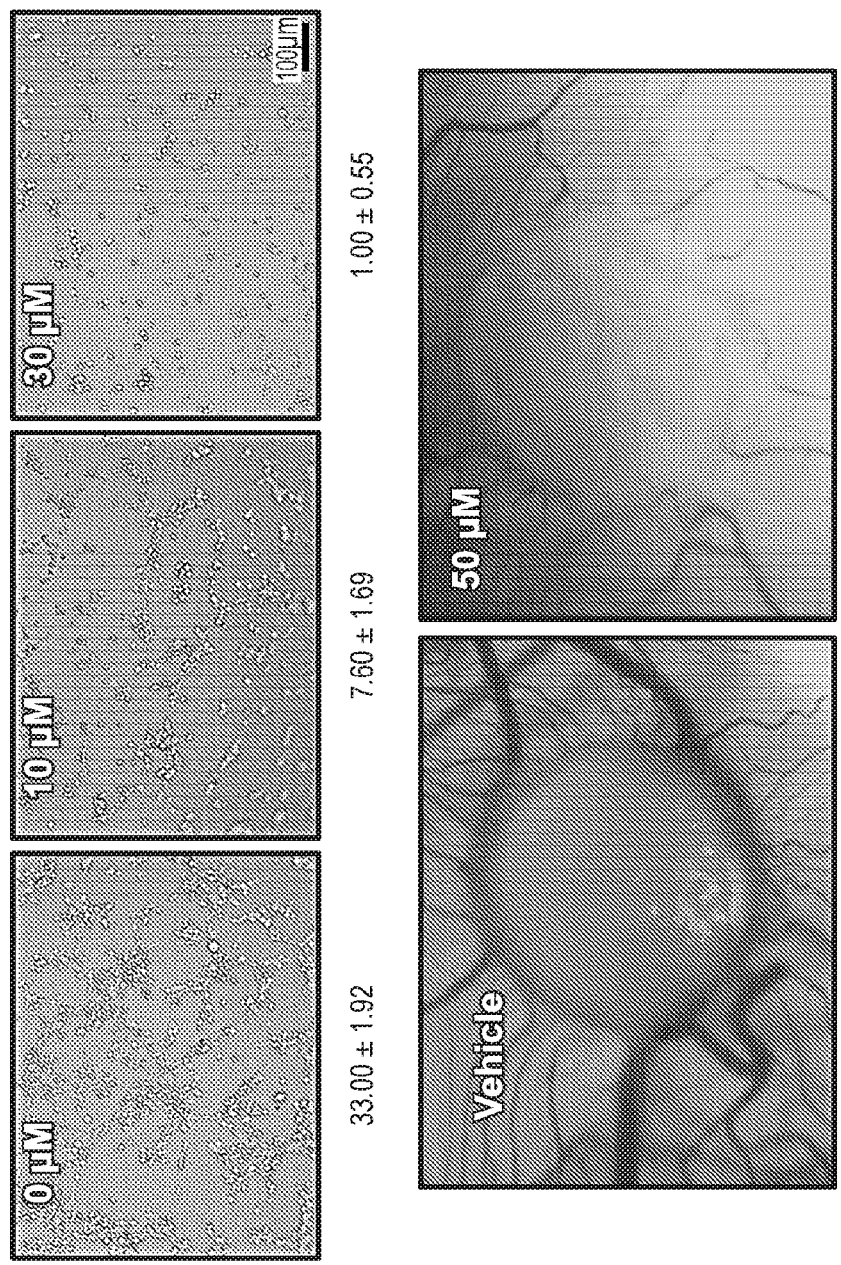
FIG. 20 illustrates the effect of compound 6 on angiogenesis. Compound 6 was applied at various concentrations to HUVEC human endothelial cells cultured appropriate extracellular matrix support, to form capillary-like structures (a.k.a tubs). Images of chorioallantoic membranes show that treatment with compound 6 (placed inside the sponge at the center of each image from which it was slowly released into the surrounding tissues) markedly suppressed the formation of new vessels, whereas the main large vessels, already formed, remained unchanged.

Consistent with these findings is the ability of compound 6 to inhibit vessel formation in vitro (FIG. 20) using a) the tube formation assay (it models the reorganization stage of angiogenesis) by cultured human vascular endothelial cells (HUVEC) in which these two compounds markedly suppressed the formation of capillary-like structures. (a.k.a. tubes), with for example compound 6 30 µM suppressing branch points by 97% (p<0.001); and b) The chicken embryo chorioallantoic membrane assay, an established model for studying neovascularization, in which compound 5 reduced the formation of new vessels by 21% (58±4.9 to 46±2.1; p<0.04) and compound 6 reduced it by 37% (42.6±8.2 to 27±1.5; p<0.03).

In another study, the same mouse model of oxygen-induced retinopathy described above was used. In this study, mice were treated daily with an aqueous solution of compound 2 (pH=4.6, osmolarity=282 mOsm; concentration=10% w/v) from postnatal day 12 to day 17. Compound 2 was administered as one eye drop per eye every 2 hours during the day time for a total of 5 administrations daily. At the end of the study, mice were euthanized and their retinas dissected and studied by immunofluorescence using an antibody against lectin I, isolectin B4 (Vector Laboratories) and evaluated as above.

Figure 21A:
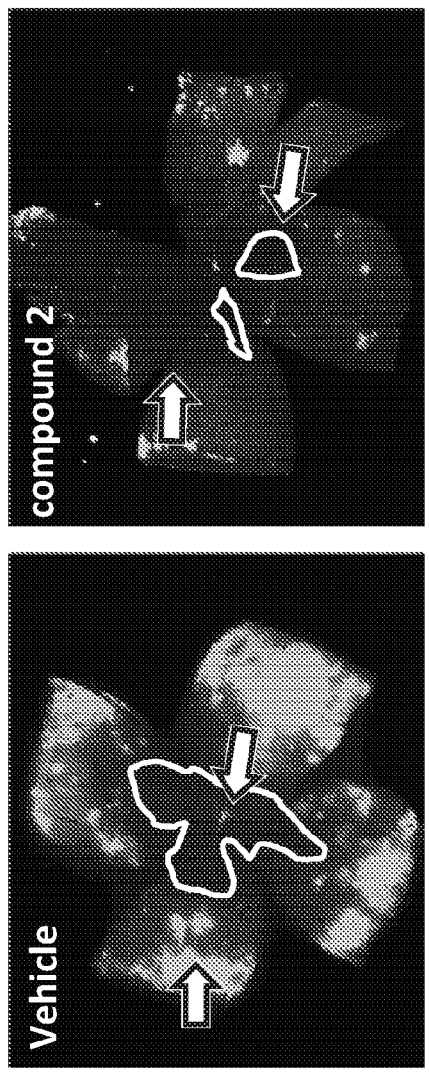
FIG. 21A: Retinal flat mounts from C57Bl/6 mice at postnatal day 17 under oxygen-induced retinopathy conditions stained with isolectin B4 to label the vasculature. Vehicle treated mice (left) show the central avascular area (blue arrow) and the peripheral neovascularization (red arrow). Compound 2 (right) normalized both.
Figure 21B:
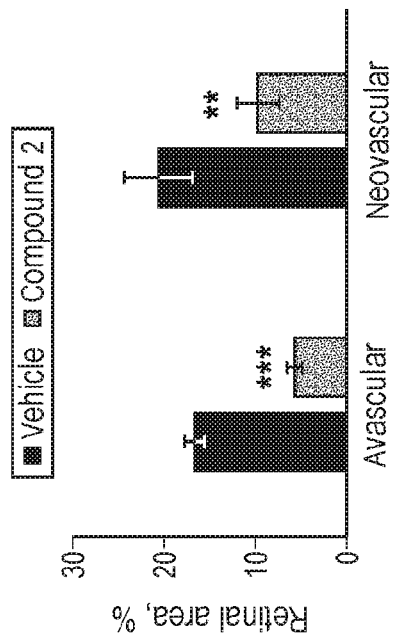
FIG. 21B: Quantification of the avascular and neovascular areas of the retina, expressed as percentage of the entire retina surface area (n=8/group). Values are mean±SEM. Compared to vehicle, *, $p<0.0001$; , $p<0.029$ While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art, which fall within the scope and spirit of the principles of the presently disclosed embodiments.

FIG. 21 demonstrates that compound 2 had a major effect on retinopathy. Specifically, compound 2 significantly reduced the avascular area (vehicle=16.8±1.1 vs. compound 2=5.8±0.8; p<0.0001) and also the neovascular area (vehicle=20.7±3.7 vs. compound 2=9.9±2.2; p<0.029) of the retina. n=8 group.

A number of patent and non-patent publications are cited herein in order to describe the state of the art to which this invention pertains. The entire disclosure of each of these publications is incorporated by reference herein.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

REFERENCES

1. Prager G W, Braga S, Bystricky B, Qvortrup C, Criscitiello C, Esin E, et al. Global cancer control: responding to the growing burden, rising costs and inequalities in access. ESMO Open 2018; 3(2):e000285.
2. Global Burden of Disease Cancer C, Fitzmaurice C, Akinyemiju T F, Al Lami F H, Alam T, Alizadeh-Navaei R, et al. Global, Regional, and National Cancer Incidence, Mortality, Years of Life Lost, Years Lived With Disability, and Disability-Adjusted Life-Years for 29 Cancer Groups, 1990 to 2016: A Systematic Analysis for the Global Burden of Disease Study. JAMA Oncol 2018.
3. Fidler M M, Bray F, Soerjomataram I. The global cancer burden and human development: A review. Scand J Public Health 2018; 46(1):27-36.
4. Nikolaou M, Pavlopoulou A, Georgakilas A G, Kyrodimos E. The challenge of drug resistance in cancer treatment: a current overview. Clin Exp Metastasis 2018; 35(4):309-18.
5. Reid B M, Permuth J B, Sellers T A. Epidemiology of ovarian cancer: a review. Cancer Biol Med 2017; 14(1): 9-32.
6. Cortez A J, Tudrej P, Kujawa K A, Lisowska K M. Advances in ovarian cancer therapy. Cancer Chemother Pharmacol 2018; 81(1):17-38.
7. Giornelli G H. Management of relapsed ovarian cancer: a review. Springerplus 2016; 5(1):1197.
8. Doubeni C A, Doubeni A R, Myers A E. Diagnosis and Management of Ovarian Cancer. Am Fam Physician 2016; 93(11):937-44.
9. Matulonis U A, Sood A K, Fallowfield L, Howitt B E, Sehouli J, Karlan B Y. Ovarian cancer. Nat Rev Dis Primers 2016; 2:16061.
10. Duh E J, Sun J K, Stitt A W. Diabetic retinopathy: current understanding, mechanisms, and treatment strategies. JCI Insight 2017; 2(14).
11. National Institutes of Health. National Cancer Institute. Surveillance, Epidemiology, and End Results Program. Statistical summaries: cancer stat fact sheets (ovary) and cancer statistics review (CSR), 1975-2013, http://seer.cancer.gov/statistics/summaries.html, 2016.
12. Rosen D G, Yang G, Liu G, Mercado-Uribe I, Chang B, Xiao X S, et al. Ovarian cancer: pathology, biology, and disease models. Front Biosci (Landmark Ed) 2009; 14:2089-102.
13. Itamochi H. Targeted therapies in epithelial ovarian cancer: Molecular mechanisms of action. World J Biol Chem 2010; 1(7):209-20.
14. Coward J I, Middleton K, Murphy F. New perspectives on targeted therapy in ovarian cancer. Int J Womens Health 2015; 7:189-203.
15. Westin S N, Herzog T J, Coleman R L. Investigational agents in development for the treatment of ovarian cancer. Invest New Drugs 2013; 31(1):213-29.
16. Markman M, Walker J L. Intraperitoneal chemotherapy of ovarian cancer: a review, with a focus on practical aspects of treatment. J Clin Oncol 2006; 24(6):988-94.
17. Narod S. Can advanced-stage ovarian cancer be cured? Nat Rev Clin Oncol 2016; 13(4):255-61.
18. Coleman R L, Monk B J, Sood A K, Herzog T J. Latest research and treatment of advanced-stage epithelial ovarian cancer. Nat Rev Clin Oncol 2013; 10(4):211-24.
19. Romero I, Bast R C, Jr. Minireview: human ovarian cancer: biology, current management, and paths to personalizing therapy. Endocrinology 2012; 153(4):1593-602.

20. Vaughan S, Coward J I, Bast R C, Jr., Berchuck A, Berek J S, Brenton J D, et al. Rethinking ovarian cancer: recommendations for improving outcomes. Nat Rev Cancer 2011; 11(10):719-25.
21. Bowtell D D, Bohm S, Ahmed A A, Aspuria P J, Bast R C, Jr., Beral V, et al. Rethinking ovarian cancer II: reducing mortality from high-grade serous ovarian cancer. Nat Rev Cancer 2015; 15(11):668-79.
22. Cheng K W, Wong C C, Alston N, Mackenzie G G, Huang L, Ouyang N, et al. Aerosol administration of phospho-sulindac inhibits lung tumorigenesis. Mol Cancer Ther 2013; 12(8): 1417-28.
23. Mackenzie G G, Sun Y, Huang L, Xie G, Ouyang N, Gupta R C, et al. Phospho-sulindac (OXT-328), a novel sulindac derivative, is safe and effective in colon cancer prevention in mice. Gastroenterology 2010; 139(4):1320-32.
24. Pakos-Zebrucka K, Koryga I, Mnich K, Ljujic M, Samali A, Gorman A M. The integrated stress response. EMBO Rep 2016; 17(10):1374-95.
25. Oakes S A, Papa F R. The role of endoplasmic reticulum stress in human pathology. Annu Rev Pathol 2015; 10:173-94.
26. Rigas B, Sun Y. Induction of oxidative stress as a mechanism of action of chemopreventive agents against cancer. Br J Cancer 2008; 98(7):1157-60.
27. Sun Y, Huang L, Mackenzie G G, Rigas B. Oxidative stress mediates through apoptosis the anticancer effect of phospho-nonsteroidal anti-inflammatory drugs: implications for the role of oxidative stress in the action of anticancer agents. J Pharmacol Exp Ther 2011; 338(3): 775-83.
28. Yokoyama C, Sueyoshi Y, Ema M, Mori Y, Takaishi K, Hisatomi H. Induction of oxidative stress by anticancer drugs in the presence and absence of cells. Oncol Lett 2017; 14(5):6066-70.
29. Lin DTS, Davis N G, Conibear E. Targeting the Ras palmitoylation/depalmitoylation cycle in cancer. Biochem Soc Trans 2017; 45(4):913-21.
30. Olivares A M, Althoff K, Chen G F, Wu S, Morrisson M A, DeAngelis M M, et al. Animal Models of Diabetic Retinopathy. Curr Diab Rep 2017; 17(10):93.
31. Kim C B, D'Amore P A, Connor K M. Revisiting the mouse model of oxygen-induced retinopathy. Eye Brain 2016; 8:67-79.

The invention claimed is:

1. A compound or a pharmaceutically acceptable salt, solvate, hydrate, cocrystal, or prodrug thereof, selected from Compound 1, Compound 2, Compound 3, and Compound 4:

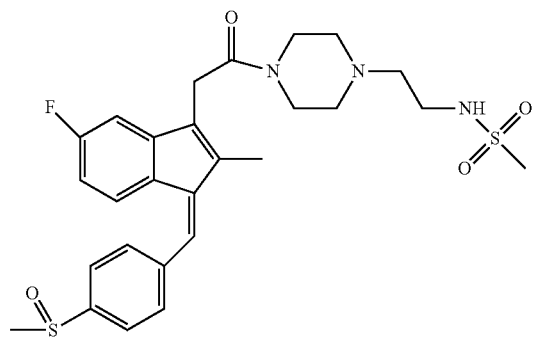

Compound 1

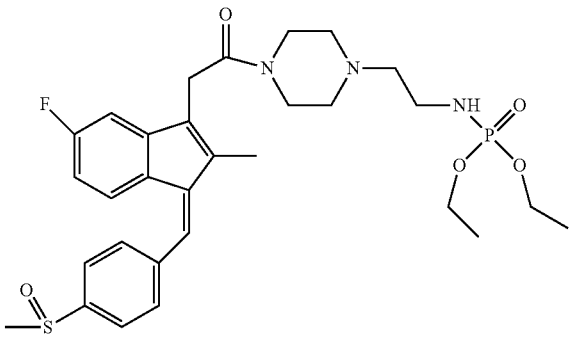

Compound 2

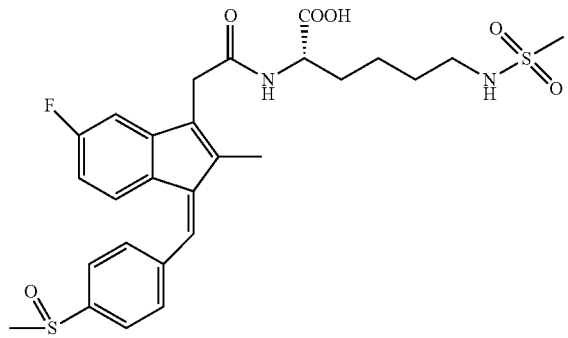

Compound 3

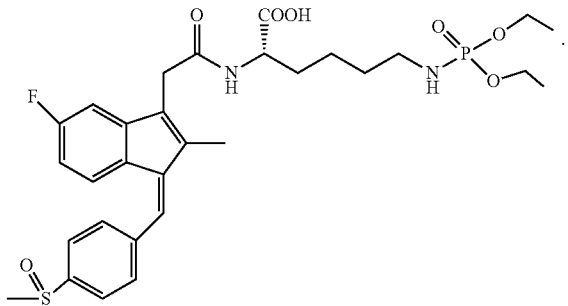

Compound 4

2. The compound of claim 1, or the pharmaceutically acceptable salt, solvate, hydrate, cocrystal, or prodrug thereof, wherein the compound or pharmaceutically acceptable salt, solvate, hydrate, cocrystal, or prodrug thereof has anti-inflammatory, anticancer, or antiangiogenic effects.

3. A pharmaceutical composition comprising a compound claim 1, or a pharmaceutically acceptable salt, solvate, hydrate, cocrystal, or prodrug thereof, and a pharmaceutically acceptable excipient.

4. The compound of claim 1, wherein the compound, or the pharmaceutically acceptable salt, solvate, hydrate, cocrystal, or prodrug thereof, inhibits VEGF expression.

5. The compound of claim 1, wherein the compound is Compound 1

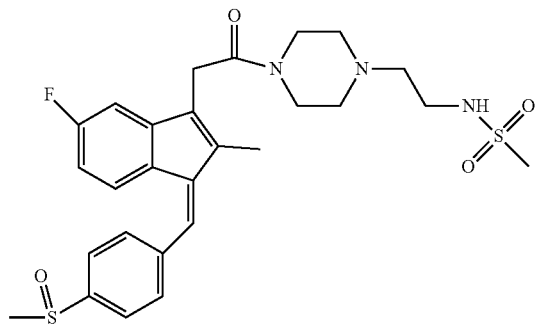

Compound 1 or a pharmaceutically acceptable salt, solvate, hydrate, cocrystal, or prodrug thereof.

6. The compound of claim 1, wherein the compound is Compound 2

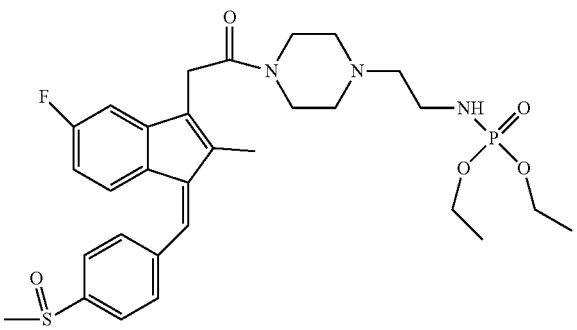

Compound 1 or a pharmaceutically acceptable salt, solvate, hydrate, cocrystal, or prodrug thereof.

7. The compound of claim 1, wherein the compound is Compound 3

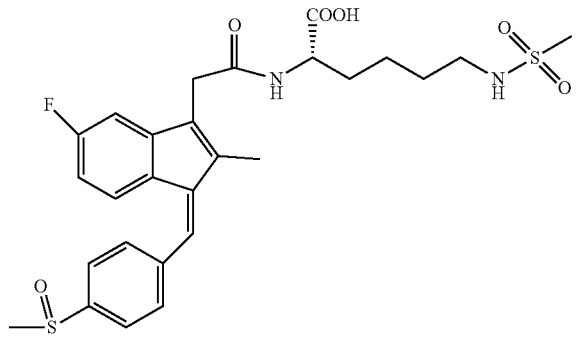

Compound 3 or a pharmaceutically acceptable salt, solvate, hydrate, cocrystal, or prodrug thereof.

8. The compound of claim 1, wherein the compound is Compound 4

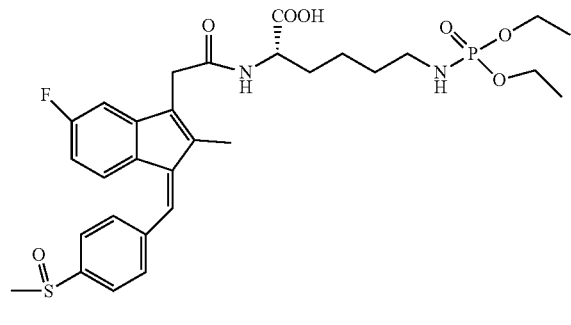

Compound 4 or a pharmaceutically acceptable salt, solvate, hydrate, cocrystal, or prodrug thereof.

* * * * *